United States Patent
Burgard et al.

(10) Patent No.: US 10,597,684 B2
(45) Date of Patent: Mar. 24, 2020

(54) METHODS AND ORGANISMS WITH INCREASED CARBON FLUX EFFICIENCIES

(71) Applicant: Genomatica, Inc., San Diego, CA (US)

(72) Inventors: Anthony P. Burgard, Bellefonte, PA (US); Robin E. Osterhout, San Diego, CA (US); Stephen J. Van Dien, Encinitas, CA (US); Priti Pharkya, San Diego, CA (US); Tae Hoon Yang, San Diego, CA (US); Jungik Choi, San Diego, CA (US)

(73) Assignee: Genomatica, Inc., San Diego, CA (US)

(*) Notice: Subject to any disclaimer, the term of this patent is extended or adjusted under 35 U.S.C. 154(b) by 0 days.

(21) Appl. No.: 15/108,259

(22) PCT Filed: Dec. 23, 2014

(86) PCT No.: PCT/US2014/072178
§ 371 (c)(1),
(2) Date: Jun. 24, 2016

(87) PCT Pub. No.: WO2015/100338
PCT Pub. Date: Jul. 2, 2015

(65) Prior Publication Data
US 2016/0326553 A1  Nov. 10, 2016

Related U.S. Application Data

(60) Provisional application No. 61/921,292, filed on Dec. 27, 2013, provisional application No. 62/013,390, filed on Jun. 17, 2014.

(51) Int. Cl.
| | | |
|---|---|---|
| *C12P 7/18* | (2006.01) | |
| *C12P 7/42* | (2006.01) | |
| *C07K 14/245* | (2006.01) | |
| *C12N 9/00* | (2006.01) | |
| *C12N 1/20* | (2006.01) | |
| *C12N 9/88* | (2006.01) | |
| *C12N 9/52* | (2006.01) | |
| *C12N 15/52* | (2006.01) | |
| *C12N 9/16* | (2006.01) | |
| *C12N 9/02* | (2006.01) | |
| *C12N 9/12* | (2006.01) | |

(52) U.S. Cl.
CPC ............. *C12P 7/18* (2013.01); *C07K 14/245* (2013.01); *C12N 1/20* (2013.01); *C12N 9/0036* (2013.01); *C12N 9/0057* (2013.01); *C12N 9/1205* (2013.01); *C12N 9/16* (2013.01); *C12N 9/52* (2013.01); *C12N 9/88* (2013.01); *C12N 9/93* (2013.01); *C12N 15/52* (2013.01); *C12P 7/42* (2013.01); *C12Y 106/01002* (2013.01); *C12Y 110/03* (2013.01); *C12Y 207/0104* (2013.01); *C12Y 301/00* (2013.01); *C12Y 301/02* (2013.01); *C12Y 301/02002* (2013.01); *C12Y 304/21092* (2013.01); *C12Y 401/01031* (2013.01); *C12Y 401/01032* (2013.01)

(58) Field of Classification Search
CPC ...... C07K 14/245; C12N 1/20; C12N 9/0036; C12N 9/0057; C12N 9/1205; C12N 9/16; C12N 9/93; C12N 15/52; C12N 9/88; C12N 9/52; C12P 7/18; C12P 7/42; C12Y 207/0104; C12Y 110/03; C12Y 106/01002; C12Y 401/01032; C12Y 304/21092; C12Y 301/02002; C12Y 301/02; C12Y 301/00; C12Y 401/01031
See application file for complete search history.

(56) References Cited

U.S. PATENT DOCUMENTS

| | | |
|---|---|---|
| 7,858,350 B2 | 12/2010 | Burk et al. |
| 7,947,483 B2 | 5/2011 | Burgard et al. |
| 7,977,084 B2 | 7/2011 | Sun et al. |
| 8,026,386 B2 | 9/2011 | Burk et al. |
| 8,062,871 B2 | 11/2011 | Burgard et al. |
| 8,067,214 B2 | 11/2011 | Burk et al. |
| 8,129,154 B2 | 3/2012 | Burk et al. |
| 8,129,155 B2 | 3/2012 | Trawick et al. |
| 8,129,169 B2 | 3/2012 | Van Dien et al. |
| 8,241,877 B2 | 8/2012 | Burgard et al. |
| 8,268,607 B2 | 9/2012 | Burgard et al. |
| 8,323,950 B2 | 12/2012 | Burk et al. |
| 8,377,666 B2 | 2/2013 | Haselbeck et al. |
| 8,377,680 B2 | 2/2013 | Burk et al. |

(Continued)

FOREIGN PATENT DOCUMENTS

| | | |
|---|---|---|
| WO | WO 2003/072785 A2 | 9/2003 |
| WO | WO 2007/030830 A2 | 3/2007 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*

(Continued)

*Primary Examiner* — Ganapathirama Raghu
(74) *Attorney, Agent, or Firm* — Jones Day

(57) ABSTRACT

The invention is directed to a non-naturally occurring microbial organism comprising a first attenuation of a succinyl-CoA synthetase or transferase and at least a second attenuation of a succinyl-CoA converting enzyme or a gene encoding a succinate producing enzyme within a multi-step pathway having a net conversion of succinyl-CoA to succinate.

7 Claims, 1 Drawing Sheet
Specification includes a Sequence Listing.

(56) References Cited

U.S. PATENT DOCUMENTS

| | | | |
|---|---|---|---|
| 8,420,375 B2 | 4/2013 | Osterhout et al. | |
| 2003/0059792 A1* | 3/2003 | Palsson | C12N 15/1089 435/6.12 |
| 2007/0111294 A1 | 5/2007 | Burgard et al. | |
| 2008/0199926 A1 | 8/2008 | Burgard et al. | |
| 2009/0047719 A1 | 2/2009 | Burgard et al. | |
| 2009/0075351 A1 | 3/2009 | Burk et al. | |
| 2009/0191593 A1 | 7/2009 | Burk et al. | |
| 2009/0275096 A1 | 11/2009 | Burgard et al. | |
| 2009/0275097 A1 | 11/2009 | Sun et al. | |
| 2009/0305364 A1 | 12/2009 | Burgard et al. | |
| 2010/0009418 A1* | 1/2010 | San | A61K 38/484 435/124 |
| 2010/0021978 A1 | 1/2010 | Burk et al. | |
| 2010/0112654 A1 | 5/2010 | Burk et al. | |
| 2010/0184173 A1 | 7/2010 | Burk et al. | |
| 2010/0304453 A1 | 12/2010 | Trawick et al. | |
| 2010/0323418 A1 | 12/2010 | Burgard | |
| 2010/0330635 A1 | 12/2010 | Burgard et al. | |
| 2011/0003355 A1 | 1/2011 | Clark et al. | |
| 2011/0014668 A1 | 1/2011 | Osterhout et al. | |
| 2011/0045575 A1 | 2/2011 | Van Dien et al. | |
| 2011/0097767 A1 | 4/2011 | Pharkya | |
| 2011/0124911 A1 | 5/2011 | Burk et al. | |
| 2011/0129904 A1 | 6/2011 | Burgard et al. | |
| 2011/0201068 A1 | 8/2011 | Pharkya et al. | |
| 2011/0201089 A1 | 8/2011 | Burgard et al. | |
| 2011/0207185 A1 | 8/2011 | Osterhout | |
| 2011/0217742 A1 | 9/2011 | Sun et al. | |
| 2011/0269204 A1 | 11/2011 | Burk et al. | |
| 2011/0300597 A1 | 12/2011 | Burk et al. | |
| 2011/0312049 A1 | 12/2011 | Osterhout et al. | |
| 2012/0021478 A1 | 1/2012 | Osterhout et al. | |
| 2012/0122171 A1 | 5/2012 | Burk et al. | |
| 2012/0156740 A1 | 6/2012 | Pharkya et al. | |
| 2012/0225466 A1 | 9/2012 | Burk et al. | |
| 2012/0282661 A1 | 11/2012 | Burk et al. | |
| 2012/0329113 A1 | 12/2012 | Burgard et al. | |
| 2012/0329119 A1 | 12/2012 | Burgard et al. | |
| 2013/0011891 A1 | 1/2013 | Burk et al. | |
| 2013/0034884 A1 | 2/2013 | Burgard et al. | |
| 2013/0065279 A1 | 3/2013 | Burk et al. | |
| 2013/0066035 A1 | 3/2013 | Burgard et al. | |
| 2013/0109064 A1 | 5/2013 | Osterhout et al. | |
| 2013/0122563 A1 | 5/2013 | Burk et al. | |
| 2013/0144029 A1 | 6/2013 | Burgard et al. | |
| 2014/0030779 A1 | 1/2014 | Pharkya et al. | |
| 2014/0371417 A1* | 12/2014 | Pharkya | C12N 15/52 528/68 |
| 2015/0240273 A1* | 8/2015 | Ramseier | C12P 7/625 525/450 |

FOREIGN PATENT DOCUMENTS

| | | |
|---|---|---|
| WO | WO 2008/091627 A2 | 7/2008 |
| WO | WO 2008/115840 A2 | 9/2008 |
| WO | WO 2009/023493 A1 | 2/2009 |
| WO | WO 2009/094485 A1 | 7/2009 |
| WO | WO 2009/111672 A1 | 9/2009 |
| WO | WO 2009/135074 A2 | 11/2009 |
| WO | WO 2009/151728 A2 | 12/2009 |
| WO | WO 2009/155382 A1 | 12/2009 |
| WO | WO 2010/030711 A2 | 3/2010 |
| WO | WO 2010/057022 A1 | 5/2010 |
| WO | WO 2010/071697 A1 | 6/2010 |
| WO | WO 2010/127303 A1 | 11/2010 |
| WO | WO 2010/127319 A2 | 11/2010 |
| WO | WO 2010/129936 A1 | 11/2010 |
| WO | WO 2010/132845 A1 | 11/2010 |
| WO | WO 2010/141780 A1 | 12/2010 |
| WO | WO 2010/141920 A2 | 12/2010 |
| WO | WO 2010/144746 A2 | 12/2010 |
| WO | WO 2011/017560 A1 | 2/2011 |
| WO | WO 2011/031897 A1 | 3/2011 |
| WO | WO 2011/047101 A1 | 4/2011 |
| WO | WO 2011/050326 A1 | 4/2011 |
| WO | WO 2011/066076 A1 | 6/2011 |
| WO | WO 2011/071682 A1 | 6/2011 |
| WO | WO 2011/094131 A1 | 8/2011 |
| WO | WO 2011/130378 A1 | 10/2011 |
| WO | WO 2011/137198 A1 | 11/2011 |
| WO | WO 2011/140171 A2 | 11/2011 |
| WO | WO 2012/018624 A2 | 2/2012 |
| WO | WO 2012/082978 A1 | 6/2012 |
| WO | WO 2012/177721 A1 | 6/2012 |
| WO | WO 2012/099621 A1 | 7/2012 |
| WO | WO 2012/106516 A1 | 8/2012 |
| WO | WO 2012/135789 A2 | 10/2012 |
| WO | WO 2012/177599 A2 | 12/2012 |
| WO | WO 2012/177619 A2 | 12/2012 |
| WO | WO 2012/177710 A1 | 12/2012 |
| WO | WO 2012/177726 A1 | 12/2012 |
| WO | WO 2012/177943 A1 | 12/2012 |
| WO | WO 2012/177983 A2 | 12/2012 |
| WO | WO 2013/003432 A1 | 1/2013 |
| WO | WO 2013/012975 A1 | 1/2013 |
| WO | WO 2013/028519 A1 | 2/2013 |
| WO | WO 2013/036764 A1 | 3/2013 |
| WO | WO 2013/040383 A1 | 3/2013 |
| WO | WO 2013/067432 A1 | 5/2013 |
| WO | WO 2013/071226 A1 | 5/2013 |

OTHER PUBLICATIONS

Chica et al., Semi-rational approaches to engineering enzyme activity: combining the benefits of directed evolution and rational design. Curr. Opi. Biotechnol., 2005, vol. 16: 378-384. (Year: 2005).*

Devos et al., Practical limits of function prediction. Proteins: Structure, Function, and Genetics. 2000, vol. 41: 98-107. (Year: 2000).*

Kisselev L., Polypeptide release factors in prokaryotes and eukaryotes-:same function, different structure. Structure, 2002, vol. 10: 8-9. (Year: 2002).*

Seffernick et al., Melamine deaminase and Atrazine chlorohydrolase: 98 percent identical but functionally different. J. Bacteriol., 2001, vol. 183 (8): 2405-2410. (Year: 2001).*

Sen et al., Developments in directed evolution for improving enzyme functions. Appl. Biochem. Biotechnol., 2007, vol. 143: 212-223. (Year: 2007).*

Whisstock et al., Prediction of protein function from protein sequence. Q. Rev. Biophysics., 2003, vol. 36 (3): 307-340. (Year: 2003).*

Wishart et al., A single mutation converts a novel phosphotyrosine binding domain into a dual-specificity phosphatase. J. Biol. Chem., 1995, vol. 270(45): 26782-26785. (Year: 1995).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Chen et al., Assignment of orthologous genes via genome rearrangement. IEE/ACM Trans. Comput. Biol. Biinformatics., 2005, vol. 2(4): 302-315. (Year: 2005).*

Kim et al., Large-scale bi-level strain design approaches and mixed-integer programming solution techniques. PLoS One, 2011, vol. 6(9): e24162, pp. 1-14. (Year: 2011).*

Angov et al., "Codon usage: nature's roadmap to expression and folding of proteins," *Biotechnol. J.*, 6(6):650-659 (2011).

Araujo et al., "Before It Gets Started: Regulating Translation at the 5' UTR," *Comp. Functional Genomics*, Article ID 475731 (2012).

Arps et al., "Genetics of serine pathway enzymes in Methylobacterium extorquens AM1: phosphoenolpyruvate carboxylase and malyl coenzyme A lyase," *J. Bacteriol.*, 175(12):3776-3783 (1993).

Arraiano et al., "The critical role of RNA processing and degradation in the control of gene expression," *FEMS Microbiol. Rev.*, 34:883-932 (2010).

Bekker et al., "Respiration of *Escherichia coli* can be fully uncoupled via the nonelectrogenic terminal cytochrome bd-II oxidase," *J. Bacteriol.*, 191:5510-5517 (2009).

(56) References Cited

OTHER PUBLICATIONS

Bleykasten-Grosshans et al., "Transposable elements in yeasts," *C.R. Biol.*, 334:679-686 (2011).
Brasen et al., "Unusual ADP-forming acetyl-coenzyme A synthetases from the mesophilic halophilic euryarchaeon Haloarcula marismortui and from the hyperthermophilic crenarchaeon Pyrobaculum aerophilum," *Arch. Microbiol.*, 182:277-287 (2004).
Buck et al., "Primary Structure of the Succinyl-CoA Synthetase of *Escherichia coli*," *Biochemistry*, 24:6245-6252 (1985).
Buu et al., "Functional Characterization and Localization of Acetyl-CoA Hydrolase, Ach1p, in *Saccharomyces cerevisiae*," *J. Biol. Chem.*, 278:17203-17209 (2003).
Cary et al., "Cloning and expression of Clostridium acetobutylicum ATCC 824 acetoacetyl-coenzyme A:acetate/butyrate:coenzyme A-transferase in *Escherichia coli*," *Appl. Environ. Microbiol.*, 56(6):1576-1583 (1990).
Castel et al., "RNA interference in the nucleus: roles for small RNAs in transcription, epigenetics and beyond," *Nat. Rev. Genet.*, 14(2):100-112 (2013).
Charrier et al., "A novel class of CoA-transferase involved in shortchain fatty acid metabolism in butyrate-producing human colonic bacteria," *Microbiol.*, 152:179-185 (2006).
Chen et al., "Phosphoenolpyruvate Carboxykinase Assayed at Physiological Concentrations of Metal Ions Has a High Affinity for $CO_2$," *Plant Physiol.*, 128:160-164 (2002).
Clarke et al., "Nucleotide sequence of the pntA and pntB genes encoding the pyridine nucleotide transhydrogenase of *Escherichia coli*," *Eur. J. Biochem.*, 158(3):647-653 (1986).
Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.*, 272(41):25659-25667 (1997).
Cotelesage et al., "How does an enzyme recognize $CO_2$?," *Int. J. Biocehm. Cell Biol.*, 39:1204-1210 (2007).
Daigaku et al., "Loss of heterozygosity in yeast can occur by ultraviolet irradiation during the S phase of the cell cycle," *Mutation Res.*, 600:177-183 (2006).
Deana, "Substrate specificity of a dicarboxyl-CoA: dicarboxylic acid coenzyme A transferase from rat liver mitochondria," *Biochem. Int.*, 26(4):767-773 (1992).
Dietrich et al., "High-throughput metabolic engineering: advances in small-molecule screening and selection," *Annu. Rev. Biochem.*, 79:563-590 (2010).
Donovan et al., "Review: optimizing inducer and culture conditions for expression of foreign proteins under the control of the lac promoter," *J. Ind. Microbiol.*, 16(3):145-154 (1996).
Duncan et al., "Acetate Utilization and Butyryl Coenzyme A (CoA):Acetate-CoA Transferase in Butyrate-Producing Bacteria from the Human Large Intestine," *Appl. Environ. Microbiol.*, 68(10):5186-5190 (2002).
Eikmanns et al., "The phosphoenolpyruvate carboxylase gene of Corynebacterium glutamicum: molecular cloning, nucleotide sequence, and expression," *Mol. Gen. Genet.*, 218:330-339 (1989).
Fernandez-Valverde et al., "Purification of Pseudomonas putida acyl coenzyme A ligase active with a range of aliphatic and aromatic substrates," *Appl. Environ. Microbiol.*, 59(4):1149-1154 (1993).
Fischer et al., "Metabolic flux profiling of *Escherichia coli* mutants in central carbon metabolism using GC-MS," *Eur. J. Biochem.*, 270:880-891 (2003).
Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics*, 68(2):144-151 (2000).
Gabriel et al., "Regulation of the Bacillus subtilis yciC gene and insights into the DNA-binding specificity of the zinc-sensing metalloregulator Zur," *J. Bacteriol.*, 190(10):3482-3488 (2008).
Gobel et al., "Degradation of Aromatics and Chloroaromatics by Pseudomonas sp. Strain B13: Cloning, Characterization, and Analysis of Sequences Encoding 3-Oxoadipate:Succinyl-Coenzyme A (CoA) Transferase and 3-Oxoadipyl-CoA Thiolase," *J. Bacteriol.*, 184(1):216-223 (2002).
Gonzalez et al., "Structure and activity of the Pseudomonas aeruginosa hotdog-fold thioesterases PA5202 and PA2801," *Biochem J.*, 444(3):445-455 (2012).
Gottesman et al., "The ClpXP and ClpAP proteases degrade proteins with carboxy-terminal peptide tails added by the SsrA-tagging system," *Genes Dev.*, 12(9):1338-1347 (1998).
Guo et al., "Preferential Hydrolysis of Aberrant Intermediates by the Type II Thioesterase in *Escherichia coli* Nonribosomal Enterobactin Synthesis: Substrate Specificities and Mutagenic Studies on the Active-Site Residues," *Biochemistry*, 48:1712-1722 (2009).
Haller et al., "Discovering New Enzymes and Metabolic Pathways: Conversion of Succinate to Propionate by *Escherichia coli*," *Biochemistry*, 39(16):4622-4629 (2000).
Hanke et al., "Combined fluxomics and transcriptomics analysis of glucose catabolism via a partially cyclic pentose phosphate pathway in Gluconobacter oxydans 621H," *Appl. Environ. Microbiol.*, 79(7):2336-2348 (2013).
Hansen et al., "The effect of the lacY gene on the induction of IPTG inducible promoters, studied in *Escherichia coli* and Pseudomonas fluorescens," *Curr. Microbiol.*, 36(6):341-347 (1998).
Hayes et al., "Transposon-based strategies for microbial functional genomics and proteomics," *Annu. Rev. Genet.*, 37:3-29 (2003).
Hochstrasser, "Ubiquitin-Dependent Protein Degradation," *Annu. Rev. Genet.*, 30:405-439 (1996).
Hoffmeister et al., "Mitochondrial trans-2-Enoyl-CoA Reductase of Wax Ester Fermentation from Euglena gracilis Defines a New Family of Enzymes Involved in Lipid Synthesis," *J. Biol. Chem.*, 280(6):4329-4338 (2005).
Houseley et al., "The many pathways of RNA Degradation," *Cell*, 136(4):763-776 (2009).
Hunt et al., "Analysis of the mouse and human acyl-CoA thioesterase (ACOT) gene clusters shows that convergent, functional evolution results in a reduced number of human peroxisomal ACOTs," *FASEB J.*, 20(11):1855-1864 (2006).
Jackson, "Proton translocation by transhydrogenase," *FEBS Lett.*, 545(1):18-24 (2003).
Kai et al., "Phosphoenolpyruvate carboxylase: three-dimensional structure and molecular mechanisms," *Arch. Biochem. Biophys.*, 414:170-179 (2003).
Kaschabek et al., "Degradation of Aromatics and Chloroaromatics by *Pseudomonas* sp. Strain B13: Purification and Characterization of 3-Oxoadipate:Succinyl-Coenzyme A (CoA) Transferase and 3-Oxoadipyl-CoA Thiolase," *J. Bacteriol.*, 184(1):207-215 (2002).
Kawasaki et al., "Transcriptional gene silencing by short interfering RNAs," *Curr. Opin. Mol. Ther.*, 7(2):125-131 (2005).
Kessel et al., "Homology in structural organization between *E. coli* ClpAP protease and the eukaryotic 26 S proteasome," *J. Mol. Biol.*, 250(5):587-594 (1995).
Kim et al., "Large-Scale Bi-Level Strain Design Approaches and Mixed-Integer Programming Solution Techniques," *PLoS One*, 6(9):e24162 (2011).
Kim et al., "Effect of Overexpression of Actinobacillus succinogenes Phosphoenolpyruvate Carboxykinase on Succinate Production in *Escherichia coli*," *Appl. Environ. Microbiol.*, 70(2):1238-1241 (2004).
Korolev et al., "Autotracing of *Escherichia coli* acetate CoA-transferase alpha-subunit structure using 3.4 A MAD and 1.9 A native data," *Acta Crystallogr. D. Biol. Crystallogr.*, 58:2116-2121 (2002).
Kosaka et al., "Characterization of the sol Operon in Butanol-Hyperproducing Clostridium saccharoperbutylacetonicum Strain N1-4 and Its Degeneration Mechanism," *Biosci. Biotechnol. Biochem.*, 71(1):58-68 (2007).
Kowalchuk et al., "Contrasting patterns of evolutionary divergence within the Acinetobacter calcoaceticus pca operon," *Gene*, 146:23-30 (1994).
Kurdistani et al., "Histone acetylation and deacetylation in yeast," *Nat. Rev. Mol. Cell. Biol.*, 4(4):276-284 (2003).

(56) References Cited

OTHER PUBLICATIONS

Kuznetsova et al., "Enzyme genomics: Application of general enzymatic screens to discover new enzymes," *FEMS Microbiol. Rev.*, 29(2):263-279 (2005).
Kwon et al., "Influence of Gluconeogenic Phosphoenolpyruvate Carboxykinase (PCK) Expression on Succinic Acid Fermentation in *Escherichia coli* Under High Bicarbonate Condition," *J. Microbiol. Biotechnol.*, 16(9):1448-1452 (2006).
Laivenieks et al., "Cloning, Sequencing, and Overexpression of the *Anaerobiospirillum succiniciproducens* Phosphoenolpyruvate Carboxykinase (pckA) Gene," *Appl. Environ. Microbiol.*, 63(6):2273-2280 (1997).
Lee et al., "Antisense technology in molecular and cellular bioengineering," *Curr. Opin. Biotechnol.*, 14(5):505-511 (2003).
Lee et al., "Cloning and Characterization of *Mannheimia succiniciproducens* MBEL55E Phosphoenolpyruvate Carboxykinase (pckA) Gene," *Biotechnol. Bioprocess. Eng.*, 7:95-99 (2002).
Li et al., "Harnessing homologous recombination in vitro to generate recombinant DNA via SLIC," *Nat. Methods*, 4(3):251-256 (2007).
Lin et al., "Fed-Batch Culture of a Metabolically Engineered *Escherichia coli* Strain Designed for High-Level Succinate Production and Yield Under Aerobic Conditions," *Biotech. Bioeng.*, 90(6):775-779 (2005).
Lutz et al., "Independent and tight regulation of transcriptional units in *Escherichia coli* via the LacR/O, the TetR/O and AraC/I1-I2 regulatory elements," *Nucelic Acids Res.*, 25(6):1203-1210 (1997).
Mack et al., "Conversion of glutaconate CoA-transferase from *Acidaminococcus fermentans* into an acyl-CoA hydrolase by site-directed mutagenesis," *FEBS Lett.*, 405(2):209-212 (1997).
Mann et al., "Protemic analysis of post-translational modifications," *Nature Biotech.*, 21:255-261 (2003).
Matthies et al., "Reciprocal isomerization of butyrate and isobutyrate by the strictly anaerobic bacterium strain WoG13 and methanogenic isobutyrate degradation by a defined triculture," *Appl. Environ. Microbiol.*, 58(5):1435-1439 (1992).
McCue et al., "Gene expression and stress response mediated by the epigenetic regulation of a transposable element small RNA," *PLoS Genet.*, 8(2):e1002474 (2012).
McMahon et al., "Functional screening and in vitro analysis reveal thioesterases with enhanced substrate specificity profiles that improve short-chain fatty acid production in *Escherichia coli*," *Appl. Environ. Microbiol.*, 80(3):1042-1050 (2014).
Miko, "Phenotype Variability: Penetrance and Expressivity," *Nature Education*, 1(1):137 (2008).
Mullins et al., "A Specialized Citric Acid Cycle Requiring Succinyl-Coenzyme A (CoA):Acetate CoA-Transferase (AarC) Confers Acetic Acid Resistance on the Acidophile *Acetobacter aceti*," *J. Bacteriol.*, 190(14):4933-4940 (2008).
Musfeldt et al., "Novel Type of ADP-Forming Acetyl Coenzyme A Synthetase in Hyperthermophilic Archaea: Heterologous Expression and Characterization of Isoenzymes from the Sulfate Reducer *Archaeoglobus fulgidus* and the Methanogen *Methanococcus jannaschii*," *J. Bacteriol.*, 184(3):636-644 (2002).
Naggert et al., "Cloning, Sequencing, and Characterizaion of *Escherichia coli* Thioesterase II," *J Biol. Chem.*, 266(17):11044-11050 (1991).
Nakai et al., "A knowledge base for predicting protein localization sites in eukaryotic cells," *Genomics*, 14(4):897-911 (1992).
Nashizawa et al., "Regulation of inducible gene expression by natural antisense transcripts," *Front Biosci.*, 17:938-958 (2012).
O'Sullivan et al., "Aptasensors—the future of biosensing?," *Anal. Bioanal. Chem.*, 273:44-48 (2002).
Pasquinelli, "MicroRNAs and their targets: recognition, regulation and an emerging reciprocal relationship," *Nat. Rev. Genet.*, 13(4):271-282 (2012).
Pohl et al., "Remarkably Broad Substrate Tolerance of Malonyl-CoA Synthetase, an Enzyme Capable of Intracellular Synthesis of Polyketide Precursors," *J. Am. Chem. Soc.*, 123:5822-5823 (2001).
Portnoy et al., "Aerobic fermentation of D-glucose by an evolved cytochrome oxidase-deficient *Escherichia coli* strain," *Appl. Environ. Microbiol.*, 74(24):7561-7569 (2008).
Przybyla-Zawislak et al., "Genes of succinyl-CoA ligase from *Saccharomyces cerevisiae*," *Eur. J. Biochem.*, 258:736-743 (1998).
Reid et al., "ClpA mediates directional translocation of substrate proteins into the ClpP protease," *Proc. Natl. Acad. Sci. U.S.A.*, 98(7):3768-3772 (2001).
Ringner et al., "Folding free energies of 5'-UTRs impact post-transcriptional regulation on a genomic scale in yeast," *PLoS Comput. Biol.*, 1(7):e72 (2005).
Riviere et al., "Acetyl:Succinate CoA-transferase in Procyclic *Trypanosoma brucei*," *J. Biol. Chem.*, 279:45337-45346 (2004).
Robinson et al., "Studies on rat brain acyl-coenzyme a hydrolase (short chain)," *Biochem. Biophys. Res. Comm.*, 71(4):959-965 (1976).
Russell et al., "Peptide Signals Encode Protein Localization," *J. Bacteriol.*, 189(21):7581-7585 (2007).
Schweiger et al., "On the dehydration of (R)-lactate in the fermentation of alanine to propionate by *Clostridium propionicum*," *FEBS Lett.*, 171(1):79-84 (1984).
Seedorf et al., "The genome of *Clostridium kluyveri*, a strict anaerobe with unique metabolic features," *Proc. Natl. Acad. Sci. U.S.A.*, 105:2128-2133 (2008).
Selmer et al., "Propionate CoA-transferase from *Clostridium propionicum*: Cloning of the gene and identification of glutamate 324 at the active site," *Eur. J. Biochem.*, 269:372-380 (2002).
Shepherd et al., "Compensations for diminished terminal oxidase activity in *Escherichia coli*: cytochrome bd-II-mediated respiration and glutamate metabolism." *J. Biol. Chem.*, 285(24):18464-18472 (2010).
Shestopalov et al., "Aeration-dependent changes in composition of the quinone pool in *Escherichia coli*. Evidence of post-transcriptional regulation of the quinone biosynthesis," *FEBS Lett.*, 404(2-3):272-274 (1997).
Sidhu et al., "DNA sequencing and expression of the formyl coenzyme A transferase gene, frc, from *Oxalobacter formigenes*," *J. Bacteriol.*, 179(10):3378-3381 (1997).
Silverman et al., "Arc and Sfr functions of the *Escherichia coli* K-12 arcA gene product are genetically and physiologically separable," *J .Bacteriol.*, 173(18):5648-5652 (1991).
Simicevic et al., "DNA-centered approaches to characterize regulatory protein-DNA interaction complexes," *Mol. BioSyst,*, 6:462-468 (2010).
Snoswell et al., "Deacylation of acetyl-coenzyme A and acetylcarnitine by liver preparations," *Biochem. J.*, 171(2):299-303 (1978).
Sohling et al., "Molecular Analysis of the Anaerobic Succinate Degradation Pathway in *Clostridium kluyveri*," *J. Bacteriol.*, 178:871-880 (1996).
Song et al., "Structure, Function, and Mechanism of the Phenylacetate Pathway Hot Dog-fold Thioesterase Paal," *J. Biol. Chem.*, 281(16):11028-11038 (2006).
Sramek et al., "Purification and Properties of *Escherichia coli* Coenzyme A-Transferase," *Arch. Biochem. Biophys.*, 171:14-26 (1975).
Stols et al., "New vectors for co-expression of proteins: Structure of *Bacillus subtilis* ScoAB obtained by high-throughput protocols," *Protein Expr. Purif.*, 53:396-403 (2007).
Sunohara et al., "Nascent-peptide-mediated ribosome stalling at a stop codon induces mRNA cleavage resulting in nonstop mRNA that is recognized by tmRNA," *RNA*, 10(3):378-386 (2004).
Sunohara et al., "Ribosome stalling during translation elongation induces cleavage of mRNA being translated in *Escherichia coli*," *J. Biol. Chem.*, 279(15):15368-15375 (2004).
Tanaka et al., "Cloning and characterization of a human orthologue of testis-specific succinyl CoA: 3-oxo acid CoA transferase (Scot-t) cDNA," *Mol. Hum. Reprod.*, 8(1):16-23 (2001).
Toyota et al., "Differential substrate specificity and kinetic behavior of *Escherichia coli* YfdW and *Oxalobacter formigenes* formyl coenzyme A transferase," *J. Bacteriol.*, 190(7):2556-2564 (2008).
Valdes-Hevia et al., "Isolation and characterization of the gene encoding phosphoenolpyruvate carboxykinase from *Saccharomyces cerevisiae*," *FEBS Lett.*, 258(2):313-316 (1989).

(56) References Cited

OTHER PUBLICATIONS

Van Grinsven et al., "Acetate:Succinate CoA-transferase in the Hydrogenosomes of Trichomonas vaginalis," *J. Biol. Chem.*, 283:1411-1418 (2008).

Vanderwinkel et al., "Growth of *Escherichia coli* on fatty acids: requirement for coenzyme A transferase activity," *Biochem. Biophys. Res. Commun.*, 33(6):902-908 (1968).

Wang et al., "Activation of silent genes by transposons Tn5 and Tn10," *Genetics*, 120(4):875-885 (1988).

Wang et al., "Identification of a Type III Thioesterase Reveals the Function of an Operon Crucial for Mtb Virulence," *Chem. Biol.*, 14:543-551 (2007).

Wang et al., "Overview of regulatory strategies and molecular elements in metabolic engineering of bacteria," *Mol. Biotechnol.*, 52(2):300-308 (2012).

Westin et al., "The Identification of a Succinyl-CoA Thioesterase Suggests a Novel Pathway for Succinate Production in Peroxisomes," *J. Biol. Chem.*, 280(46):38125-38132 (2005).

Wieland et al., "Engineering of ribozyme-based riboswitches for mammalian cells," *Methods*, 53(3):351-357 (2012).

Wiesenborn et al., "Coenzyme A transferase from Clostridium acetobutylicum ATCC 824 and its role in the uptake of acids," *Appl. Environ. Microbiol.*, 55(2):323-329 (1989).

Yang et al., "Collaborative spirit of histone deacetylases in regulating chromatin structure and gene expression," *Curr. Opin. Genet. Dev.*, 13(2):143-153 (2003).

Yang, "13C-Based Metabolic Flux Analysis: Fundamentals and Practice," *Systems Metabolic Engineering:Methods and Protocols*, Alper HS Ed., pp. 297-334 (2013).

Yim et al., "Metabolic engineering of *Escherichia coli* for direct production of 1,4-butanediol," *Nat. Chem. Biol.*, 7(7):445-452 (2011).

Yuan et al., "Prokaryotic ubiquitin-like ThiS fusion enhances the heterologous protein overexpression and aggregation in *Escherichia coli*," *PLoS One*, 8(4):e62529 (2013).

Zeiher et al., "Identification and Characterzation of Mitochondrial Acetyl-Coenzyme A Hydrolase from Pisum sativum L. Seedlings," *Plant Physiol.*, 94:20-27 (1990).

Zhuang et al., "Divergence of function in the hot dog fold enzyme superfamily: the bacterial thioesterase YciA," *Biochemistry*, 47:2789-2796 (2008).

\* cited by examiner

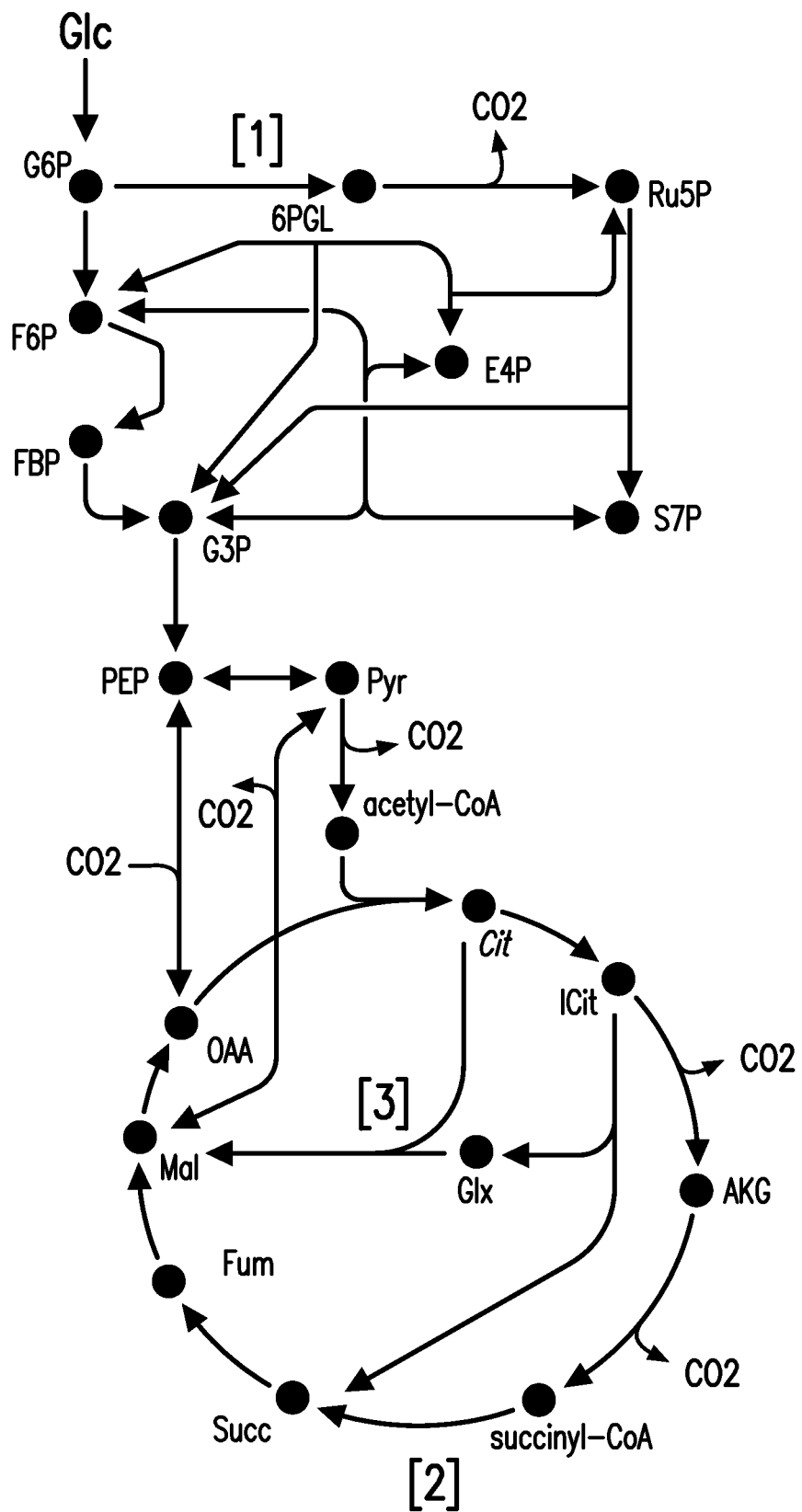

METHODS AND ORGANISMS WITH INCREASED CARBON FLUX EFFICIENCIES

CROSS-REFERENCE TO RELATED APPLICATIONS

This application is a 371 national stage application of international application Serial No. PCT/US2014/072178 filed Dec. 23, 2014, which claims the benefit of U.S. Ser. No. 61/921,292 filed Dec. 27, 2013; and U.S. Ser. No. 62/013,390 filed Jun. 17, 2014; each of which is incorporated herein by reference in its entirety.

BACKGROUND OF THE INVENTION

The invention provides non-naturally occurring microbial organisms having reduced carbon flux from succinyl-CoA to succinate through an oxidative TCA cycle. The invention also provides methods of reducing carbon flux from succinyl-CoA to succinate through an oxidative TCA cycle using the microbial organisms.

Carbon loss, through excess $CO_2$ production, can come from three main routes in central metabolism: the pentose phosphate pathway, the glyoxylate shunt and the oxidative tricarboxylic acid (TCA) cycle. The main $CO_2$ generating reaction of the pentose phosphate pathway is phosphogluconate dehydrogenase. Enzymes which can contribute to carbon loss in the TCA cycle and glyoxylate shunt include, for example, pyruvate dehydrogenase, pyruvate formate lyase, pyruvate oxidase, alpha-ketoglutarate dehydrogenase, isocitrate dehydrogenase, phosphoenolpyruvate carboxykinase, and malic enzyme.

Carbon loss can also come from other metabolic reactions that include, for example, the glycine cleavage system, formate hydrogen lyase, formate dehydrogenase, glutamate decarboxylase, pyruvate oxidase, acetolactate synthase and 2-oxo-4-methyl-3-carboxypentanoate decarboxylase, aspartate decarboxylase, lysine decarboxylase, diaminopimelate decarboxylase and enzymes involved in fatty acid biosynthesis.

Thus, there exists a need for alternative means for decreasing carbon loss and increasing carbon flux efficiencies. The present invention satisfies this need and provides related advantages as well.

SUMMARY OF INVENTION

The invention is directed to a non-naturally occurring microbial organism comprising a first attenuation of a succinyl-CoA synthetase or transferase and at least a second attenuation of a succinyl-CoA converting enzyme or a gene encoding a succinate producing enzyme within a multi-step pathway having a net conversion of succinyl-CoA to succinate. The succinyl-CoA synthetase can be encoded by sucCD. The succinyl-CoA converting enzyme can be the enzyme YciA CoA hydrolase. The microbial organism can further include increased expression of a pyridine nucleotide transhydrogenase including where the pyridine nucleotide transhydrogenase is encoded by pntAB. The microbial organism also can include attenuation of a TCA cycle enzyme other than a succinyl-CoA synthetase or transferase. The microbial organism can include a metabolically engineered pathway for producing a bioderived compound from a TCA cycle intermediate or a TCA cycle substrate. The bioderived compound can be 4-hydroxybutyrate (4HB), 1,4-butanediol (1,4-BDO), 1,3-butanediol (1,3-BDO), polyhydroxylbutanoate (PHB), butadiene, adipate, 6-aminocaproate, caprolactam or methacrylic acid, or other compounds disclosed herein. The invention is directed to other genetic alterations for enhancing the production of a bioderived compound.

BRIEF DESCRIPTION OF THE DRAWINGS

FIG. 1 shows central metabolic pathways that generate CO2, including (1) the pentose phosphate pathway; (2) the complete oxidative TCA cycle; and (3) the glyoxylate shunt. Abbreviations: Glc is glucose, G6P is glucose-6-phosphate, F6P is fructose-6-phosphate, FBP is fructose-1,6-bisphosphate, G3P is glyceraldehyde-3-phosphate, PEP is phosphoenolpyruvate, Pyr is pyruvate, cit is citrate, Icit is isocitrate, AKG is alpha-ketoglutarate, Succ is succinate, Fum is fumarate, Mal is malate, OAA is oxaloacetate, 6PGL is 6-phospogluconolactone, Ru5P is ribulose-5-phosphate, E4P is erythrose-4-phosphate, S7P is sedoheptulose-7-phosphate, and Glx is glyoxylate.

DETAILED DESCRIPTION OF THE INVENTION

The invention provides non-naturally occurring microbial organisms having reduced carbon flux from succinyl-CoA to succinate through an oxidative TCA cycle, wherein the microbial organism includes one or more genetic disruptions. The invention also provides methods of reducing carbon flux from succinyl-CoA to succinate through an oxidative TCA cycle using the microbial organisms.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include, for example, enzymes or proteins that convert succinyl-CoA to succinate, tricarboxylic acid (TCA) cycle enzymes, pyridine nucleotide transhydrogenase, NADH dehydrogenase, ubiquinol oxidase, menaquinone biosynthetic enzymes, menaquinol biosynthetic enzymes, phosphoenoylpyruvate carboxykinase (PEPCK), phosphoenoylpyruvate carboxylase (PPC) and enzymes or proteins within a bioderived product biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

A parent microbial organism or parental microbial organism, when used in reference to a microbial organism having a referenced gene disruption or other genetic alteration, is understood to mean an organism or strain having a substantially similar genotype as the microbial organism having the referenced gene disruption or other genetic alteration if the referenced gene disruption or other genetic alteration were excluded from the comparison. Accordingly, a parent microbial organism refers to a substantially similar genotype of a strain wherein the referenced gene disruption or other genetic alteration is introduced to generate a modified organism. It is understood that a parent microbial organism can differ by more than one genetic alteration, either gene addition and/or disruption, for example, depending on whether a single or multiple genetic alterations are being considered. One skilled in the art will readily understand the meaning of such a parent microbial organism in that the microbial organism is considered to be an appropriate control, as understood in the art, for observing the effect of one or more genetic alterations.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring microorganisms of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given protein or enzyme to function. However, the attenuation of the activity or amount of an enzyme or protein that mimics complete disruption for one reaction can still be sufficient for a separate reaction to continue to function. For example, attenuation of an endogenous enzyme or protein can be sufficient to mimic the complete disruption of the same enzyme or protein for converting succinyl-CoA to succinate or other enzyme or protein of the invention, but the remaining activity or amount of enzyme or protein can still be sufficient to maintain other reactions, such as a reaction that is beneficial for the host microbial organism to survive, reproduce or grow. Attenuation of an enzyme or protein can also be weakening, reducing or diminishing the activity or amount of the enzyme or protein in an amount that is sufficient to reduce carbon flux from succinyl-CoA to succinate through an oxidative TCA cycle of the invention or to weaken, reduce or diminish the activity of other enzymes or proteins of the invention, but do not necessarily mimic complete disruption of the enzyme or protein.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

As used herein, the term "succinyl-CoA converting enzyme" is intended to mean an enzyme that recognizes succinyl-CoA as a substrate and can convert succinyl-CoA into its corresponding acid succinate. Succinyl-CoA converting enzymes include CoA hydrolases, CoA transferases and CoA synthetases. CoA hydrolases are also known in the art as thioesterases and CoA synthetases are also known in the art as CoA acid-thiol ligase. Exemplary CoA hydrolases include acetyl-CoA hydrolase, succinyl-CoA hydrolase and YciA CoA hydrolase. Exemplary CoA transferases include Cat1 CoA transferase, AarC CoA transferase and acetoacetyl-CoA transferase. Exemplary CoA synthetases include succinate-CoA ligase and succinyl-CoA synthetase such as SucCD. Various other exemplary succinyl-CoA converting enzymes are disclosed herein.

As used herein, the term "succinate producing enzyme" when used in reference to an enzyme within a multi-step pathway having a net conversion of succinyl-CoA to succinate is intended to mean an enzyme catalyzing the succinyl-CoA to succinate conversion step within the pathway or an enzyme catalyzing a reaction upstream of the succinyl-CoA to succinate conversion step within the pathway. Accordingly, a succinate producing enzyme, if attenuated, would result in the reduction or elimination of the conversion of succinyl-CoA to succinate within a referenced multi-step pathway. Exemplary multi-step pathways having a net conversion of succinyl-CoA to succinate include arginine degradation, lysine biosynthesis and methionine biosynthesis pathways.

As used herein, the term "excess $CO_2$" is intended to mean $CO_2$ produced via complete glucose oxidation, in the following reaction:

$$C_6H_{12}O_6 + 6O_2 \rightarrow 6CO_2 + 6H_2O$$

In comparison, the term "excess $CO_2$" as it is used herein, is not intended to refer to $CO_2$ that stoichiometrically accompanies the conversion of glucose to a bioderived product of the inventions or byproducts of such metabolically engineered biosynthetic pathway. Using 1,4-butanediol (1,4-BDO) for illustration purposes, for example, the term is not intended to refer to the $CO_2$ produced in the following reaction for the biosynthesis of 1,4-BDO:

$$C_6H_{12}O_6 + \frac{1}{2}O_2 \rightarrow C_4H_{10}O_2 + 2CO_2 + H_2O$$

Excess $CO_2$ percentage refers to the percentage of sugar metabolized to excess $CO_2$.

As used herein, the term "biobased" means a product as described herein that is composed, in whole or in part, of a bioderived compound of the invention. A biobased product is in contrast to a petroleum based product, wherein such a product is derived from or synthesized from petroleum or a petrochemical feedstock.

As used herein, the term "bioderived compound" is intended to mean a target molecule or chemical that is derived from or synthesized by a biological organism. In the context of the present invention, metabolically engineered microbial organisms are used to biosynthetically produce a bioderived compound or intermediate thereof via tricarboxylic acid (TCA) cycle substrates such as succinyl-CoA, α-ketoglutarate (AKG) and acetyl-CoA, including optionally further through acetoacetyl-CoA and/or malonyl-CoA.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase DI activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having reduced carbon flux from succinyl-CoA to succinate through an oxidative TCA cycle or having other metabolic modifications disclosed herein, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionarily related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The invention provides a non-naturally occurring microbial organism having a first attenuation of a succinyl-CoA synthetase or transferase and at least a second attenuation of a succinyl-CoA converting enzyme or a gene encoding a succinate producing enzyme within a multi-step pathway having a net conversion of succinyl-CoA to succinate. The attenuation can be a gene disruption. The succinyl-CoA synthetase or transferase is encoded by a gene set forth in Tables 1, 5, 6, 7, 8, 9, 10 or 11 or an ortholog having at least 70% identity to a gene set forth in Tables 1, 5, 6, 7, 8, 9, 10 or 11.

Yields from microbial organisms metabolically engineered to synthesize carbon-based target products, or bioderived compounds as referred to herein, can be increased by reducing carbon loss into excess $CO_2$ as a metabolic byproduct. One metabolic route that is available for reducing excess $CO_2$ byproduct is the tricarboxylic acid (TCA) cycle. A useful point in the TCA cycle for intervention is at the conversion of succinyl-CoA to succinate that is catalyzed by succinyl-CoA synthetase. Thus, reducing carbon flux from succinyl-CoA to succinate through an oxidative TCA cycle provides useful benefits.

For example, attenuating succinyl-CoA to succinate conversion results in the reduction of excess $CO_2$ byproduct produced by enzymes at subsequent metabolic steps in the TCA cycle and glyoxylate shunt, including, for example, malic enzyme, pyruvate dehydrogenase, pyruvate formate lyase and pyruvate oxidase. Additionally, attenuating succinyl-CoA to succinate conversion also results in the reduction of excess $CO_2$ byproduct by diminution of repeated rounds of carbon flux through the oxidative TCA cycle. Reduction of carbon loss into excess $CO_2$ as a metabolic byproduct increases production yields of carbon-based bioderived compounds because it increases the amount of available carbon for biosynthesis. Greater availability of carbon can increase biosynthetic yields of biobased compounds from all metabolically engineered pathways within a microbial organism, including engineered pathways that are dependent on a TCA cycle substrate as well as those that are independent of a TCA cycle substrate. Where a bioderived compound utilizes a TCA cycle intermediate or substrate upstream of succinate, attenuating the succinyl-CoA to succinate conversion within the TCA cycle also reduces the amount of carbon going into downstream TCA cycle intermediates, thereby increasing the amount of carbon flux into the bioderived target compound.

In one embodiment, microbial organisms of the invention include attenuation of two different succinyl-CoA converting enzymes. One attenuation includes a succinyl-CoA synthetase. The attenuation can be a gene disruption or other genetic alteration described herein or well known in the art that results in diminution of gene expression or gene product activity. Such methods include, for example, altering a promoter, regulatory region or a gene expression regulator of the encoding gene.

Succinyl-CoA synthetases are ubiquitous among microbial organisms. For example, the ADP-forming succinyl-CoA synthetase enzymes catalyze the conversion of succinyl-CoA to succinate within the TCA cycle. Attenuation of a succinyl-CoA synthetase therefore reduces carbon loss into $CO_2$ byproduct and enhances bioderived product yields. Exemplary ADP-forming succinyl-CoA synthetase enzymes are encoded by sucCD of *E. coli* and LSC1 and LSC2 genes of *Saccharomyces cerevisiae* (Buck et al., *Biochemistry* 24:6245-6252 (1985)). Similar enzymes are found in *Mycobacterium tuberculosis*, *Homo sapiens*, *Trypanosoma brucei* and *Trichomonas vaginalis*. Exemplary genes for such ADP-forming succinyl-CoA synthetase enzymes of the invention are summarized below in Table 1.

TABLE 1

Exemplary ADP-forming Succinyl-CoA Synthetases

| Protein | GenBank ID | GI Number | Organism |
| --- | --- | --- | --- |
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |
| sucC | CCE36484.1 | 378544211 | *Mycobacterium tuberculosis* |
| sucD | CCE36485.1 | 378544212 | *Mycobacterium tuberculosis* |
| SUCLA2 | NP_003841.1 | 11321583 | *Homo sapiens* |
| SUCLG1 | CAG33420.1 | 48146395 | *Homo sapiens* |
| Tb927.3.2230 | XP_843817.1 | 72386785 | *Trypanosoma brucei* |
| Tb10.6k15.3250 | XP_822976.1 | 71747842 | *Trypanosoma brucei* |
| a-SCS2 | AAC41558.1 | 538509 | *Trichomonas vaginalis* |
| b-SCS | AAA30326.1 | 162521 | *Trichomonas vaginalis* |

As described further below, succinyl-CoA synthetases other than ADP-forming succinyl-CoA synthetases also can be attenuated in the microbial organisms of the invention as a first attenuation of a succinyl-CoA synthetase. Such succinyl-CoA synthetases other than ADP-forming synthetases are exemplified below in Table 11 and the description related thereto. Accordingly, the invention provides a non-naturally occurring microbial organism wherein a first attenuation includes a succinyl-CoA synthetase. The succinyl-CoA synthetase can be an ADP-forming succinyl-CoA synthetase including, for example, sucCD or it can be a non-ADP-forming succinyl-CoA synthetase, such as a GDP-forming succinyl-CoA synthetase, or it can be another CoA synthetase having succinyl-CoA activity as described herein.

The microbial organisms of the invention also can include a second attenuation of a succinyl-CoA converting enzyme. The second attenuation in a microbial organism of the invention can be a succinyl-CoA converting enzyme other than the succinyl-CoA synthetase corresponding to the first attenuation. Thus, first and second attenuations in a microbial organism of the invention correspond to different proteins or enzymes. The first attenuation is directed to a succinyl-CoA converting enzyme corresponding to a succinyl-CoA synthetase while the second is directed to a different succinyl-CoA converting enzyme. The second, different succinyl-CoA converting enzyme can be a succinyl-CoA synthetase different from the succinyl-CoA synthetase corresponding to the first attenuation or it can be a CoA hydrolase or a CoA transferase as described herein.

While not being bound by theory, in microbial hosts where an enzyme activity is disrupted, one or more endogenous enzymes can compensate for the disrupted enzyme activity. For example, microbial hosts deficient in succinyl-CoA synthetase (SucCD) activity are still able to convert succinyl-CoA to succinate via other endogenous enzymes. The deletion of an endogenous CoA hydrolase, CoA transferase or CoA synthetase enzyme capable of converting succinyl-CoA to succinate can further reduce conversion of succinyl-CoA to succinate, including reduction of complete TCA cycle flux in sucCD-disrupted host organisms, and thereby reduce respiration and excess $CO_2$ byproduct generation.

There are a variety of endogenous enzymes that convert succinyl-CoA to succinate that can be disrupted for reduction of succinate synthesis and reduction of $CO_2$ byproduct production. For example, the single-step conversion of succinyl-CoA to succinate is catalyzed by CoA synthetase, CoA transferase and CoA hydrolase enzymes. The succinyl-CoA to succinate conversion can be the primary physiological function of the enzyme, as is the case with *E. coli* succinyl-CoA synthetase (sucCD), or it may be a side-activity. The encoding genes for any of these enzymes alone or in combination with other succinyl-CoA converting enzymes can be disrupted to attenuate the TCA cycle and reduce the production of $CO_2$ byproduct in a microbial organism of the invention. Exemplary CoA hydrolases, CoA-transferases and CoA synthetases applicable for use as a second attenuation in the microbial organisms of the invention, corresponding to a gene encoding a succinyl-CoA converting enzyme, are described further below. The attenuation can be a gene disruption or other genetic alteration described herein or well known in the art that results in diminution of gene expression or gene productactivity. Such methods include, for example, altering a promoter, regulatory region or a gene expression regulator of the encoding gene.

CoA hydrolase or thioesterase enzymes are in the enzyme class EC 3.1.2, including succinyl-CoA hydrolases, and hydrolyze acyl-CoA molecules to their corresponding acids. Such CoA hydrolases can be included in a microbial organism of the invention as a second attenuation of a gene encoding a succinyl-CoA converting enzyme.

Several CoA hydrolases are active on succinyl-CoA including acetyl-CoA hydrolase (EC 3.1.2.1), palmitoyl-CoA hydrolase (EC 3.1.2.2), succinyl-CoA hydrolase (EC 3.1.2.3) and acyl-CoA hydrolase (EC 3.1.2.20). Other acetyl-CoA hydrolases that also convert succinyl-CoA to succinate include acot12 from *Rattus norvegicus* brain (Robinson et al., *Biochem. Biophys. Res. Commun.* 71:959-965 (1976)) and enzymes from *Ovis aries* and *Pisum sativum* (Zeiher et al., *Plant. Physiol.* 94:20-27 (1990); Snoswell and Tubbs, *Biochem J* 171(2):299-303 (1978)). The human peroxisomal acyl-CoA thioesterase ACOT4 catalyzes the hydrolysis of succinyl-CoA (Hunt et al, *FASEB J* 20:1855-64 (2006); Westin et al, *J Biol Chem* 280: 38125-32 (2005)). Yet another enzyme with succinyl-CoA hydrolase activity is the PA5202 enzyme of *Pseudomonas aeruginosa* (Gonzalez et al, *Biochem J* 445-455 (2012)). Exemplary CoA hydrolases are summarized below in Table 2.

TABLE 2

Exemplary CoA Hydrolases

| Gene name | GenBank Accession # | GI# | Organism |
| --- | --- | --- | --- |
| tesB | NP_414986 | 16128437 | *Escherichia coli* |
| acot12 | NP_570103.1 | 18543355 | *Rattus norvegicus* |
| ACOT4 | Q3I5F7 | 121942509 | *Homo sapiens* |
| ACOT4 | EDL02757.1 | 148670810 | *Mus musculus* |
| PA5202 | NP_253889.1 | 15600395 | *Pseudomonas aeruginosa* |

The yciA gene encodes a CoA hydrolase and has been shown to hydrolyze a range of acyl-CoA substrates including acetyl-CoA, butyryl-CoA, decanoyl-CoA and palmitoyl-CoA and succinyl-CoA as described herein (see also, for example, Zhuang et al, *Biochem* 47: 2789-96 (2008)). In one embodiment of the invention, microbial organisms with attenuation of the protein encoded by yciA exhibit a decrease of succinyl-CoA to succinate conversion within the TCA cycle, demonstrating that YciA has succinyl-CoA activity. Exemplary YciA enzymes having succinyl-CoA hydrolase activity include yciA of *E. coli* and *Haemophilus influenza*. Exemplary succinyl-CoA hydrolases are summarized below in Table 3.

TABLE 3

Exemplary CoA Hydrolases

| Gene name | GenBank Accession # | GI# | Organism |
| --- | --- | --- | --- |
| yciA | YP_005828226.1 | 386264733 | *Haemophilus influenza* |
| yciA | NP_415769.1 | 16129214 | *Escherichia coli* |

As described further below, the succinyl-CoA hydrolase activity of YciA CoA hydrolase was observed to substantially decrease conversion of succinyl-CoA to succinate in organisms also having attenuation of a second succinyl-CoA converting enzyme. As disclosed herein, although a gene disruption of the gene encoding the TCA cycle enzyme succinyl-CoA synthetase (sucCD) that converts succinyl-CoA to succinate resulted in decreased succinate production, a further attenuation of the protein encoded by yciA resulted in a substantial and non-additive reduction in succinate production from succinyl-CoA. In contrast, attenuations of other hydrolases also having activity for acetyl-CoA have yielded different results.

Enzymes that react with a broad range of acyl-CoA substrates can also be active on succinyl-CoA. For example, in addition to reacting with succinyl-CoA, the enzyme encoded by acot12 from *Rattus norvegicus* brain (Robinson et al., *Biochem. Biophys. Res. Commun.* 71:959-965 (1976)) also can react with butyryl-CoA, hexanoyl-CoA and malonyl-CoA, indicating that CoA hydrolases having activity for medium and/or long chain thioesters can be active on succinyl-CoA. In this regards, the human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)). The closest *E. coli* homolog to this enzyme, tesB, can also hydrolyze a range of medium- and long chain CoA thioesters (Naggert et al., *J Biol Chem* 266:11044-11050 (1991)). A similar enzyme has also been characterized in the rat liver (Deana R., *Biochem Int* 26:767-773 (1992)). Additional enzymes with CoA hydrolase activity in *E. coli* include bioH, entH, fadM, frsA, paaI, tesA, tesC, ybaW, ybfF ybhC, ydiI, yeiG, yigI, yiiD, yjfP, yjjU, ypfH, yqiA, ybgC and ybdB (Kuznetsova, et al., *FEMS Microbiol Rev,* 2005, 29(2):263-279; Song et al., *J Biol Chem,* 2006, 281(16):11028-38; Guo et al., *Biochemistry* 48:1712-1722 (2009)). Most of the above *E. coli* enzymes were identified in a high-throughput screen using palmitoyl-CoA as the acyl-CoA substrate (Kuznetsova et al, supra).

The acetyl-CoA hydrolase, ACH1, from *S. cerevisiae* represents another candidate hydrolase (Buu et al., *J. Biol. Chem.* 278:17203-17209 (2003)). Additional enzymes with acyl-CoA hydrolase activity include the palmitoyl-CoA hydrolase of *Mycobacterium tuberculosis* (Wang et al., *Chem. Biol.* 14:543-551 (2007)). Another exemplary CoA hydrolase is the glutaconate CoA-transferase from *Acidaminococcus fermentans.* This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). Exemplary CoA hydrolases are summarized below in Table 4. Those CoA hydrolases having succinyl-CoA hydrolase activity are applicable as a succinyl-CoA converting enzyme of the invention and can therefore be targeted for attenuation. Additional CoA hydrolase enzymes can be identified by sequence similarity to any of the CoA hydrolase candidates described herein.

TABLE 4

Exemplary CoA Hydrolases

| Gene name | GenBank Accession # | GI# | Organism |
|---|---|---|---|
| acot8 | CAA15502 | 3191970 | *Homo sapiens* |
| acot8 | NP_570112 | 51036669 | *Rattus norvegicus* |
| bioH | P13001.1 | 115011 | *Escherichia coli* |
| entH | AAC73698.1 | 1786813 | *Escherichia coli* |
| fadM | NP_414977.1 | 16128428 | *Escherichia coli* |
| frsA | P04335.2 | 17865775 | *Escherichia coli* |
| paaI | NP_415914 | 16129357 | *Escherichia coli* |
| tesA | NP_415027 | 16128478 | *Escherichia coli* |
| tesC | NP_414977.1 | 16128428 | *Escherichia coli* |
| ybaW | NP_414977.1 | 16128428 | *Escherichia coli* |
| ybfF | NP_415212.1 | 16128662 | *Escherichia coli* |
| ybhC | P46130.2 | 2507166 | *Escherichia coli* |
| ydiI | NP_416201.1 | 16129642 | *Escherichia coli* |
| yeiG | P33018.1 | 465595 | *Escherichia coli* |
| yigI | P0ADP2.1 | 83288116 | *Escherichia coli* |
| yiiD | P0ADQ2.1 | 83288127 | *Escherichia coli* |
| yifP | P39298.1 | 732024 | *Escherichia coli* |
| yjjU | P39407.1 | 732119 | *Escherichia coli* |
| ypfH | NP_416968.2 | 90111441 | *Escherichia coli* |
| ygiA | Q79CP2.1 | 81704000 | *Escherichia coli* |
| ybgC | NP_415264 | 16128711 | *Escherichia coli* |
| ybdB | NP_415129 | 16128580 | *Escherichia coli* |
| ACH1 | NP_009538 | 6319456 | *Saccharomyces cerevisiae* |
| Rv0098 | NP_214612.1 | 15607240 | *Mycobacterium tuberculosis* |
| gctA | CAA57199.1 | 559392 | *Acidaminococcus fermentans* |
| gctB | CAA57200.1 | 559393 | *Acidaminococcus fermentans* |
| gctA | ACJ24333.1 | 212292816 | *Clostridium symbiosum* |
| gctB | ACJ24326.1 | 212292808 | *Clostridium symbiosum* |
| gctA | NP_603109.1 | 19703547 | *Fusobacterium nucleatum* |
| gctB | NP_603110.1 | 19703548 | *Fusobacterium nucleatum* |

CoA transferases, including succinyl-CoA transferases, catalyze the reversible transfer of a CoA moiety from an acyl-CoA to a carboxylic acid acceptor. CoA transferase enzymes in the EC classes listed below in Table 5 have been shown to catalyze the conversion of succinyl-CoA to succinate.

TABLE 5

Exemplary CoA Transferases

| EC number | Enzyme name |
|---|---|
| 2.8.3.2 | oxalate CoA-transferase |
| 2.8.3.5 | 3-oxoacid CoA-transferase |
| 2.8.3.6 | 3-oxoadipate CoA-transferase |
| 2.8.3.7 | succinate-citramalate CoA-transferase |
| 2.8.3.8 | acetate CoA-transferase |
| 2.8.3.13 | Succinate:hydroxymethylglutarate CoA transferase |
| 2.8.3.15 | Succinyl-CoA:benzylsuccinate CoA transferase |
| 2.8.3.16 | Formyl-CoA transferase |

For example, the gene products of cat1, cat2, and cat3 of *Clostridium kluyveri* have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *J Bacteriol.* 178:871-880 (1996)). Succinyl-CoA transferase activity is also present in *Trichomonas vaginalis, Trypanosoma brucei, Clostridium aminobutyricum* and *Porphyromonas gingivalis* (Riviere et al., *J. Biol. Chem.* 279:45337-45346 (2004); van Grinsven et al., *J. Biol. Chem.* 283:1411-1418 (2008)). *Acetobacter aceti* uses a succinyl-CoA:acetate CoA transferase to complete its unusual TCA cycle (Mullins et al *J Bacteriol* 190:4933-40 (2008)). Exemplary succinyl-CoA transferases are summarized below in Table 6.

TABLE 6

Exemplary CoA Transferases

| Protein | GenBank ID | GI Number | Organism |
|---|---|---|---|
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| ASCT | XP_001330176 | 123975034 | *Trichomonas vaginalis* |
| Tb11.02.0290 | XP_828352 | 71754875 | *Trypanosoma brucei* |
| cat2 | CAB60036.1 | 6249316 | *Clostridium aminobutyricum* |
| cat2 | NP_906037.1 | 34541558 | *Porphyromonas gingivalis* W83 |
| AarC | AGG68324.1 | 459463669 | *Acetobacter aceti* |

Other transferases also can exhibit succinyl-CoA transferase activity and are applicable for targeting as an attenuation of a succinyl-CoA converting enzyme of the invention. For example, a fatty acyl-CoA transferase that utilizes acetyl-CoA as the CoA donor is acetoacetyl-CoA transferase, encoded by the *E. coli* atoA (alpha subunit) and atoD (beta subunit) genes (Korolev et al., *Acta Crystallogr. D. Biol. Crystallogr.* 58:2116-2121 (2002); Vanderwinkel et al., 33:902-908 (1968)). This enzyme has a broad substrate range on substrates of chain length C3-C6 (Sramek et al., *Arch Biochem Biophys* 171:14-26 (1975)) and has been shown to transfer the CoA moiety to acetate from a variety of branched and linear 3-oxo and acyl-CoA substrates (Matthies et al., *Appl Environ. Microbiol* 58:1435-1439 (1992); (Vanderwinkel et al., *Biochem. Biophys. Res. Commun.* 33:902-908 (1968; Vanderwinkel et al., *Biochem. Biophys. Res. Commun.* 33:902-908 (1968)). Similar enzymes exist in *Corynebacterium glutamicum* ATCC 13032 (Duncan et al., 68:5186-5190 (2002)), *Clostridium acetobutylicum* (Cary et al., *Appl Environ Microbiol* 56:1576-1583 (1990); Wiesenborn et al., *Appl Environ Microbiol* 55:323-329 (1989)), and *Clostridium saccharoperbutylacetonicum* (Kosaka et al., *Biosci. Biotechnol Biochem.* 71:58-68 (2007)). These exemplary CoA transferases are applicable for attenuation as a succinyl-CoA converting enzyme of the invention. Exemplary CoA transferases are summarized below in Table 7.

TABLE 7

Exemplary CoA Transferases

| Gene | GI # | Accession No. | Organism |
| --- | --- | --- | --- |
| atoA | 2492994 | P76459.1 | Escherichia coli |
| atoD | 2492990 | P76458.1 | Escherichia coli |
| actA | 62391407 | YP_226809.1 | Corynebacterium glutamicum |
| cg0592 | 62389399 | YP_224801.1 | Corynebacterium glutamicum |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae* serovar, and *Yersinia intermedia* ATCC 29909. These proteins are identified below. The formyl-CoA transferase enzymes of *E. coli* (yfdW) and *Oxalobacter formigenes* (frc) can use succinyl-CoA as a CoA donor (Sidhu et al, *J Bacteriol* 3378-81 (1997); Toyota et al, *J Bacteriol* 190:7 (2008)). Other CoA transferases in *E. coli* that can catalyze the conversion of succinyl-CoA to succinate include yfdW, yrdE, caiB and ydiF. Such additional, exemplary CoA transferases are applicable for attenuation as a succinyl-CoA converting enzyme of the invention. Exemplary CoA transferases are summarized below in Table 8.

TABLE 8

Exemplary CoA Transferases

| Protein | GenBank ID | GI Number | Organism |
| --- | --- | --- | --- |
| ygfH | NP_417395.1 | 16130821 | Escherichia coli |
| CIT292_04485 | ZP_03838384.1 | 227334728 | Citrobacter youngae |
| SARI_04582 | YP_001573497.1 | 161506385 | Salmonella enterica |
| yinte0001_14430 | ZP_04635364.1 | 238791727 | Yersinia intermedia |
| frc | O06644 | 21542067 | Oxalobacter formigenes |
| yfdW | NP_416875.1 | 16130306 | Escherichia coli |
| yfdE | NP_416872.4 | 162135906 | Escherichia coli |
| caiB | NP_414580.1 | 16128032 | Escherichia coli |
| ydiF | NP_416209.1 | 16129650 | Escherichia coli |

Succinyl-CoA:3:oxoacid-CoA transferase (SCOT) enzymes also catalyze the conversion of succinyl-CoA to succinate. Enzymes in this class are encoded by pcaI and pcaJ in *Pseudomonas putida* (Kaschabek et al., *J Bacteriol.* 184:207-215 (2002)). Similar enzymes are found in *Acinetobacter* sp. ADP1 (Kowalchuk et al., *Gene* 146:23-30 (1994)), *Streptomyces coelicolor* and *Pseudomonas knackmussii* (formerly sp. B13) (Gobel et al., *J Bacteriol.* 184: 216-223 (2002); Kaschabek et al., *J Bacteriol.* 184:207-215 (2002)). Additional exemplary succinyl-CoA:3:oxoacid-CoA transferases have been characterized in *Helicobacter pylori* (Corthesy-Theulaz et al., *J Biol. Chem.* 272:25659-25667 (1997)), *Bacillus subtilis* (Stols et al., *Protein Expr. Purif* 53:396-403 (2007)) *Sus scrofa* and *Homo sapiens* (Fukao, T., et al., *Genomics* 68:144-151 (2000); Tanaka, H., et al., *Mol Hum Reprod* 8:16-23 (2002)). Accordingly, these exemplary CoA transferases are applicable for attenuation as a succinyl-CoA converting enzyme of the invention. Exemplary CoA transferases are summarized below in Table 9.

TABLE 9

Exemplary CoA Transferases

| Gene | GI # | Accession No. | Organism |
| --- | --- | --- | --- |
| pcaI | 24985644 | AAN69545.1 | Pseudomonas putida |
| pcaJ | 26990657 | NP_746082.1 | Pseudomonas putida |
| pcaI | 50084858 | YP_046368.1 | Acinetobacter sp. ADP1 |
| pcaJ | 141776 | AAC37147.1 | Acinetobacter sp. ADP1 |
| pcaI | 21224997 | NP_630776.1 | Streptomyces coelicolor |
| pcaJ | 21224996 | NP_630775.1 | Streptomyces coelicolor |
| catI | 75404583 | Q8VPF3 | Pseudomonas knackmussii |
| catJ | 75404582 | Q8VPF2 | Pseudomonas knackmussii |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |
| OXCT1 | NP_000427 | 4557817 | Homo sapiens |
| OXCT2 | NP_071403 | 11545841 | Homo sapiens |
| SCOT | Q29551.2 | 395398464 | Homo sapiens |

Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. For example, an enzyme from *Roseburia* sp. A2-183 was shown to have butyryl-CoA:acetate:CoA transferase and propionyl-CoA:acetate:CoA transferase activity (Charrier et al., *Microbiology* 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Bucket, *FEBS Letters*, 171 (1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae* serovar, and *Yersinia intermedia* ATCC 29909. Those CoA transferases having succinyl-CoA transferase activity are applicable as a succinyl-CoA converting enzyme of the invention and can therefore be targeted for attenuation. Exemplary CoA transferases are summarized below in Table 10.

TABLE 10

Exemplary CoA Transferases

| Protein | GenBank ID | GI Number | Organism |
| --- | --- | --- | --- |
| Ach1 | AAX19660.1 | 60396828 | Roseburia sp. A2-183 |
| ROSINTL182_07121 | ZP_04743841.2 | 257413684 | Roseburia intestinalis |
| ROSEINA2194_03642 | ZP_03755203.1 | 225377982 | Roseburia inulinivorans |
| EUBREC_3075 | YP_002938937.1 | 238925420 | Eubacterium rectale |

TABLE 10-continued

Exemplary CoA Transferases

| Protein | GenBank ID | GI Number | Organism |
| --- | --- | --- | --- |
| pct | CAB77207.1 | 7242549 | Clostridium propionicum |
| NT01CX_2372 | YP_878445.1 | 118444712 | Clostridium novyi NT |
| Cbei_4543 | YP_001311608.1 | 150019354 | Clostridium beijerinckii |
| CBC_A0889 | ZP_02621218.1 | 168186583 | Clostridium botulinum |

CoA acid-thiol ligase or CoA synthetase occur in the 6.2.1 class of enzymes, including succinyl-CoA synthetases, and catalyze the conversion of acyl-CoA substrates to their acid products. As described previously, a gene encoding a CoA synthetase can be utilized as either a first attenuation corresponding to a succinyl-CoA synthetase or second attenuation corresponding to a succinyl-CoA converting enzyme in a microbial organism of the invention. Exemplary CoA synthetases applicable for attenuation in a microbial organism of the invention are described (see Table 1 and the corresponding description). Other exemplary CoA synthetases applicable for attenuation in a microbial organism of the invention are described below.

CoA synthetases that convert ATP or GTP to ADP or GDP are reversible and can catalyze the conversion of succinyl-CoA to succinate. AMP-forming enzymes catalyze the activation of an acid to an acyl-CoA. CoA synthetase enzymes for converting succinyl-CoA to succinate include succinate-CoA ligase (GDP forming, EC 6.2.1.4), succinate-CoA ligase (ADP forming, EC 6.2.1.5), and acetate-CoA ligase (ADP forming, EC 6.2.1.13).

Another applicable CoA synthetase for attenuation as a succinyl-CoA synthetase or as a succinyl-CoA converting enzyme includes ADP-forming acetyl-CoA synthetase (ACD, EC 6.2.1.13). This CoA synthetase is an enzyme that couples the conversion of acyl-CoA esters to their corresponding acids with the concomitant synthesis of ATP.

ADP-forming succinyl-CoA synthetase enzymes are exemplified herein (see Table 1 and the corresponding description). Briefly, these succinyl-CoA synthetases are encoded by sucCD of *E. coli* and LSC1 and LSC2 genes of *Saccharomyces cerevisiae* and similar enzymes are found in *Mycobacterium tuberculosis*, *Homo sapiens*, *Trypanosoma brucei* and *Trichomonas vaginalis* (Table 1). These CoA synthetases are applicable for attenuation either as a succinyl-CoA synthetase or as a succinyl-CoA converting enzyme of the invention.

CoA synthetase enzymes with broad substrate specificity can also be active on succinyl-CoA. For example, ACD I from *Archaeoglobus fulgidus*, encoded by AF1211, has been shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range (Musfeldt and Schonheit, *J Bacteriol.* 184:636-644 (2002)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, *Arch Microbiol* 182:277-287 (2004)). Directed evolution or engineering can be used to modify this enzyme to operate at the physiological temperature of the host organism. The enzyme from *Haloarcula marismortui* (annotated as a succinyl-CoA synthetase) accepts, for example, propionate, butyrate, and branched-chain acids (isovalerate and isobutyrate) as substrates, and was shown to operate in the forward and reverse directions (Brasen et al., *Arch Microbiol* 182:277-287 (2004)). The enzymes from *A. fulgidus*, *H. marismortui* and *P. aerophilum* have all been cloned, functionally expressed, and characterized in *E. coli* (Brasen and Schonheit, supra; Musfeldt and Schonheit, *J Bacteriol.* 184:636-644 (2002)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)). Exemplary CoA synthetases are summarized below in Table 11. Those CoA synthetases having succinyl-CoA synthetase activity are applicable as either a succinyl-CoA synthetase or succinyl-CoA converting enzyme of the invention and can therefore be targeted for attenuation.

TABLE 11

Exemplary CoA Synthetases

| Protein | GenBank ID | GI Number | Organism |
| --- | --- | --- | --- |
| scs | YP_135572.1 | 55377722 | Haloarcula marismortui |
| AF1211 | NP_070039.1 | 11498810 | Archaeoglobus fulgidus |
| AF1983 | NP_070807.1 | 11499565 | Archaeoglobus fulgidus |
| PAE3250 | NP_560604.1 | 18313937 | Pyrobaculum aerophilum str. IM2 |
| paaF | AAC24333.2 | 22711873 | Pseudomonas putida |
| matB | AAC83455.1 | 3982573 | Rhizobium leguminosarum |

Multi-step metabolic pathways other than the TCA cycle also can be targeted for attenuation of a succinyl-CoA converting enzyme to result in reduced carbon flux from succinyl-CoA to succinate. For example, while CoA hydrolases, transferases and synthetases convert succinyl-CoA to succinate in a single enzymatic step, those skilled in the art will understand that other multi-enzyme metabolic pathways also can catalyze this net reaction. Exemplary multi-step pathways that can be used for attenuation of a succinate producing enzyme within a multi-step pathway having a net conversion of succinyl-CoA to succinate include: (1) arginine degradation, (2) lysine biosynthesis, and (3) methionine biosynthesis pathways. The net stoichiometry of the succinyl-CoA to succinate reaction is shown in Table 12 below.

TABLE 12

Net Stoichiometry of Succinyl-CoA to Succinate in Multi-Step Pathways

| Genes in E. coli | Pathway | Net reaction | Number of Reactions |
|---|---|---|---|
| astABCDE | Arginine degradation | Arg + Suc-CoA + AKG + 4H$_2$O + NAD → Succ + 2 Glutamate + CO$_2$ + NADH + CoA | 5 |
| dapD-argD-dapE | Lysine biosynthesis | THD + Suc-CoA + Glutamate + 2H$_2$O → DAP + succinate + AKG + CoA | 3 |
| metAB | Methionine biosynthesis | Homoserine + Suc-CoA + Cysteine → Cystathione + Succ + Homocys + Pyr + CoA | 2 |

As with all other attenuations disclosed herein, the attention of a succinate producing enzyme within a multi-step pathway can be a gene disruption or other genetic alteration described herein or well known in the art that results in diminution of gene expression or gene product activity. Such methods include, for example, altering a promoter, regulatory region or a gene expression regulator of the encoding gene.

The succinate producing enzymes within the above exemplary multi-step pathways include the enzymes that catalyze the succinyl-CoA to succinate conversion step within each pathway as well as any of the enzymes catalyzing a reaction upstream of the succinyl-CoA to succinate conversion step within the pathway that would prohibit the downstream formation of succinate. Given the teachings and guidance provided herein, those skilled in the art will understand that enzymes within numerous other multi-step pathways having a net conversion of succinyl-CoA to succinate also can be targeted for attenuations to reduce carbon flux from succinyl-CoA to succinate. Such enzymes include, for example, those pathway enzymes that convert succinyl-CoA to succinate as well as those enzymes upstream of the succinyl-CoA to succinate conversion step that, if attenuated, result in the loss or elimination of succinate downstream in the multi-step pathway.

A non-naturally occurring microbial organism of the invention includes at least a second attenuation of a gene encoding succinyl-CoA converting enzyme or a gene encoding a succinate producing enzyme within a multi-step pathway having a net conversion of succinyl-CoA to succinate. Accordingly, in this embodiment, the non-naturally occurring microbial organism can include more than one second attenuation of a succinyl-CoA converting enzyme or of a succinate producing enzyme. The inclusion of two or more second attenuations can further reduce carbon flux through an oxidative TCA cycle, thereby additionally reducing CO$_2$ byproduct formation. Thus, a microbial organism of the invention can include 1, 2, 3, 4, 5, 6, 7, 8, 9 or 10 or more second attenuations of a gene encoding a succinyl-CoA converting enzyme or encoding a succinate producing enzyme within a multi-step pathway having a net conversion of succinyl-CoA to succinate. Given the teachings and guidance provided herein, those skilled in the art will understand how many and which second attenuations are useful for a particular application.

Thus, the invention further provides a non-naturally occurring microbial organism having a first and at least a second attenuation. The first attenuation can be a succinyl-CoA synthetase and the succinyl-CoA synthetase can be, for example, encoded by sucCD. The first attenuation also can be a succinyl-CoA transferase. The first attenuation also can be a succinyl-CoA synthetase encoded by a gene set forth in Tables 1 or 11. The first attenuation also can be a succinyl-CoA synthetase or succinyl-CoA transferase encoded by a gene set forth in Tables 1, 5, 6, 7, 8, 9, 10 or 11. The at least second attenuation can be a succinyl-CoA converting enzyme or a succinate producing enzyme within a multi-step pathway having a net conversion of succinyl-CoA to succinate. The at least second attenuation can be a CoA hydrolase, CoA transferase or CoA synthetase encoded by a gene set forth in Tables 1-11 or the at least second attenuation can be one or more succinate producing enzymes set forth in Table 12. The at least second attenuation can be YciA CoA hydrolase encoded by the gene yciA. The at least second attenuation can be two or more, including several to many succinyl-CoA converting enzymes or a succinate producing enzyme.

The invention also provides a non-naturally occurring microbial organism having a first attenuation of a gene encoding a succinyl-CoA synthetase and at least a second attenuation of gene encoding succinyl-CoA converting enzyme or a succinate producing enzyme within a multi-step pathway, wherein the level of succinate production via an oxidative tricarboxylic acid (TCA) pathway is reduced by 25% or more compared to a microbial organism absent of the second attenuation. It is understood by those skilled in the art that a microbial organism absent of the second attenuation refers to a microbial organism that lacks the genetic modification of the second attenuation, and the activity can be compared to such an organism lacking the genetic modification of the second attenuation.

As described previously, attenuation of both a succinyl-CoA synthetase and at least a second gene encoding, for example, a succinyl-CoA converting enzyme, results in a significant and non-additive decrease in succinate production via an oxidative TCA pathway compared to an organism having attenuation of a succinyl-CoA synthetase alone. The reduction in succinate production via oxidative TCA can be, for example, 20% or more, including a reduction of 25%, 30%, 35%, 40%, 45%, 50%, 55%, 60%, 65%, 70%, 75%, 80% or more. Accordingly, a microbial organism of the invention can have a level of succinyl-CoA to succinate activity reduced by 25% or more compared to a microbial organism absent of a second attenuation. The succinyl-CoA to succinate activity can be reduced, for example, 20% or more, including a reduction of 25%, 30%, 35%, 40%, 45%, 50%, 55%, 60%, 65%, 70%, 75%, 80% or more. Further, a microbial organism of the invention can have a level of $^{13}$C flux from succinyl-CoA to succinate reduced by 25% or more compared to a microbial organism absent of said second attenuation. The $^{13}$C flux from succinyl-CoA to succinate can be reduced, for example, 20% or more, including a reduction of 25%, 30%, 35%, 40%, 45%, 50%, 55%, 60%, 65%, 70%, 75%, 80% or more.

The disruption of both a succinyl-CoA synthetase and at least a second gene encoding, for example, a succinyl-CoA converting enzyme also results in a reduction of excess CO$_2$ produced via oxidative TCA compared to an organism having attenuation of a succinyl-CoA synthetase alone. The reduction in excess CO$_2$ production via oxidative TCA can be, for example, 10% or more compared to a microbial organism absent of a second attenuation. As described previously, a decrease in excess CO$_2$ facilitates greater carbon flux into the production of bioderived compounds and, therefore, greater yields of such bioderived compounds. Accordingly, a reduction in excess CO$_2$ production via oxidative TCA can be, for example, 15% or more, including a reduction of 20%, 25%, 30%, 35%, 40%, 45%, 50%, 55%, 60%, 65%, 70%, 75%, 80% or more.

In like fashion, the disruption of both a succinyl-CoA synthetase and at least a second gene encoding, for example, a succinyl-CoA converting enzyme additionally results in decreased oxygen utilization per cell compared to an organism having a attenuation of a succinyl-CoA synthetase alone. The reduction in oxygen utilization per cell can be, for example, 10% or more compared to a microbial organism absent of a second attenuation. Decreased oxygen utilization of the microbial organism is useful for bioderived compound production in micro-anaerobic and anaerobic culture conditions. Accordingly, a reduction in oxygen ($O_2$) utilization per cell can be, for example, 15% or more, including a reduction of 20%, 25%, 30%, 35%, 40%, 45%, 50%, 55%, 60%, 65%, 70%, 75%, 80% or more.

Accordingly, the invention also provides a non-naturally occurring microbial organism having a first attenuation of a succinyl-CoA synthetase and at least a second attenuation of succinyl-CoA converting enzyme or a succinate producing enzyme within a multi-step pathway wherein a level of excess $CO_2$ via oxidative TCA is reduced by 10% or more compared to a microbial organism absent of the second attenuation (i.e., compared to a parental microbial organism having a first attenuation of a succinyl-CoA synthetase). Additionally, the level of oxygen ($O_2$) utilization per cell is reduced by 10% or more compared to a microbial organism absent of the second attenuation (i.e., compared to a parental microbial organism having a first attenuation of a succinyl-CoA synthetase).

The invention additionally provides a non-naturally occurring microbial organism having increased expression of a pyridine nucleotide transhydrogenase (NAD(P) transhydrogenase). The increased expression can be alone or in combination with any of the genetic alterations described herein including, for example, increasing expression of a NAD(P) transhydrogenase in a non-naturally occurring microbial organism having a first attenuation of a succinyl-CoA synthetase and a second attenuation of a succinyl-CoA converting enzyme or a succinate producing enzyme as described herein. Thus, the invention also provides a non-naturally occurring microbial organism having a first attenuation of a succinyl-CoA synthetase and a second attenuation of a succinyl-CoA converting enzyme or a succinate producing enzyme and further including increased expression of a NAD(P) transhydrogenase. The increased expression can be expression of an exogenous nucleic acid encoding NAD(P) transhydrogenase. The increased expression also can include, for example, up regulating the expression of the transhydrogenase encoding gene or by removing negative regulation of a gene encoding the transhydrogenase. Examples of up regulation include, for example, modifying the promoter to make it stronger, increasing the strength of ribosomal binding site(s), substituting a stronger promoter and/or optionally increasing the copy number of the gene. Examples of removing negative regulation include modifying the gene regulatory cis elements or trans regulatory elements. The pyridine nucleotide transhydrogenase can be a proton-translocating transhydrogenase.

In this regard, the non-naturally occurring microbial organisms of the invention can further include one or more genetic modifications that increase expression of an NAD(P) transhydrogenase in the microbial organism. An NAD(P) transhydrogenase catalyzes the transfer of reducing equivalents between NAD(H) and NADP(H), coupled to the translocation of protons across a membrane (Jackson, *FEBS Letters* 545:18 (2003)). In this embodiment, the production of excess $CO_2$ is further reduced by reducing carbon flux from succinyl-CoA to succinate through an oxidative TCA cycle as well as through the pentose phosphate pathway.

One NAD(P) transhydrogenase useful for reducing the production of excess $CO_2$ by increasing its expression in a host microbial organism of the invention can be the NAD(P) transhydrogenase PntAB or its homologs. Expression of PntAB or other NAD(P) transhydrogenases can occur by, for example, overexpression of an endogenous encoding gene and/or expression of an exogenous encoding nucleic acid. As described further below, various other methods also are available for increasing expression of either an endogenous or exogenous nucleic acid including, for example, incorporating stronger promoters and/or positive regulatory elements of either the endogenous encoding nucleic acids, exogenous encoding nucleic acids, or both. Those skilled in the art will appreciate that some or all of such methods can be used, alone or in combination, to increase expression of an encoding nucleic acid. The nucleotide and amino acid sequences for pntA and pntB from *Escherichia coli* can be found described in Clarke et al., 158:647-653 (1986).

Further provided is a non-naturally occurring microbial organism having attenuation of a TCA cycle enzyme. The attenuation of a TCA cycle enzyme can be alone or in combination with any of the genetic alterations described herein including, for example, attenuation of an endogenous nucleic acid encoding a TCA cycle enzyme in a non-naturally occurring microbial organism having a first attenuation of a succinyl-CoA synthetase and a second attenuation of a succinyl-CoA converting enzyme or a succinate producing enzyme as described herein. In this latter example, the attenuation of a TCA cycle enzyme is different from the first and second attenuations. The attenuation can be of a succinyl-CoA synthetase within the TCA cycle. For example, the attenuation can be, for example, succinic dehydrogenase, fumarase and malate dehydrogenase. The attenuation can be a gene disruption or other genetic alteration described herein or well known in the art that results in diminution of gene expression or gene product activity. Such methods include, for example, altering a promoter, regulatory region or a gene expression regulator of the encoding gene.

The genetic alterations described herein are applicable for microbial production of bioderived compounds initiating from any metabolic intermediate including, for example, substrates or intermediates within the TCA cycle as well as substrates or intermediates within other metabolic pathways. Thus, the genetic alterations described herein are applicable for reduction of succinate production from succinyl-CoA, reduction of excess $CO_2$ and reduction of $O_2$ utilization as well for increasing ATP availability as described further below. Described in reference to the production of a bioderived compound from a TCA cycle intermediate or a TCA cycle substrate, for example, the attenuation of a succinyl-CoA synthetase still allows use of TCA intermediates and substrates upstream from succinyl-CoA to be utilized in the production of a bioderived compound. Attenuation of a succinyl-CoA synthetase, alone or in combination with a second attenuation succinyl-CoA converting enzyme or a succinate producing enzyme as described herein reduces the carbon flux into downstream TCA cycle intermediates and increases the carbon flux available for bioderived compound biosynthesis. Exemplary TCA cycle intermediates useful for bioderived compound synthesis include α-ketoglutarate (AKG) and succinyl-CoA. An exemplary TCA cycle substrate includes acetyl-CoA.

As used herein, a "TCA cycle intermediate" refers to one of the nine TCA cycle substrates or products used to generate energy through the oxidation of acetate. These nine substrates are citrate, cis-aconitate, d-isocitrate, α-ketoglutarate, succinyl-CoA, succinate, fumarate, malate and oxaloacetate. A "TCA cycle substrate" as used herein refers to a substrate used in the TCA cycle other than the above nine compounds. For example, acetyl-CoA is a TCA cycle substrate because it combines with oxaloacetate to form citrate.

Bioderived compounds of the invention include, but are not limited to, alcohols, glycols, organic acids, alkenes, dienes, organic amines, organic aldehydes, vitamins, nutraceuticals and pharmaceuticals. Specific bioderived compounds within these categories of bioderived compounds that are applicable to be synthesized using a microbial organism of the invention metabolically engineered to biosynthesize bioderived compounds include, for example, 4-hydroxybutyrate (4HB), 1,4-butanediol (1,4-BDO), 1,3-butanediol (1,3-BDO), polyhydroxylbutanoate (PHB), butadiene, adipate, 6-aminocaproate, caprolactam, methacrylic acid, isopropanol, long chain alcohols, hexamethylenediamene, methyl methacrylate, butanol, 3-butene-1-ol, 3-butene-2-ol and crotyl-alcohol. Thus, the invention additionally provides a non-naturally occurring microbial organism having a metabolically engineered pathway for producing a bioderived compound from a TCA cycle substrate. The bioderived compound can be 4HB, 1,4-BDO, 1,3-BDO, PHB, butadiene, adipate, 6-aminocaproate, caprolactam, methacrylic acid, isopropanol, long chain alcohols, hexamethylenediamene, methyl methacrylate, butanol, 3-butene-1-ol, 3-butene-2-ol and crotyl-alcohol. The microbial organism can comprise the metabolically engineered pathway optionally in combination with any of the genetic alterations described herein including, for example, a metabolically engineered pathway for producing a bioderived compound from a TCA cycle substrate in a non-naturally occurring microbial organism having a first attenuation of a succinyl-CoA synthetase and a second attenuation of a succinyl-CoA converting enzyme or a succinate producing enzyme as described previously.

Other bioderived compounds within the above categories that also are applicable to be synthesized using a microbial organism of the invention are exemplified below. For examples, alcohols of the invention, including biofuel alcohols, include primary alcohols, secondary alcohols, diols and triols, preferably having C3 to C10 carbon atoms. Alcohols include n-propanol and isopropanol. Biofuel alcohols are preferably C3-C10 and include 1-Propanol, Isopropanol, 1-Butanol, Isobutanol, 1-Pentanol, Isopentenol, 2-Methyl-1-butanol, 3-Methyl-1-butanol, 1-Hexanol, 3-Methyl-1-pentanol, 1-Heptanol, 4-Methyl-1-hexanol, and 5-Methyl-1-hexanol. Diols include propanediols and butanediols, including 1,4 butanediol, 1,3-butanediol and 2,3-butanediol. Fatty alcohols include C4-C27 fatty alcohols, including C12-C18, especially C12-C14, including saturated or unsaturated linear fatty alcohols.

Further exemplary bioderived compounds of the invention include: (a) 1,4-butanediol and intermediates thereto, such as 4-hydroxybutanoic acid (4-hydroxybutanoate, 4-hydroxybutyrate (4-HB); (b) butadiene (1,3-butadiene) and intermediates thereto, such as 1,4-butanediol, 1,3-butanediol, 2,3-butanediol, crotyl alcohol, 3-buten-2-ol (methyl vinyl carbinol) and 3-buten-1-ol; (c) 1,3-butanediol and intermediates thereto, such as 3-hydroxybutyrate (3-HB), 2,4-pentadienoate, crotyl alcohol or 3-buten-1-ol; (d) adipate, 6-aminocaproic acid (6-ACA), caprolactam, hexamethylenediamine (HMDA) and levulinic acid and their intermediates, for example, adipyl-CoA, 4-aminobutyryl-CoA; (e) methacrylic acid (2-methyl-2-propenoic acid) and its esters, such as methyl methacrylate and other methacrylate esters (known collectively as methacrylates), 3-hydroxyisobutyrate and/or 2-hydroxyisobutyrate and their intermediates; (f) glycols, including 1,2-propanediol (propylene glycol), 1,3-propanediol, glycerol, ethylene glycol, diethylene glycol, triethylene glycol, dipropylene glycol, tripropylene glycol, neopentyl glycol and bisphenol A and their intermediates; (g) succinic acid and intermediates thereto; and (h) fatty alcohols, which are aliphatic compounds containing one or more hydroxyl groups and a chain of 4 or more carbon atoms, or fatty acids and fatty aldehydes thereof, which are preferably C4-C27 carbon atoms. Fatty alcohols include saturated fatty alcohols, unsaturated fatty alcohols and linear saturated fatty alcohols. Examples fatty alcohols include butyl, pentyl, hexyl, heptyl, octyl, nonyl, decyl, undecyl and dodecyl alcohols, and their corresponding oxidized derivatives, i.e. fatty aldehydes or fatty acids having the same number of carbon atoms. Preferred fatty alcohols, fatty aldehydes and fatty acids have C8 to C18 carbon atoms, especially C12-C18, C12-C14, and C16-C18, including C12, C13, C14, C15, C16, C17, and C18 carbon atoms. Preferred fatty alcohols include linear unsaturated fatty alcohols, such as dodecanol (C12; lauryl alcohol), tridecyl alcohol (C13; 1-tridecanol, tridecanol, isotridecanol), myristyl alcohol (C14; 1-tetradecanol), pentadecyl alcohol (C15; 1-pentadecanol, pentadecanol), cetyl alcohol (C16; 1-hexadecanol), heptadecyl alcohol (C17; 1-n-heptadecanol, heptadecanol) and stearyl alcohol (C18; 1-octadecanol) and unsaturated counterparts including palmitoleyl alcohol (C16 unsaturated; cis-9-hexadecen-1-ol), or their corresponding fatty aldehydes or fatty acids.

1,4-Butanediol and intermediates thereto, such as 4-hydroxybutanoic acid (4-hydroxybutanoate, 4-hydroxybutyrate, 4-HB), are bioderived compounds that can be made via enzymatic pathways described herein and in the following publications. Suitable bioderived compound pathways and enzymes, methods for screening and methods for isolating are found in: WO2008115840A2 published 25 Sep. 2008 entitled Compositions and Methods for the Biosynthesis of 1,4-Butanediol and Its Precursors and US20090075351; WO2010141780A1 published 9 Dec. 2010 entitled Process of Separating Components of A Fermentation Broth and US20110003355; WO2010141920A2 published 9 Dec. 2010 entitled Microorganisms for the Production of 1,4-Butanediol and Related Methods and US20110045575; WO2010030711A2 published 18 Mar. 2010 entitled Microorganisms for the Production of 1,4-Butanediol and US20100112654; WO2010071697A1 published 24 Jun. 2010 entitled Microorganisms and Methods for Conversion of Syngas and Other Carbon Sources to Useful Products and US20100304453; WO2009094485A1 published 30 Jul. 2009 entitled Methods and Organisms for Utilizing Synthesis Gas or Other Gaseous Carbon Sources and Methanol and US20090191593; and WO2009023493A1 published 19 Feb. 2009 entitled Methods and Organisms for the Growth-Coupled Production of 1,4-Butanediol and US20090047719, which are all incorporated herein by reference. Exemplary BDO pathways are described in the references above and can include, for example, an α-ketoglutarate dehydrogenase and a CoA-dependent succinic semialdehyde dehydrogenase, or an α-ketoglutarate decarboxylase, or a glutamate:succinate semialdehyde transaminase and a glutamate decarboxylase; a 4-hydroxybutanoate dehydrogenase; a 4-hydroxybutyryl-CoA:acetyl-CoA transferase, or a butyrate kinase and a phosphotransbutyrylase, an aldehyde dehydrogenase, and an alcohol dehydrogenase, or an aldehyde/alcohol dehydrogenase, (see US 20090075351, which is incorporated herein by reference).

Butadiene and intermediates thereto, such as 1,4-butanediol, 2,3-butanediol, 1,3-butanediol, crotyl alcohol, 3-buten-2-ol (methyl vinyl carbinol) and 3-buten-1-ol, are bioderived compounds that can be made via enzymatic pathways described herein and in the following publications. In addition to direct fermentation to produce butadiene, 1,3-butanediol, 1,4-butanediol, crotyl alcohol, 3-buten-2-ol (methyl vinyl carbinol) or 3-buten-1-ol can be separated, purified (for any use), and then chemically dehydrated to butadiene by metal-based catalysis. Suitable bioderived compound pathways and enzymes, methods for screening and methods for isolating are found in: WO2011140171A2 published 10 Nov. 2011 entitled Microorganisms and Methods for the Biosynthesis of Butadiene and US20110300597; WO2012018624A2 published 9 Feb. 2012 entitled Microorganisms and Methods for the Biosynthesis of Aromatics, 2,4-Pentadienoate and 1,3-Butadiene and US20120021478; WO2013040383A1 published 21 Mar. 2013 entitled Microorganisms and Methods for Producing Alkenes and US20130122563; WO2012177710A1 published 27 Dec. 2012 entitled Microorganisms for Producing Butadiene and Methods Related thereto and US20130011891; WO2012106516A1 published 9 Aug. 2012 entitled Microorganisms and Methods for the Biosynthesis of Butadiene and US20120225466; and WO2013028519A1 published 28 Feb. 2013 entitled Microorganisms and Methods for Producing 2,4-Pentadienoate, Butadiene, Propylene, 1,3-Butanediol and Related Alcohols and US20130109064, which are all incorporated herein by reference.

1,3-Butanediol and intermediates thereto, such as 2,4-pentadienoate, crotyl alcohol or 3-buten-1-ol, are bioderived compounds that can be made via enzymatic pathways described herein and in the following publications. Suitable bioderived compound pathways and enzymes, methods for screening and methods for isolating are found in: WO2011071682A1 published 16 Jun. 2011 entitled Methods and Organisms for Converting Synthesis Gas or Other Gaseous Carbon Sources and Methanol to 1,3-Butanediol and US20110129904; WO2011031897A published 17 Mar. 2011 entitled Microorganisms and Methods for the Co-Production of Isopropanol with Primary Alcohols, Diols and Acids and US 20110201068; WO2010127319A2 published 4 Nov. 2010 entitled Organisms for the Production of 1,3-Butanediol and US20100330635; WO2013071226A1 published 16 May 2013 entitled Eukaryotic Organisms and Methods for Increasing the Availability of Cytosolic Acetyl-CoA, and for Producing 1,3-Butanediol and US20130066035; WO2013028519A1 published 28 Feb. 2013 entitled Microorganisms and Methods for Producing 2,4-Pentadienoate, Butadiene, Propylene, 1,3-Butanediol and Related Alcohols and US 20130109064; WO2013036764A1 published 14 Mar. 2013 entitled Eukaryotic Organisms and Methods for Producing 1,3-Butanediol and US20130066035; WO2013012975A1 published 24 Jan. 2013 entitled Methods for Increasing Product Yields; and WO2012177619A2 published 27 Dec. 2012 entitled Microorganisms for Producing 1,3-Butanediol and Methods Related Thereto and US20120329113, which are all incorporated herein by reference.

Adipate, 6-aminocaproic acid, caprolactam, hexamethylenediamine and levulinic acid, and their intermediates, e.g. 4-aminobutyryl-CoA, are bioderived compounds that can be made via enzymatic pathways described herein and in the following publications. Suitable bioderived compound pathways and enzymes, methods for screening and methods for isolating are found in: WO2010129936A1 published 11 Nov. 2010 entitled Microorganisms and Methods for the Biosynthesis of Adipate, Hexamethylenediamine and 6-Aminocaproic Acid and US20120282661; WO2013012975A1 published 24 Jan. 2013 entitled Methods for Increasing Product Yields; WO2012177721A1 published 27 Dec. 2012 entitled Microorganisms for Producing 6-Aminocaproic Acid; WO2012099621A1 published 26 Jul. 2012 entitled Methods for Increasing Product Yields and US20110201089; and WO2009151728 published 17 Dec. 2009 entitled Microorganisms for the Production of Adipic Acid and other Compounds and US20090305364, which are all incorporated herein by reference.

Methacrylic acid (2-methyl-2-propenoic acid) is used in the preparation of its esters, known collectively as methacrylates (e.g. methyl methacrylate, which is used most notably in the manufacture of polymers). Methacrylic acid, methacrylate esters such as methyl methacrylate, and precursors such as 3-hydroxyisobutyrate and/or 2-hydroxyisobutyrate, and their intermediates, are bioderived compounds that can be made via enzymatic pathways described herein and in the following publications. Suitable bioderived compound pathways and enzymes, methods for screening and methods for isolating are found in: WO2012135789A2 published 4 Oct. 2012 entitled Microorganisms for Producing Methacrylic Acid and Methacrylate Esters and Methods Related Thereto and US20130065279; and WO2009135074A2 published 5 Nov. 2009 entitled Microorganisms for the Production of Methacrylic Acid and US20090275096, which are all incorporated herein by reference.

1,2-Propanediol (propylene glycol), n-propanol, 1,3-propanediol and glycerol, and their intermediates are bioderived compounds that can be made via enzymatic pathways described herein and in the following publications. Suitable bioderived compound pathways and enzymes, methods for screening and methods for isolating are found in: WO2009111672A1 published 9 Nov. 2009 entitled Primary Alcohol Producing Organisms and US20090275097; WO2011031897A1 17 Mar. 2011 entitled Microorganisms and Methods for the Co-Production of Isopropanol with Primary Alcohols, Diols and Acids and US20110201068; WO2012177599A2 published 27 Dec. 2012 entitled Microorganisms for Producing N-Propanol 1,3-Propanediol, 1,2-Propanediol or Glycerol and Methods Related Thereto, which are all incorporated herein by referenced.

Succinic acid and intermediates thereto, which are useful to produce products including polymers (e.g. polybutylene succinate or PBS), 1,4-butanediol, tetrahydrofuran, pyrrolidone, solvents, paints, deicers, plastics, fuel additives, fabrics, carpets, pigments, and detergents, are bioderived compounds that can be made via enzymatic pathways described herein and in the following publication. Suitable bioderived compound pathways and enzymes, methods for screening and methods for isolating are found in: EP1937821A2 published 2 Jul. 2008 entitled Methods and Organisms for the Growth-Coupled Production of Succinate, WO/2007/030830 published 15 Mar. 2007 entitled Methods and Organisms for the Growth-coupled Production of Succinate and US20070111294, which are all incorporated herein by reference. It is understood by those skilled in the art that the production of succinate as a desired product can be applicable in the microbial organisms of the invention, if desired, particular those microbial organisms having metabolic modifications that do not result in a decreased production of succinate, for example, a metabolic modification affecting conversion of succinyl-CoA to succinate.

Primary alcohols and fatty alcohols (also known as long chain alcohols), including fatty acids and fatty aldehydes thereof, and intermediates thereof, are bioderived compounds that can be made via enzymatic pathways in the following publications. Suitable bioderived compound pathways and enzymes, methods for screening and methods for isolating are found in: WO2009111672 published 11 Sep. 2009 entitled Primary Alcohol Producing Organisms and US20090275097; WO2012177726 published 27 Dec. 2012 entitled Microorganism for Producing Primary Alcohols and Related Compounds and Methods Related Thereto, which are all incorporated herein by reference.

Further suitable bioderived compounds that the microbial organisms of the invention can be used to produce via acetyl-CoA, including optionally further through acetoacetyl-CoA and/or succinyl-CoA, are included in the invention. Exemplary well known bioderived compounds, their pathways and enzymes for production, methods for screening and methods for isolating are found in the following patents and publications: succinate (U.S. publication 2007/0111294, WO 2007/030830, WO 2013/003432), 3-hydroxypropionic acid (3-hydroxypropionate) (U.S. publication 2008/0199926, WO 2008/091627, U.S. publication 2010/0021978), 1,4-butanediol (U.S. Pat. No. 8,067,214, WO 2008/115840, U.S. Pat. No. 7,947,483, WO 2009/023493, U.S. Pat. No. 7,858,350, WO 2010/030711, U.S. publication 2011/0003355, WO 2010/141780, U.S. Pat. No. 8,129,169, WO 2010/141920, U.S. publication 2011/0201068, WO 2011/031897, U.S. Pat. No. 8,377,666, WO 2011/047101, U.S. publication 2011/0217742, WO 2011/066076, U.S. publication 2013/0034884, WO 2012/177943), 4-hydroxybutanoic acid (4-hydroxybutanoate, 4-hydroxybutyrate, 4-hydroxybutyrate) (U.S. Pat. No. 8,067,214, WO 2008/115840, U.S. Pat. No. 7,947,483, WO 2009/023493, U.S. Pat. No. 7,858,350, WO 2010/030711, U.S. publication 2011/0003355, WO 2010/141780, U.S. Pat. No. 8,129,155, WO 2010/071697), γ-butyrolactone (U.S. Pat. No. 8,067,214, WO 2008/115840, U.S. Pat. No. 7,947,483, WO 2009/023493, U.S. Pat. No. 7,858,350, WO 2010/030711, U.S. publication 2011/0003355, WO 2010/141780, U.S. publication 2011/0217742, WO 2011/066076), 4-hydroxybutyryl-CoA (U.S. publication 2011/0003355, WO 2010/141780, U.S. publication 2013/0034884, WO 2012/177943), 4-hydroxybutanal (U.S. publication 2011/0003355, WO 2010/141780, U.S. publication 2013/0034884, WO 2012/177943), putrescine (U.S. publication 2011/0003355, WO 2010/141780, U.S. publication 2013/0034884, WO 2012/177943), Olefins (such as acrylic acid and acrylate ester) (U.S. Pat. No. 8,026,386, WO 2009/045637), acetyl-CoA (U.S. Pat. No. 8,323,950, WO 2009/094485), methyl tetrahydrofolate (U.S. Pat. No. 8,323,950, WO 2009/094485), ethanol (U.S. Pat. No. 8,129,155, WO 2010/071697), isopropanol (U.S. Pat. No. 8,129,155, WO 2010/071697, U.S. publication 2010/0323418, WO 2010/127303, U.S. publication 2011/0201068, WO 2011/031897), n-butanol (U.S. Pat. No. 8,129,155, WO 2010/071697), isobutanol (U.S. Pat. No. 8,129,155, WO 2010/071697), n-propanol (U.S. publication 2011/0201068, WO 2011/031897), methylacrylic acid (methylacrylate) (U.S. publication 2011/0201068, WO 2011/031897), primary alcohol (U.S. Pat. No. 7,977,084, WO 2009/111672, WO 2012/177726), long chain alcohol (U.S. Pat. No. 7,977,084, WO 2009/111672, WO 2012/177726), adipate (adipic acid) (U.S. Pat. No. 8,062,871, WO 2009/151728, U.S. Pat. No. 8,377,680, WO 2010/129936, WO 2012/177721), 6-aminocaproate (6-aminocaproic acid) (U.S. Pat. No. 8,062,871, WO 2009/151728, U.S. Pat. No. 8,377,680, WO 2010/129936, WO 2012/177721), caprolactam (U.S. Pat. No. 8,062,871, WO 2009/151728, U.S. Pat. No. 8,377,680, WO 2010/129936, WO 2012/177721), hexamethylenediamine (U.S. Pat. No. 8,377,680, WO 2010/129936, WO 2012/177721), levulinic acid (U.S. Pat. No. 8,377,680, WO 2010/129936), 2-hydroxyisobutyric acid (2-hydroxyisobutyrate) (U.S. Pat. No. 8,241,877, WO 2009/135074, U.S. publication 2013/0065279, WO 2012/135789), 3-hydroxyisobutyric acid (3-hydroxyisobutyrate) (U.S. Pat. No. 8,241,877, WO 2009/135074, U.S. publication 2013/0065279, WO 2012/135789), methacrylic acid (methacrylate) (U.S. Pat. No. 8,241,877, WO 2009/135074, U.S. publication 2013/0065279, WO 2012/135789), methacrylate ester (U.S. publication 2013/0065279, WO 2012/135789), fumarate (fumaric acid) (U.S. Pat. No. 8,129,154, WO 2009/155382), malate (malic acid) (U.S. Pat. No. 8,129,154, WO 2009/155382), acrylate (carboxylic acid) (U.S. Pat. No. 8,129,154, WO 2009/155382), methyl ethyl ketone (U.S. publication 2010/0184173, WO 2010/057022, U.S. Pat. No. 8,420,375, WO 2010/144746), 2-butanol (U.S. publication 2010/0184173, WO 2010/057022, U.S. Pat. No. 8,420,375, WO 2010/144746), 1,3-butanediol (U.S. publication 2010/0330635, WO 2010/127319, U.S. publication 2011/0201068, WO 2011/031897, U.S. Pat. No. 8,268,607, WO 2011/071682, U.S. publication 2013/0109064, WO 2013/028519, U.S. publication 2013/0066035, WO 2013/036764), cyclohexanone (U.S. publication 2011/0014668, WO 2010/132845), terephthalate (terephthalic acid) (U.S. publication 2011/0124911, WO 2011/017560, U.S. publication 2011/0207185, WO 2011/094131, U.S. publication 2012/0021478, WO 2012/018624), muconate (muconic acid) (U.S. publication 2011/0124911, WO 2011/017560), aniline (U.S. publication 2011/0097767, WO 2011/050326), p-toluate (p-toluic acid) (U.S. publication 2011/0207185, WO 2011/094131, U.S. publication 2012/0021478, WO 2012/018624), (2-hydroxy-3-methyl-4-oxobutoxy)phosphonate (U.S. publication 2011/0207185, WO 2011/094131, U.S. publication 2012/0021478, WO 2012/018624), ethylene glycol (U.S. publication 2011/0312049, WO 2011/130378, WO 2012/177983), propylene (U.S. publication 2011/0269204, WO 2011/137198, U.S. publication 2012/0329119, U.S. publication 2013/0109064, WO 2013/028519), butadiene (1,3-butadiene) (U.S. publication 2011/0300597, WO 2011/140171, U.S. publication 2012/0021478, WO 2012/018624, U.S. publication 2012/0225466, WO 2012/106516, U.S. publication 2013/0011891, WO 2012/177710, U.S. publication 2013/0109064, WO 2013/028519), toluene (U.S. publication 2012/0021478, WO 2012/018624), benzene (U.S. publication 2012/0021478, WO 2012/018624), (2-hydroxy-4-oxobutoxy)phosphonate (U.S. publication 2012/0021478, WO 2012/018624), benzoate (benzoic acid) (U.S. publication 2012/0021478, WO 2012/018624), styrene (U.S. publication 2012/0021478, WO 2012/018624), 2,4-pentadienoate (U.S. publication 2012/0021478, WO 2012/018624, U.S. publication 2013/0109064, WO 2013/028519), 3-butene-1-ol (U.S. publication 2012/0021478, WO 2012/018624, U.S. publication 2013/0109064, WO 2013/028519), 3-butene-2-ol (U.S. publication 2013/0109064, WO 2013/028519), 1,4-cyclohexanedimethanol (U.S. publication 2012/0156740, WO 2012/082978), crotyl alcohol (U.S. publication 2013/0011891, WO 2012/177710, U.S. publication 2013/0109064, WO 2013/028519), alkene (U.S. publication 2013/0122563, WO 2013/040383), or caprolactone (U.S. publication 2013/0144029, WO 2013/067432) pathway. The patents and patent application publications listed above that disclose bioderived compound pathways are herein incorporated herein by reference.

The invention additionally provides a non-naturally occurring microbial organism having a genetic alteration that increases the availability of adenosine triphosphate (ATP). The genetic alteration that increases the availability of ATP can be alone or in combination with any of the genetic alterations described herein including, for example, a genetic alteration that increases the availability of ATP in a non-naturally occurring microbial organism having a first attenuation of a succinyl-CoA synthetase and a second attenuation of a succinyl-CoA converting enzyme or a succinate producing enzyme as described previously. Thus, the invention also provides a non-naturally occurring microbial organism having a first attenuation of a succinyl-CoA synthetase and a second attenuation of a succinyl-CoA converting enzyme or a succinate producing enzyme, and further having a genetic alteration that increases the availability of adenosine triphosphate (ATP) in the microbial organism. The genetic alteration that increases the availability of ATP can include increasing the expression of NADH dehydrogenase Ndh-I, cytochrome bo oxidase or both NADH dehydrogenase Ndh-I and cytochrome bo oxidase.

Attenuating one or more genes catalyzing the conversion from succinyl-CoA to succinate in the oxidative TCA cycle can lead to a reduction in growth rate in some strain backgrounds due to energy or redox limitations. This growth defect can be overcome by carbon-conserving strategies that increase availability of ATP or improve the energy yield or energetic efficiency of the strain. Such strategies include, for example, (1) engineering the electron transport chain, and (2) substituting or supplementing phosphoenoylpyruvate carboxylase (PPC) with ATP-generating phosphoenoylpyruvate carboxykinase (PEPCK). Each strategy is described in further detail below. In addition to their use in host microbial organisms having attenuation of a TCA cycle enzyme, each of these genetic alterations are similarly applicable to increase ATP or improve the energy yield or energetic efficiency of host microbial organisms that generates a bioderived compound from a substrate other than a TCA cycle intermediate or substrate.

In this regard, a microbial organism's growth and energy yield can be improved by engineering the electron transport chain to be more efficient in the production of ATP. The respiratory chain of, for example, E. coli includes various NADH dehydrogenases. The NADH dehydrogenases include Ndh-I, Ndh-II, WrbA, YhdH, YieF, YtfG, Qor and MdaB on the electron input side of the respiratory chain. The respiratory chain of, for example, E. coli also includes four different ubiquinol oxidases on the output side. The ubiquinol oxidases include cytochrome bo oxidase, cytochrome bd-I oxidase, cytochrome bd-II oxidase and quinol monooxygenase (Bekker et al, *J Bacteriol* 191:5510-17 (2009)). The cytochrome oxidases have different energy-conserving efficiencies. The cytochrome bo complex, encoded by the cyo operon, actively pumps electrons over the membrane and results in an H+/2e− stoichiometry of 4. The cytochrome bd-I complex does not appear to actively pump protons, but due to the oxidation of the quinol on the periplasmic side of the membrane and subsequent uptake of protons from the cytoplasmic side of the membrane, which are used in the formation of water, the net electron transfer results in a H+/2e− stoichiometry of 2. This oxidase is encoded by the cyd operon. Until recently, the proton translocation stoichiometry of cytochrome bd-II oxidase, encoded by appBC, was not known, but it has now been described that this oxidase is non-electrogenic (Bekker et al, supra). YgiN is also non-electrogenic (Portnoy et al, *AEM* 74:7561-69 (2008)). The NADH dehydrogenases also have different energy-conserving efficiencies and only Ndh-1, encoded by nuo, translocates protons. NADH dehydrogenase I (nuo) and cytochrome bo oxidase encoded by cyoABCDE are the most efficient components of this chain, each translocating four protons per pair of electrons transferred. The energetic efficiency of the respiratory chain is maximal when the electron transport chain utilizes cytochrome oxidase Cyo and the NADH dehydrogenase Nuo. Optimizing expression level of Cyo and/or Nuo can therefore be performed to increase the efficiency of the electron transport chain and the growth and energy yield of the organisms.

Given the teachings and guidance provided herein, those skilled in the art will understand that there are a variety of different approaches that can be employed to increase the efficiency of the electron transport chain and thereby increase cell growth and energy yield. One approach involves increasing the expression of NADH dehydrogenase Ndh-I (nuo) and/or increasing the expression of cytochrome bo oxidase (cyoABCDE). Expression can be increased by, for example, overexpression of an endogenous encoding gene and/or expression of an exogenous encoding nucleic acid. Overexpression of an endogenous gene includes, for example, up regulation and removal of negative regulation as described herein. By reference to expression of an exogenous encoding nucleic acid for exemplification purposes, one approach that can be employed to increase the efficiency of the electron transport chain involves expressing an exogenous nucleic acid encoding NADH dehydrogenase Ndh-I or cytochrome bo oxidase. An alternative approach involves expressing one or more exogenous nucleic acids encoding both a NADH dehydrogenase Ndh-I (nuo) and cytochrome bo oxidase (cyoABCDE). Exogenous expression or endogenous overexpression of one or both of these enzymes of the electron transport chain will increase their availability for electron transport and therefore increase its efficiency. As described further below, various other methods also are available for increasing expression of either an endogenous or exogenous nucleic acid including, for example, incorporating stronger promoters and/or positive regulatory elements of either the endogenous encoding nucleic acids, the exogenous encoding nucleic acids or both. Those skilled in the art will appreciate that some or all of such methods can be used alone or in combination to increase expression of an encoding nucleic acid.

Increases in electron transport efficiency and ATP generation also can be obtained by, for example, attenuation of one or more, including all, of the remaining endogenous NADH dehydrogenases or NAD(P)H:quinine oxidoreductases. Similarly, attenuation of one or more, including all, of the remaining endogenous ubiquinol oxidases also can be generated to increase efficiencies. In like fashion, incorporating an attenuation of both of one or more, including all, of the remaining NADH dehydrogenases and NAD(P)H:quinine oxidoreductases and one or more, including all, of the remaining ubiquinol oxidases can similarly increase efficiencies. The attenuation can be a gene disruption or other genetic alteration described herein or well known in the art that results in diminution of gene expression or gene product activity. Such methods include, for example, altering a promoter, regulatory region or a gene expression regulator of the encoding gene.

The remaining endogenous NAD(P)H dehydrogenases or NAD(P)H:quinine oxidoreductases involved in electron transport include NAD(P)H dehydrogenases or NAD(P)H:

quinine oxidoreductases Ndh-II, WrbA, YhdH, YieF, YtfG, Qor and MdaB (non-Ndh-I NADH dehydrogenases). The one or more of these dehydrogenases or oxidoreductases can be attenuated to increase electron transport efficiencies and increase ATP yield because it will result in increased electron transport through Ndh-I. Accordingly, the microbial organisms of the invention can have attenuation of one or more of Ndh-II, WrbA, YhdH, YieF, YtfG, Qor or MdaB, including attenuation for all of these NAD(P)H dehydrogenases and/or NAD(P)H:quinine oxidoreductases. Similarly, a microbial organism of the invention can have attenuations for all combinations of the above seven NAD(P)H dehydrogenases and/or NAD(P)H:quinine oxidoreductases including, for example, attenuations for all combinations of two, three, four, five and six NAD(P)H dehydrogenases and/or NAD(P)H:quinine oxidoreductases. An attenuation of one or more non-Ndh-I NADH dehydrogenases as described above can be generated in a microbial organism of the invention either alone to increase electron transport efficiency and ATP availability or used in conjunction with increased expression of NADH dehydrogenase Ndh-I, cytochrome bo oxidase or both NADH dehyrogenase Ndh-I and cytochrome bo oxidase as described previously.

The remaining endogenous ubiquinol oxidases involved in electron transport include cytochrome bd-I oxidase, cytochrome bd-II oxidase and quinol monooxygenase (non-cytochrome bo oxidases). The gene encoding one or more of these oxidases can be disrupted to increase electron transport efficiencies and increase ATP yield because such a attenuation or disruptions will result in increased electron transport through cytochrome bo oxidase. Accordingly, the microbial organisms of the invention can have a attenuation of one or more of cytochrome bd-I oxidase, cytochrome bd-II oxidase or quinol monooxygenase, including a attenuation for all of these ubiquinol oxidases. Similarly, a microbial organism of the invention can have attenuations for all combinations of the above three ubiquinol oxidases including, for example, attenuations for all combinations of two ubiquinol oxidases. A attenuation of one or more non-cytochrome bo oxidases as described above can be generated in a microbial organism of the invention either alone to increase electron transport efficiency and ATP availability or used in conjunction with increased expression of NADH dehydrogenase Ndh-I, cytochrome bo oxidase or both NADH dehyrogenase Ndh-I and cytochrome bo oxidase as described previously.

As with attenuations for some or all the endogenous NAD(P)H dehydrogenases or NAD(P)H:quinine oxidoreductases other than Ndh-I (i.e., the non-Ndh-I NADH dehydrogenases) or some or all of the ubiquinol oxidases other than cytochrome bo oxidases (i.e., the non-cytochrome bo oxidases), attenuations for one or more of both a non-Ndh-I NADH dehydrogenase and a non-cytochrome bo oxidases can be generated to increase electron transport efficiencies and increase ATP yield because such attenuations will result in increased electron transport through Ndh-I NADH dehydrogenase and cytochrome bo oxidase. Accordingly, the microbial organisms of the invention can have an attenuation of one or more of Ndh-II, WrbA, YhdH, YieF, YtfG, Qor or MdaB, including an attenuation for all of these NAD(P)H dehydrogenases and NAD(P)H:quinine oxidoreductases, and an attenuation of one or more of cytochrome bd-I oxidase, cytochrome bd-II oxidase or quinol monooxygenase, including an attenuation for all of these ubiquinol oxidases. One exemplary combination includes attenuation of Ndh-II, bd-I oxidase or Ndh-II and bd-I oxidase. Similarly, a microbial organism of the invention can have attenuations for all combinations of the above seven NAD(P)H dehydrogenases and/or NAD(P)H:quinine oxidoreductases including, for example, attenuations for all combinations of two, three, four, five and six NAD(P)H dehydrogenases and/or NAD(P)H:quinine oxidoreductases, and can have attenuations for all combinations of the above three ubiquinol oxidases including, for example, attenuations for all combinations of two ubiquinol oxidases. An attenuation of one or more non-Ndh-I NADH dehydrogenases and/or non-cytochrome bo oxidases as described above can be generated in a microbial organism of the invention either alone to increase electron transport efficiency and ATP availability or used in conjunction with increased expression of NADH dehyrogenase Ndh-I, cytochrome bo oxidase or both NADH dehyrogenase Ndh-I and cytochrome bo oxidase as described previously.

Exemplary non-Ndh-I NADH dehydrogenases and non-cytochrome bo oxidases that are useful for attenuation to improve energetic efficiency of the electron transport chain and thereby increase the availability of ATP are summarized in Table 14 below.

TABLE 14

Exemplary Non-Ndh-I NADH Dehydrogenases and Non-cytochrome bo Oxidases

| Gene name | GenBank Accession # | GI # | Organism |
| --- | --- | --- | --- |
| appB | NP_415498.1 | 16128945 | Escherichia coli |
| appC | NP_415497.1 | 16128944 | Escherichia coli |
| ygiN | NP_417501.1 | 16130925 | Escherichia coli |
| mdaB | NP_417500.1 | 16130924 | Escherichia coli |
| wrbA | P0A8G6.2 | 67475535 | Escherichia coli |
| yieF | P0AGE6.1 | 84028020 | Escherichia coli |
| Qor | NP_418475.1 | 16131877 | Escherichia coli |
| ytfG | NP_418632.1 | 16132033 | Escherichia coli |
| cydA | NP_415261.2 | 90111166 | Escherichia coli |
| cydB | NP_415262.1 | 16128709 | Escherichia coli |
| ndh | NP_415627.1 | 16129072 | Escherichia coli |

The invention also provides a non-naturally occurring microbial organism having an attenuation of one or more menaquinol or dimethylmenaquinol biosynthetic enzymes. The attenuation of one or more menaquinol or dimethylmenaquinol biosynthetic enzymes can be alone or in combination with any of the genetic alterations described herein including, for example, attenuation of one or more menaquinol or dimethylmenaquinol biosynthetic enzymes in a non-naturally occurring microbial organism having a first attenuation of a succinyl-CoA synthetase and a second attenuation of a succinyl-CoA converting enzyme or a succinate producing enzyme as described previously. Thus, the invention also provides a non-naturally occurring microbial organism having a first attenuation of a succinyl-CoA synthetase and a second attenuation of a succinyl-CoA converting enzyme or a succinate producing enzyme, and further having an attenuation of one or more menaquinol or dimethylmenaquinol biosynthetic enzymes. The attenuation can be attenuation of one or more menaquinol biosynthetic enzymes, one or more dimethylmenaquinol biosynthetic enzymes or one or more menaquinol biosynthetic enzymes and one or more dimethylmenaquinol biosynthetic enzymes. The attenuation can be a gene disruption or other genetic alteration described herein or well known in the art that results in diminution of gene expression or gene product activity. Such methods include, for example, altering a promoter, regulatory region or a gene expression regulator of the encoding gene. Genes encoding exemplary menaquinol and dimethylmenaquinol biosynthetic enzymes are set forth in Table 15.

A related genetic alteration that can be employed for improving efficiency of the electron transport chain and increasing ATP yields is to alter the composition of the quinone pool such that the total ubiquinone and ubiquinol pools are increased and the menaquinone and menaquinol pools are decreased. The composition of the quinone pool can be regulated by oxygen availability (Shestopalov et al, FEBS Lett 404: 2-3: 272-4 (1997)). Cyo and Cyd can both oxidize ubiquinol. However, Cyd also can oxidize menaquinol whereas Cyo exhibits little activity for menaquinol. Disrupting menaquinone and/or menaquinol biosynthesis can therefore be utilized to increased flux through Cyo by shifting the distribution of the quinone pool toward ubiquinone and ubiquinol, leading to more energy efficient respiration.

Exemplary menaquinone biosynthetic enzymes that are useful for attenuation to improve energetic efficiency of the electron transport chain and thereby increase the availability of ATP are summarized in Table 15 below.

TABLE 15

Exemplary Menaquinone Biosynthetic Enzymes

| Gene name | GenBank Accession # | GI # | Organism |
| --- | --- | --- | --- |
| menF | NP_416768.4 | 90111411 | Escherichia coli |
| menD | NP_416767.1 | 16130199 | Escherichia coli |
| menH | YP_026269.1 | 49176426 | Escherichia coli |
| menC | NP_416764.1 | 16130196 | Escherichia coli |
| menE | NP_416763.1 | 16130195 | Escherichia coli |
| menB | NP_416765.1 | 16130197 | Escherichia coli |
| menI | AAC74756.1 | 1787976 | Escherichia coli |
| menA | NP_418365.1 | 16131768 | Escherichia coli |
| menG | YP_026269.1 | 49176426 | Escherichia coli |

The invention also provides a non-naturally occurring microbial organism having a phosphoenoylpyruvate carboxylase (PPC) supplemented or substituted with an ATP-generating phosphoenoylpyruvate carboxykinase (PEPCK; also termed PPCK). The substitution or supplementation can be alone or in combination with any of the genetic alterations described herein including, for example, substituting or supplementing PPC with an ATP-generating PEPCK in a non-naturally occurring microbial organism having a first attenuation of a succinyl-CoA synthetase and a second attenuation of a succinyl-CoA converting enzyme or a succinate producing enzyme as described herein. Thus, the invention also provides a non-naturally occurring microbial organism having a first attenuation of a succinyl-CoA synthetase and a second attenuation of a succinyl-CoA converting enzyme or a succinate producing enzyme, and further having a PPC supplemented or substituted with an ATP-generating PEPCK.

Another genetic alteration that can be employed to increase ATP availability in host microbial organisms of the invention includes substituting or supplementing PPC with an ATP-generating phosphoenoylpyruvate carboxykinase PEPCK.

By way of exemplification in E. coli, for example, two enzymes catalyze the interconversion of phosphoenolpyruvate (PEP) and oxaloacetate. One enzyme corresponds to PEP carboxylase (PPC, EC 4.1.1.31) and the second enzyme corresponds to PEP carboxykinase (PPCK, EC 4.1.1.49). The reactions catalyzed by each of these enzymes are summarized in the formulas below.

PEP+$CO_2$+$H_2O$→OAA+Pi (PPC)

PEP+$CO_2$+ATP→OAA+ADP (PEPCK)

As illustrated and described above, both PPC and PEPCK enzymes catalyze the carboxylation of PEP to oxaloacetate. Oxaloacetate formation via PEPCK generates ATP, which improves ATP availability in TCA cycle disrupted and non-disrupted TCA cycle strains. PEPCK activity can substitute for PPC activity, or can complement (supplement) it. Exemplary PEPCK enzymes are described in further detail below. Those skilled in the art also will know that supplementation of the medium in the methods described herein with bicarbonate, aspartate or excess $CO_2$ can be useful to achieve higher growth rates.

Supplementation of PPC includes, for example, overexpression of an endogenous PEPCK encoding nucleic acid and/or expression of an exogenous nucleic acid encoding PEPCK. Over expression includes, for example, up regulation and removal of negative regulation as described herein. As with any expression of an exogenous encoding nucleic acid described herein, the exogenous nucleic acid can be an encoding nucleic acid that is homologous to the host microbial organism or it can be an encoding nucleic acid that is heterologous to the host. Substitution of PPC includes, for example, attenuation of endogenous PPC and either overexpression of an endogenous PEPCK encoding nucleic acid and/or expression of an exogenous nucleic acid encoding PEPCK. The attenuation can be a gene disruption or other genetic alteration described herein or well known in the art that results in diminution of gene expression or gene product activity. Such methods include, for example, altering a promoter, regulatory region or a gene expression regulator of the encoding gene.

As described further below, various methods also are available for increasing expression of either an endogenous or exogenous nucleic acid including, for example, incorporating stronger promoters and/or positive regulatory elements of either the endogenous encoding nucleic acids, the exogenous encoding nucleic acids or both. Those skilled in the art will appreciate that some or all of such methods can be used alone or in combination to increase expression of an encoding nucleic acid.

With respect to exemplary PEPCK enzymes, PEPCK enzymes of S. cerevisiae and Escherichia coli are encoded by PCK1 and pckA, respectively (Valdes-Hevia et al., FEBS. Lett. 258:313-316 (1989); Kim et al., Appl Environ Microbiol 70:1238-1241 (2004)). The E. coli PEPCK is primarily active during gluconeogenesis. However, activity of the endogenous E. coli PEPCK from PEP towards oxaloacetate has been demonstrated in ppc mutants of E. coli K-12 (Kwon et al., J Micro Biotech 16:1448-1452 (2006)). These strains exhibited no growth defects and had increased succinate production at high $NaHCO_3$ concentrations. Thus, substitution of PPC with PEPCK can be used to further enhance the generation of ATP. An alternative metabolic design to enhance ATP generation through PEPCK can include reducing the affinity to oxaloacetate. For example, the activity of the E. coli PEPCK enzyme in the oxaloacetate-consuming direction can be reduced by introducing an amino acid substitution at the oxaloacetate binding site (pck R65Q) (Cotelesage et al., Int. J Biochem. Cell Biol. 39:1204-1210 (2007)). In some organisms, particularly rumen bacteria, PEPCK is quite efficient in producing oxaloacetate from PEP and generating ATP. Such efficient PEPCK enzymes also are applicable for use in the microbial organisms of the invention that are modified for increased ATP production. Examples of PEPCK genes that have been cloned into *E. coli* and similarly applicable for use in the microbial organisms of the invention include those from *Mannheimia succiniciproducens* (Lee et al., *Biotechnol. Bioprocess Eng.* 7:95-99 (2002)), *Anaerobiospirillum succiniciproducens* (Laivenieks et al., *Appl Environ Microbiol* 63:2273-2280 (1997)), and *Actinobacillus succinogenes* (Kim et al., *Appl Environ Microbiol* 70:1238-1241 (2004)). The PEPCK enzyme from *Megathyrsus maximus* has a low Km for $CO_2$, a substrate thought to be rate-limiting in the *E. coli* enzyme (Chen et al., *Plant Physiol* 128:160-164 (2002); Cotelesage et al., *Int. J Biochem. Cell Biol.* 39:1204-1210 (2007)). Yet another enzyme candidate is the PEPCK enzyme of *Haemophilus influenza*. Exemplary PEPCK enzymes is summarized in Table 16 below.

TABLE 16

Exemplary PEPCK Enzymes

| Protein | GenBank ID | GI Number | Organism |
| --- | --- | --- | --- |
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| AF532733.1:1 ... 1929 | AAQ10076.1 | 33329363 | *Megathyrsus maximus* |
| pckA | P43923.1 | 1172573 | *Haemophilus influenza* |

Attenuation or tuning down expression, including, for example, gene disruption of an encoding nucleic acid for endogenous PPC enzymes, can be beneficial to prevent or reduce an ATP consuming cycle with PEPCK and to ensure that PEPCK is the main source of oxaloacetate. Exemplary PPC enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989). Exemplary PPC enzymes is summarized in Table 17 below.

TABLE 17

Exemplary PPC Enzymes

| Protein | GenBank ID | GI Number | Organism |
| --- | --- | --- | --- |
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

The oxaloacetate-forming activity of PEPCK or PPC in a host microbial organism of the invention, including a host having reduced succinyl-CoA to succinate activity, can be increased by overexpression of PEPCK and/or PPC. PEPCK activity can be further improved by increasing the availability of intracellular PEP. This increase can be accomplished, for example, by disruption of the glucose PTS system and/or increasing the expression of a non-PTS system such as glucose permease, glucose facilitator or glucose ABC transporter. Another strategy for increasing intracellular PEP is to attenuate pyruvate kinase which catalyzes the ADP-dependent conversion of phosphoenolpyruvate to pyruvate. The above attenuations and increases in gene expression can occur by any of the methods described herein including, for example, gene disruption of one or more encoding genes to disrupt a PTS system and/or pyruvate kinase and by overexpression of an endogenous gene or expression of an exogenous encoding nucleic acid for increasing expression of the genes exemplified above. Exemplary genes whose disruption could improve conversion of PEP to oxaloacetate in a strain with reduced succinyl-CoA to succinate activity are shown in Table 18 below.

TABLE 18

Exemplary Genes Whose Disruption
Improves Conversion of PEP to Oxaloacetate

| Protein | GenBank ID | GI Number | Organism |
| --- | --- | --- | --- |
| pykA | NP_416368.1 | 16129807 | *Escherichia coli* |
| pykF | NP_416191.1 | 16129632 | *Escherichia coli* |

TABLE 18-continued

Exemplary Genes Whose Disruption
Improves Conversion of PEP to Oxaloacetate

| Protein | GenBank ID | GI Number | Organism |
| --- | --- | --- | --- |
| ptsI | NP_416911.1 | 16130342 | *Escherichia coli* |
| ptsH | NP_416910.1 | 16130341 | *Escherichia coli* |
| Crr | NP_416912.1 | 16130343 | *Escherichia coli* |
| ptsG | NP_415619.1 | 16129064 | *Escherichia coli* |
| manX | NP_416331.1 | 16129771 | *Escherichia coli* |
| manY | NP_416332.1 | 16129772 | *Escherichia coli* |
| manZ | NP_416333.4 | 345452720 | *Escherichia coli* |

The non-naturally occurring microbial organisms of the invention include all combinations and permutations of the genetic alterations described herein. Thus, as set forth herein with respect to certain exemplary combinations of genetic alterations, any of the genetic alterations described herein can be combined with one or more genetic alterations described herein to generate a non-naturally occurring microbial organism having one or more of the metabolic characteristics resulting therefrom. The combinations of different genetic alterations can include, for example, two, three, four, five, six, seven, eight or nine or more combinations of genetic alterations, including a microbial organism having any number of genetic alterations described herein up to a combinations of all genetic alterations described herein. Accordingly, certain of the various combinations of genetic alterations are exemplified below for illustration purposes. However, given the teachings and guidance provided herein those skilled in the art will understand that all other combinations not exemplified above or below are included within the invention as it is described herein.

For example, in one exemplary embodiment the invention provides a non-naturally occurring microbial organism having an attenuation of YciA CoA hydrolase and a metabolically engineered pathway for producing a bioderived compound from a TCA cycle intermediate or a TCA cycle substrate. The TCA cycle intermediate or TCA cycle substrate can be, for example, α-ketoglutarate, succinyl-CoA and/or acetyl-CoA. The non-naturally occurring microbial organism can further include, for example, expression of an exogenous nucleic acid encoding a pyridine nucleotide transhydrogenase. The exogenous nucleic acid encoding the pyridine nucleotide transhydrogenase can be, for example, pntAB.

The non-naturally occurring microbial organism having an attenuation of YciA CoA hydrolase and a metabolically engineered pathway for producing a bioderived compound from a TCA cycle intermediate or TCA cycle substrate can include, for example, attenuation of an a TCA cycle enzyme. The bioderived compound produced from a TCA cycle intermediate or TCA cycle substrate can include, for example, 4HB, 1,4-BDO, 1,3-BDO, PHB, butadiene, adipate, 6-aminocaproate, caprolactam, methacrylic acid, isopropanol, long chain alcohols, hexamethylenediamene, methyl methacrylate, butanol, 3-butene-1-ol, 3-butene-2-ol and crotyl-alcohol.

The non-naturally occurring microbial organism having a YciA hydrolase attenuation and a metabolically engineered pathway for producing a bioderived compound from a TCA cycle intermediate or TCA cycle substrate can include, for example, a genetic alteration that increases the availability of adenosine triphosphate (ATP) in the microbial organism. The genetic alteration can be, for example, increased expression of NADH dehydrogenase Ndh-I, cytochrome bo oxidase or both NADH dehydrogenase Ndh-I and cytochrome bo oxidase and can include, for example, expression of an exogenous nucleic acid encoding the NADH dehydrogenase Ndh-I (nuo), cytochrome bo oxidase (cyoABCDE) or both NADH dehydrogenase Ndh-I (nuo) and cytochrome bo oxidase (cyoABCDE).

The non-naturally occurring microbial organism having a YciA hydrolase attenuation and a metabolically engineered pathway for producing a bioderived compound from a TCA cycle intermediate or TCA cycle substrate can include, either alone or in combination with a genetic alteration that increases the availability of ATP, attenuation of one or more NAD(P)H dehydrogenases or NAD(P)H:quinine oxidoreductases selected from Ndh-II, WrbA, YhdH, YieF, YtfG, Qor and MdaB, attenuation of one or more ubiquinol oxidases selected from cytochrome bd-I oxidase, cytochrome bd-II oxidase and quinol monooxygenase or attenuation of one or more NAD(P)H dehydrogenases and/or NAD(P)H:quinine oxidoreductases selected from the group consisting of Ndh-II, WrbA, YhdH, YieF, YtfG, Qor and MdaB and/or attenuation of one or more ubiquinol oxidase selected from the group consisting of cytochrome bd-I oxidase, cytochrome bd-II oxidase and quinol monooxygenase.

The non-naturally occurring microbial organism having a YciA hydrolase attenuation and a metabolically engineered pathway for producing a bioderived compound from a TCA cycle intermediate or TCA cycle substrate can include, either alone or in combination with a genetic alteration that increases the availability of ATP, attenuation of one or more menaquinol biosynthetic enzymes or attenuation one or more dimethylmenaquinol biosynthetic enzymes.

The non-naturally occurring microbial organism having a YciA hydrolase attenuation and a metabolically engineered pathway for producing a bioderived compound from a TCA cycle intermediate or TCA cycle substrate can include, either alone or in combination with a genetic alteration that increases the availability of ATP, a genetic alteration that increases expression of a phosphoenoylpyruvate carboxykinase (PEPCK) in the microbial organism Increased expression of PEPCK can be from increased expression of an exogenous nucleic acid encoding PEPCK.

The non-naturally occurring microbial organism having a YciA hydrolase attenuation and a metabolically engineered pathway for producing a bioderived compound from a TCA cycle intermediate or TCA cycle substrate can include, either alone or in combination with a genetic alteration that increases the availability of ATP, attenuation of a phosphoenoylpyruvate carboxylase (PPC) in the microbial organism. In another embodiment, the microbial organism can further comprise a genetic alteration that increases expression of a phosphoenoylpyruvate carboxykinase (PEPCK), phosphoenolpyruvate carboxylase (PPC), or a combination thereof in the microbial organism. Such a microbial organism can further comprise attenuation of a pyruvate kinase or glucose phosphotransferase system (PTS). In yet another embodiment, the non-naturally occurring microbial organism can further comprise attenuation of protein encoding ClpA, pyruvate kinase or glucose phosphotransferase system (PTS) (see Examples).

Given the teachings and guidance provided herein, those skilled in the art will understand that any of the above combinations of genetic alterations can be further combined with any single or multiple other genetic alteration described herein.

In a further exemplary embodiment, the invention provides a non-naturally occurring microbial organism having attenuation of a YciA CoA hydrolase and having an exogenous nucleic acid encoding a pyridine nucleotide transhydrogenase. The pyridine nucleotide transhydrogenase can be pntAB.

The non-naturally occurring microbial organism having attenuation of a YciA CoA hydrolase and having an exogenous nucleic acid encoding a pyridine nucleotide transhydrogenase can further include, for example, a genetic alteration that increases the availability of ATP in the microbial organism. The genetic alteration can be, for example, increased expression of NADH dehydrogenase Ndh-I, cytochrome bo oxidase or both NADH dehydrogenase Ndh-I and cytochrome bo oxidase and can include, for example, expression of an exogenous nucleic acid encoding the NADH dehydrogenase Ndh-I (nuo), cytochrome bo oxidase (cyoABCDE) or both NADH dehydrogenase Ndh-I (nuo) and cytochrome bo oxidase (cyoABCDE).

The non-naturally occurring microbial organism having attenuation of a YciA CoA hydrolase and having an exogenous nucleic acid encoding a pyridine nucleotide transhydrogenase can include, either alone or in combination with a genetic alteration that increases the availability of ATP, attenuation of one or more NAD(P)H dehydrogenases and/or NAD(P)H:quinine oxidoreductases selected from Ndh-II, WrbA, YhdH, YieF, YtfG, Qor and MdaB, attenuation of one or more ubiquinol oxidases selected from cytochrome bd-I oxidase, cytochrome bd-II oxidase and quinol monooxygenase or a attenuation of one or more NAD(P)H dehydrogenases and/or NAD(P)H:quinine oxidoreductases selected from the group consisting of Ndh-II, WrbA, YhdH, YieF, YtfG, Qor and MdaB and attenuation of one or more ubiquinol oxidases selected from the group consisting of cytochrome bd-I oxidase, cytochrome bd-II oxidase and quinol monooxygenase.

The non-naturally occurring microbial organism having attenuation of a YciA CoA hydrolase and having an exogenous nucleic acid encoding a pyridine nucleotide transhydrogenase can include, either alone or in combination with a genetic alteration that increases the availability of ATP, attenuation of one or more menaquinol biosynthetic enzymes, attenuation of one or more dimethylmenaquinol biosynthetic enzymes or attenuation of one or more menaquinol biosynthetic enzymes and attenuation of one or more dimethylmenaquinol biosynthetic enzyme.

The non-naturally occurring microbial organism having an attenuation of a YciA CoA hydrolase and having an exogenous nucleic acid encoding a pyridine nucleotide transhydrogenase can include, either alone or in combination with a genetic alteration that increases the availability of ATP, a genetic alteration that increases expression of a phosphoenoylpyruvate carboxykinase (PEPCK) in the microbial organism. Increased expression of PEPCK can be from increased expression of an exogenous nucleic acid encoding PEPCK.

The non-naturally occurring microbial organism having attenuation of a gene encoding a YciA CoA hydrolase and having an exogenous nucleic acid encoding a pyridine nucleotide transhydrogenase can include, either alone or in combination with a genetic alteration that increases the availability of ATP, attenuation of a phosphoenoylpyruvate carboxylase (PPC) in the microbial organism. In another embodiment, the microbial organism can further comprise a genetic alteration that increases expression of a phosphoenoylpyruvate carboxykinase (PEPCK), phosphoenolpyruvate carboxylase (PPC), or a combination thereof in the microbial organism. Such a microbial organism can further comprise attenuation of a pyruvate kinase or glucose phosphotransferase system (PTS). In yet another embodiment, the non-naturally occurring microbial organism can further comprise attenuation of protein encoding ClpA, pyruvate kinase or glucose phosphotransferase system (PTS) (see Examples).

Given the teachings and guidance provided herein those skilled in the art will understand that any of the above combinations of genetic alterations can be further combined with any single or multiple other genetic alteration described herein.

In yet another exemplary embodiment, the invention provides a non-naturally occurring microbial organism having a genetic alteration that increases expression of a NADH dehydrogenase Ndh-I (nuo), cytochrome bo oxidase (cyoABCDE) or both NADH dehydrogenase Ndh-I (nuo) and cytochrome bo oxidase (cyoABCDE).

The non-naturally occurring microbial organism can further include attenuation of one or more endogenous nucleic acids encoding a NAD(P)H dehydrogenases and/or NAD(P)H:quinine oxidoreductases selected from Ndh-II, WrbA, YhdH, YieF, YtfG, Qor and MdaB, attenuation of one or more ubiquinol oxidases selected from cytochrome bd-I oxidase, cytochrome bd-II oxidase and quinol monooxygenase or attenuation of one or more NAD(P)H dehydrogenases and/or NAD(P)H:quinine oxidoreductases selected from the group consisting of Ndh-II, WrbA, YhdH, YieF, YtfG, Qor and MdaB and attenuation of one or more ubiquinol oxidase selected from the group consisting of cytochrome bd-I oxidase, cytochrome bd-II oxidase and quinol monooxygenase.

The non-naturally occurring microbial having a genetic alteration that increases expression of a NADH dehydrogenase Ndh-I (nuo), cytochrome bo oxidase (cyoABCDE) or both NADH dehydrogenase Ndh-I (nuo) and cytochrome bo oxidase (cyoABCDE) can further include, for example, attenuation of one or more menaquinol biosynthetic enzyme, attenuation of one or more dimethyl menaquinol biosynthetic enzymes or attenuation of one or more menaquinol biosynthetic enzymes and attenuation of one or more dimethyl menaquinol biosynthetic enzyme.

The non-naturally occurring microbial organism having a genetic alteration that increases expression of NADH dehydrogenase Ndh-I (nuo), cytochrome bo oxidase (cyoABCDE) or both NADH dehydrogenase Ndh-I (nuo) and cytochrome bo oxidase (cyoABCDE) can further include, for example, a genetic alteration that increases expression of a phosphoenoylpyruvate carboxykinase (PEPCK) in the microbial organism. Increased expression of PEPCK can be from increased expression of an exogenous nucleic acid encoding PEPCK.

The non-naturally occurring microbial organism having a genetic alteration that increases expression of a NADH dehydrogenase Ndh-I (nuo), cytochrome bo oxidase (cyoABCDE) or both NADH dehydrogenase Ndh-I (nuo) and cytochrome bo oxidase (cyoABCDE) can further include, for example, attenuation of a phosphoenoylpyruvate carboxylase (PPC) in the microbial organism. In another embodiment, the microbial organism can further comprise a genetic alteration that increases expression of a phosphoenoylpyruvate carboxykinase (PEPCK), phosphoenolpyruvate carboxylase (PPC), or a combination thereof in the microbial organism. Such a microbial organism can further comprise attenuation of a pyruvate kinase or glucose phosphotransferase system (PTS). In yet another embodiment, the non-naturally occurring microbial organism can further comprise attenuation of protein encoding ClpA, pyruvate kinase or glucose phosphotransferase system (PTS) (see Examples). In another embodiment, the non-naturally occurring microbial organism can further comprise a genetic alteration selected from attenuation of the protein encoded by cydA or cyB and/or pykF, a genetic alteration that increases expression of pntAB, or a combination thereof.

Given the teachings and guidance provided herein those skilled in the art will understand that any of the above combinations of genetic alterations can be further combined with any single or multiple other genetic alteration described herein.

In still another exemplary embodiment, the invention provides a non-naturally occurring microbial organism having attenuation of one or more NAD(P)H dehydrogenases and/or NAD(P)H:quinine oxidoreductases selected from Ndh-II, WrbA, YhdH, YieF, YtfG, Qor and MdaB (i.e., a non-Ndh-I NADH dehydrogenase), attenuation of one or more ubiquinol oxidases selected from cytochrome bd-I oxidase, cytochrome bd-II oxidase and quinol monooxygenase (i.e., a non-cytochrome bo oxidase) or attenuation of one or more NAD(P)H dehydrogenases and/or NAD(P)H:quinine oxidoreductases selected from the group consisting of Ndh-II, WrbA, YhdH, YieF, YtfG, Qor and MdaB and attenuation of one or more ubiquinol oxidases selected from the group consisting of cytochrome bd-I oxidase, cytochrome bd-II oxidase and quinol monooxygenase.

The non-naturally occurring microbial organism having attenuation of one or more non-Ndh-I NADH dehydrogenase and/or a non-cytochrome bo oxidase can further include, for example, attenuation of one or more menaquinol biosynthetic enzymes, attenuation of one or more dimethylmenaquinol biosynthetic enzymes or attenuation of one or more menaquinol biosynthetic enzymes and attenuation of one or more dimethylmenaquinol biosynthetic enzyme.

The non-naturally occurring microbial organism having an attenuation of one or more non-Ndh-I NADH dehydrogenase and/or a non-cytochrome bo oxidase can further include, for example, a genetic alteration that increases expression of a phosphoenoylpyruvate carboxykinase (PEPCK) in the microbial organism. Increased expression of PEPCK can be from increased expression of an exogenous nucleic acid encoding PEPCK.

The non-naturally occurring microbial organism having an attenuation of one or more non-Ndh-I NADH dehydrogenase and/or a non-cytochrome bo oxidase can further include, for example, attenuation of a phosphoenoylpyruvate carboxylase (PPC) in the microbial organism. In another embodiment, the microbial organism can further comprise a genetic alteration that increases expression of a phosphoenoylpyruvate carboxykinase (PEPCK), phosphoenolpyruvate carboxylase (PPC), or a combination thereof in the microbial organism. Such a microbial organism can further comprise attenuation of a pyruvate kinase or glucose phosphotransferase system (PTS). In yet another embodiment, the non-naturally occurring microbial organism can further comprise attenuation of protein encoding ClpA, pyruvate kinase or glucose phosphotransferase system (PTS) (see Examples).

Given the teachings and guidance provided herein, those skilled in the art will understand that any of the above combinations of genetic alterations can be further combined with any single or multiple other genetic alteration described herein.

In a further exemplary embodiment, the invention provides a non-naturally occurring microbial organism having an attenuation of one or more menaquinol biosynthetic enzyme, attenuation of one or more dimethylmenaquinol biosynthetic enzyme or attenuation of one or more menaquinol biosynthetic enzymes and attenuation of one or more dimethylmenaquinol biosynthetic enzymes.

The non-naturally occurring microbial organism having an attenuation of one or more endogenous nucleic acids encoding a menaquinol and/or a dimethylmenaquinol biosynthetic enzyme can further include, for example, a genetic alteration that increases expression of a phosphoenoylpyruvate carboxykinase (PEPCK) in the microbial organism. Increased expression of PEPCK can be from increased expression of an exogenous nucleic acid encoding PEPCK.

The non-naturally occurring microbial organism having an attenuation of one or more menaquinol and/or a dimethylmenaquinol biosynthetic enzymes can further include, for example, attenuation of a phosphoenoylpyruvate carboxylase (PPC) in the microbial organism. In another embodiment, the microbial organism can further comprise a genetic alteration that increases expression of a phosphoenoylpyruvate carboxykinase (PEPCK), phosphoenolpyruvate carboxylase (PPC), or a combination thereof in the microbial organism. Such a microbial organism can further comprise attenuation of a pyruvate kinase or glucose phosphotransferase system (PTS). In yet another embodiment, the non-naturally occurring microbial organism can further comprise attenuation of protein encoding ClpA, pyruvate kinase or glucose phosphotransferase system (PTS) (see Examples).

Given the teachings and guidance provided herein, those skilled in the art will understand that any of the above combinations of genetic alterations can be further combined with any single or multiple other genetic alteration described herein.

By way of example regarding the various combinations and permutations disclosed and exemplified above, the invention further provides a non-naturally occurring microbial organism of any of the above exemplary embodiments including where the microbial organism is selected from bacteria, yeast, fungus or another microorganism applicable to a fermentation process. The non-naturally occurring microbial organism can be a bacteria and the bacteria can be *Escherichia coli*.

Additionally provided by way of example regarding the various combinations and permutations disclosed and exemplified herein is a non-naturally occurring microbial organism including a genetic alteration selected from: (1) attenuation of cydA or cydB, and one or more of a genetic alteration selected from (a) a genetic alteration that increases expression of a protein encoded by pntAB; (b) attenuation of the protein encoded by pykF; (c) attenuation of the protein encoded by sucCD; (d) attenuation of the protein encoded by yciA; (e) a genetic alteration that increases expression of a protein encoded by ackA and a protein encoded by pta; (f) a genetic alteration that increases expression of a protein encoded by cyoB; (g) attenuation of the protein encoded by pykA; (h) attenuation of the protein encoded by arcA; (i) attenuation of the protein encoded by crr; (j) attenuation of the protein encoded by clpA; and (k) attenuation of the protein encoded by menC; and (2) a genetic alteration selected from (a) attenuation of the proteins encoded by sucCD and yciA; (b) attenuation of the proteins encoded by sucCD and yciA, and having a genetic alteration that increases expression of a protein encoded by pntAB; (c) attenuation of the proteins encoded by sucCD and yciA, and having a genetic alteration that increases expression of a protein encoded by cyoB; (d) attenuation of the proteins encoded by sucCD, yciA and cydA or cydB, and having a genetic alteration that increases expression of a protein encoded by cyoB; (e) attenuation of the proteins encoded by sucCD, yciA and menC and having a genetic alteration that increases expression of a protein encoded by cyoB, (f) attenuation of the proteins encoded by sucCD, yciA, cydA or cydB and menC and having a genetic alteration that increases expression of a protein encoded by cyoB; (g) attenuation of the proteins encoded by sucCD and cydA or cydB; (h) attenuation of the proteins encoded by sucCD and cydA or cydB and pykF; (i) attenuation of the proteins encoded by sucCD and cydA or cydB, and having a genetic alteration that increases expression of a protein encoded by pntAB; (j) attenuation of the proteins encoded by sucCD and cydA or cydB and pykF, and having a genetic alteration that increases expression of a protein encoded by pntAB; (k) attenuation of the proteins encoded by sucCD, yciA and cydA or cydB; (l) attenuation of the proteins encoded by sucCD, yciA and cydA or cydB and pykF; (m) attenuation of the proteins encoded by sucCD, yciA and cydA or cydB, and having a genetic alteration that increases expression of a protein encoded by pntAB; (n) attenuation of the proteins encoded by sucCD, yciA and cydA or cydB and pykF, and having a genetic alteration that increases expression of a protein encoded by pntAB; (o) attenuation of the proteins encoded by sucCD, yciA, and cydA or cydB and menC; (p) attenuation of the proteins encoded by sucCD, yciA and cydA or cydB and menC, and having a genetic alteration that increases expression of a protein encoded by pntAB; (q) attenuation of the proteins encoded by sucCD and pykF, and having a genetic alteration that increases expression of a protein encoded by pntAB; (r) attenuation of the protein encoded by clpA; (s) attenuation of the protein encoded by menC; (t) attenuation of the protein encoded by menC and cydA or cydB; (u) attenuation of the protein encoded by pykF and/or pykA; (v) having a genetic alteration that increases expression of a protein encoded by pntAB; (w) attenuation of cydA or cydB and sucCD, arcA and crr, and having a genetic alteration that increases expression of a protein encoded by ackA and pta; (x) attenuation of cydA or cydB and arcA; (y) attenuation of cydA or cydB, and having a genetic alteration that increases expression of a protein encoded by pntAB; (z) attenuation of cydA or cydB and pykF; and (aa) attenuation of cydA or cydB and pykF, and having a genetic alteration that increases expression of a protein encoded by pntAB.

The above non-naturally occurring microbial organism can further include a metabolically engineered pathway for producing a bioderived compound from a TCA cycle intermediate or a TCA cycle substrate. The bioderived compound can be of 4-hydroxybutyrate (4HB), 1,4-butanediol (1,4-BDO), 1,3-butanediol (1,3-BDO), polyhydroxylbutanoate (PHB), butadiene, adipate, 6-aminocaproate, caprolactam, methacrylic acid, isopropanol, long chain alcohols, hexamethylenediamene, methyl methacrylate, butanol, 3-butene-1-ol, 3-butene-2-ol and crotyl-alcohol. Additionally the microbial organism can be a bacteria and the bacteria can be *Escherichia coli*.

As described herein, an attenuation is a genetic alteration that renders the encoded gene product inactive or reduced in activity. In some embodiments, the attenuation can include a complete gene deletion. In some embodiments other methods to attenuate, including methods to disrupt a gene include, for example, frameshifting by omission or addition of oligonucleotides or by mutations that render the gene inoperable. One skilled in the art will recognize the usefulness of gene deletions, however, because of the stability it confers to the non-naturally occurring organism from reverting to a parental phenotype in which the attenuation has not occurred. Although exemplified herein as metabolic alterations, in particular one or more attenuations, it is understood that any attenuation that reduces or prevents the activity of the referenced metabolic activity can be introduced into a host microbial organism, as desired.

The non-naturally occurring microbial organisms of the invention having one or more attenuations as described herein can be produced by attenuation or gene disruption as described herein. Briefly, given the teachings and guidance provided herein, those skilled in the art will understand that to introduce a metabolic alteration such as attenuation of an enzyme, it can be necessary to disrupt the catalytic activity of the one or more enzymes involved in the reaction. Alternatively, a genetic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art.

Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be attenuated by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding an enzyme of a targeted metabolic reaction can be practiced in the methods of the invention and incorporated into the non-naturally occurring microbial organisms of the invention in order to achieve reduced carbon flux from succinyl-CoA to succinate through an oxidative TCA cycle. Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999)). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); and addition of drugs or other chemicals that reduce or disrupt enzymatic activity such as an enzyme inhibitor, an antibiotic or a target-specific drug. One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2): e1002474 (2012)); flipping the orientation of a transposable element or promoter region so as to modulate gene expression of an adjacent gene (Wang et al., Genetics 120(4):875-885 (1988); Hayes, Annu. Rev. Genet 37:3-29 (2003); in a diploid organism, deleting one allele resulting in loss of heterozygosity (Daigaku et al., *Mutation Research/Fundamental and Molecular Mechanisms of Mutagenesis* 600(1-2)177-183 (2006)); introducing nucleic acids that increase RNA degradation (Houseley et al., *Cell,* 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2):125-131 (2005); modifying regions outside the coding sequence, such as introducing secondary structure into an untranslated region (UTR) to block translation or reduce efficiency of translation (Ringner et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5):883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); or introducing translational regulatory elements involving RNA structure that can prevent or reduce translation that can be controlled by the presence or absence of small molecules (Araujo et al., *Comparative and Functional Genomics*, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911 (1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understood that a determination of what is the appropriate technique for a given host can be readily made by one skilled in the art.

It is understood that a genetic alteration that increases expression of a desired enzyme is generally carried out by introducing into the microbial organism an exogenous nucleic acid encoding the desired enzyme. However, given the teachings and guidance provided herein, those skilled in the art will understand that a genetic alteration to increase expression also can include modifications of a gene expression or regulatory region of an endogenous gene. Such regions include, for example, a promoter, enhancer and/or other regulatory region such as a sequence that alters stability or half-life of the encoding nucleic acid. For example, a stronger promoter and/or an enhancer can be included or substituted into the endogenous gene to achieve increased expression using methods well known in the art. By way of illustration, the invention will be described by reference to increasing expression through introduction of an exogenous encoding nucleic acid. However, such teachings are equally applicable to increasing expression by increasing the strength of expression and regulatory elements. Similarly, a genetic alteration that attenuates expression can relate to modifications that alter the activity of an encoded protein or can relate to regulatory molecules at the transcriptional or protein level, as disclosed herein.

The non-naturally occurring microbial organisms of the invention having exogenous nucleic acids encoding an enzyme or protein described herein can be produced by introducing expressible nucleic acids encoding one or more of the enzymes or proteins participating in one or more of the genetic alterations disclosed herein. Exemplary genetic alterations for introducing an encoding nucleic acid include, for example, introduction of one or more exogenous nucleic acids encoding a pyridine nucleotide transhydrogenase, a pathway enzyme for biosynthesis of a bioderived compound, NADH dehydrogenase Ndh-I, cytochrome bo oxidase and/or phosphoenoylpyruvate carboxykinase. Depending on the host microbial organism chosen for biosynthesis of a bioderived compound, nucleic acids for one or more of the genetic alterations disclosed herein relating to expression of an exogenous nucleic acid encoding can be expressed.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Similarly, it is understood by those skilled in the art that a host organism can be selected based on desired characteristics for introduction of one or more attenuations to reduce carbon flux from succinyl-CoA to succinate through an oxidative TCA cycle or to weaken, reduce or diminish the activity of other enzymes or proteins of the invention. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will reduce carbon flux from succinyl-CoA to succinate through an oxidative TCA cycle.

Sources of encoding nucleic acids for an enzyme or protein disclosed herein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Mannheimia succiniciproducens, Anaerobiospirillum succiniciproducens, Actinobacillus succinogenes, Megathyrsus maximus, Haemophilus influenza, Methylobacterium extorquens, Corynebacterium glutamicum, Rattus norvegicus, Homo sapiens, Mus musculus, Pseudomonas aeruginosa, Mycobacterium tuberculosis, Acidaminococcus fermentans, Clostridium symbiosum, Fusobacterium nucleatum, Clostridium kluyveri, Trichomonas vaginalis, Trypanosoma brucei, Clostridium aminobutyricum, Porphyromonas gingivalis* W83, *Acetobacter aceti, Clostridium saccharoperbutylacetonicum, Citrobacter youngae, Salmonella enteric, Yersinia intermedia, Oxalobacter formigenes, Pseudomonas putida, Acinetobacter* sp. ADP1, *Streptomyces coelicolor, Pseudomonas knackmussii, Helicobacter pylori, Bacillus subtilis, Sus scrofa, Roseburia* sp. A2-183, *Roseburia intestinalis, Roseburia inulinivorans, Eubacterium rectale, Clostridium propionicum, Clostridium novyi* NT, *Clostridium beijerinckii, Clostridium botulinum, Haloarcula marismortui, Archaeoglobus fulgidus, Archaeoglobus fulgidus, Pyrobaculum aerophilum* str. IM2, *Rhizobium leguminosarum*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing reduced carbon flux from succinyl-CoA to succinate through an oxidative TCA cycle described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative metabolic enzyme or protein exists in species not explicitly disclosed herein, the desired activity can be conferred onto the host species by, for example, exogenous expression of a paralog or paralogs from one or more species that catalyzes a similar, yet non-identical metabolic reaction to replace the referenced reaction. Because certain differences among metabolic reactions exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate genetic alterations to those exemplified herein to construct a microbial organism in a species of interest that will exhibit the desired metabolic activity.

A nucleic acid molecule encoding an enzyme or protein described herein can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity to a nucleic acid described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding an enzyme or protein described herein can have at least a certain sequence identity to a nucleotide sequence disclosed herein. Accordingly, in some aspects of the invention, a nucleic acid molecule encoding an enzyme or protein described herein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity, or is identical, to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

Methods for constructing and testing the expression levels of a non-naturally occurring hosts that have reduced carbon flux from succinyl-CoA to succinate through an oxidative TCA cycle can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more protein or enzyme encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

The invention provides a method of producing a bioderived compound. The method includes culturing a non-naturally occurring microbial organism having one or more metabolic modifications described herein and a metabolically engineered pathway for producing a bioderived compound. The metabolic modifications include attenuations and/or genetic alterations such as expression of an exogenous encoding nucleic acid as described herein. The metabolically engineered pathway can utilize a TCA cycle intermediate or TCA cycle substrate for bioderived compound production or utilize a substrate derived from a non-TCA cycle metabolic pathway.

In one embodiment, the invention provides a method of producing a bioderived compound. The method includes culturing a non-naturally occurring microbial organism having a first attenuation of a succinyl-CoA synthetase and at least a second attenuation of a succinyl-CoA converting enzyme or a gene encoding a succinate producing enzyme within a multi-step pathway having a net conversion of succinyl-CoA to succinate and having a metabolically engineered pathway for producing a bioderived compound from a TCA cycle intermediate or TCA cycle substrate for a sufficient period of time under conditions sufficient to produce said bioderived compound. The non-naturally occurring microbial organism can additionally include one or more metabolic modifications, including up to all metabolic modifications described herein.

In addition, the invention provides a method for decreasing conversion from succinyl-CoA to succinate in a non-naturally occurring microbial organism, decreasing production of excess $CO_2$ in a non-naturally occurring microbial organism, decreasing flux through an oxidative TCA cycle in a non-naturally occurring microbial organism, decreasing oxygen utilization per non-naturally occurring microbial organism and/or increasing availability of ATP in a non-naturally occurring microbial organism. The method includes culturing a non-naturally occurring microbial organism having one or more metabolic modifications as described herein. The non-naturally occurring microbial organism can be used as a reference or control for the generation of an organism having a metabolically engineered pathway for production of a bioderived compound, for example.

Suitable purification and/or assays to test for the engineered one or more genetic alterations described herein can be performed using well known methods. Suitable replicates such as triplicate cultures can be grown for each engineered strain to be tested. For example, metabolic product and byproduct formation of the engineered reactions in host can be monitored. For example, the product and/or any intermediates can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of an engineered metabolic product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous nucleic acid sequences can also be assayed using methods well known in the art. Such methods are exemplified in the Examples below. Other methods well known in the art also can be employed to assay the production of one or more metabolic activities described herein.

The products from any of the genetic alterations described herein including, for example, a bioderived compound can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete, for example, a bioderived compound of the invention. For example, a host microbial organism producing a bioderived compound of the invention can be cultured for the biosynthetic production of such compound. Accordingly, in some embodiments, the invention provides culture medium having a bioderived compound described herein. In some aspects, the culture medium can also be separated from the non-naturally occurring microbial organisms of the invention that produced the bioderived compound. Methods for separating a microbial organism from culture medium are well known in the art. Exemplary methods include filtration, flocculation, precipitation, centrifugation, sedimentation, and the like.

For the production of a bioderived compound, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high bioderived compound yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example: sugars such as glucose, xylose, arabinose, galactose, mannose, fructose, sucrose and starch; or glycerol, and it is understood that a carbon source can be used alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for decreasing conversion from succinyl-CoA to succinate, decreasing production of excess $CO_2$, decreasing flux through an oxidative TCA cycle, decreasing oxygen utilization per microbial organism, or increasing availability of ATP.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving decreasing conversion from succinyl-CoA to succinate, decreasing production of excess $CO_2$, decreasing flux through an oxidative TCA cycle, decreasing oxygen utilization per microbial organism, or increasing availability of ATP includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of a desired product. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of a desired product Generally, and as with non-continuous culture procedures, the continuous and/or near-continuous production of a desired product will include culturing a non-naturally occurring microbial organism of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of a bioderived compound can be utilized in, for example, fed-batch fermentation and batch separation; fed-batch fermentation and continuous separation, or continuous fermentation and continuous separation. Examples of batch and continuous fermentation procedures are well known in the art.

It is understood that modifications which do not substantially affect the activity of the various embodiments of this invention are also provided within the definition of the invention provided herein. Accordingly, the following examples are intended to illustrate but not limit the present invention.

Example I

Deletion of YciA, YbfF, YdiI

This example describes deletion of three endogenous CoA hydrolases in host strain 6286 and the effect on succinate production in the host strain 6286.

Cultivation Conditions for 96 Well-Plates.

All the cultures in 96 well-plates were grown in 1.2 ml of M9 medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 10 mM NaHCO$_3$ and 100 mM MOPS to improve the buffering capacity. Carbon source in the form of 5% glucose was also added. Microaerobic conditions were obtained by covering the plates with two gas-permeable adhesive seals. The edges of the seal were taped to minimize evaporation. All the cultures were grown at 37° C. Analytical methods for quantifying biomass, BDO, 4HB, and succinate were reported in US20140030779 and Yim et al., *Nature Chemical Biology* 7:445-452 (2011).

To test the impact of endogenous CoA hydrolases on succinyl-CoA to succinate conversion, yciA, ybfF and ydiI were deleted in host strain 6286. Strain 6619 was derived from strain 6286 with yciA deleted. Strain 6620 was derived from strain 6286 with ydiI deleted. Strain 6618 was derived from strain 6286 with ybfF deleted.

Strain 6286 is derived from strain 6025, with the additional deletion of succinate dehydrogenase (sdhA). Strain 6025 was derived from strain ECKh-432 whose construction is described in US20110045575, US20140030779, and Yim et al., *Nature Chemical Biology* 7:445-452 (2011). Notable modifications in the ECKh-432 base strain include deletions in adhE, ldhA, pflB, and mdh. Strain 6025 also contains chromosomally integrated copies of genes that convert succinyl-CoA to BDO. These genes include a CoA-dependant succinate semialdehyde dehydrogenase, 4-hydroxybutyrate dehydrogenase, a 4-hydroxybutyryl-CoA reductase (ALD), a 4-hydroxybutyryaldehyde reductase (ADH) and a 4-hydroxybutyryl-CoA transferase. Strain 6025 also contains deletions in four native alcohol dehydrogenase genes adhP, yqhD, yahK, and yjgB. This strain also has deletions of cytochrome oxidases, cyoABCD and appBC, succinyl-CoA synthetase (sucCD), the glycoxylate shunt (aceBAK), a prophage integration site (yciI) and flagellar biosynthesis genes (flhCD,motA), the predicted transporter (yebQ), acyl-CoA hydrolases (ybgC, tesB, ybhC), aspartate-ammonia lyase (aspA), the ferrichrome/phage/antibiotic outer membrane porin (fhuA), glutamate synthase (gltBD), a low specificity threonine aldolase (ltaE), PEP carboxykinase (pckA), the glycine cleavage system component (gcvT), the maltose outer membrane porin/phage lambda receptor protein (lamB), and the fimbriae genes (fimABCDEFGHI). In addition, the native promoter of ppc was replaced with a stronger constitutive promoter. Strain 6025 also contains an inactivated arcA gene (Silverman et al., *J Bacteriol.* 173 (18):5648-5652 (1991)). Several native genes are chromosomally overexpressed: ackA, pta, sucA, sucB and lpdA.

Deletions of yciA, ydiI and ybfF were achieved using a two-step double-crossover homologous recombination method as described previously (Yim et al, *Nature Chem Biol* 7:445-52 (2011); US20140030779). Recombination was catalyzed via expression of the Lambda phage Red genes from pRED-Amp (Gene Bridges, Heidelberg, Germany). Genes encoding levansucrase (sacB) from *Bacillus subtilis* and kanamycin resistance were integrated into the chromosome. Kanamycin was used to select for successful integrants. In a second double-crossover homologous recombination step, the integrated sequence containing the levansucrase gene and kanamycin resistance gene was replaced with an appropriate DNA sequence (deletion or insertion or mutation) and sucrose resistant clones were selected for kanamycin sensitivity. DNA sequences used in the homologous recombination steps outlined above were constructed via standard molecular biological techniques.

Upon recombination, the chromosomal region encompassing the modification was PCR amplified and sequenced in order to verify that the expected modification occurred as planned. Flanking regions (between 500-1000 nt) covering any regulatory sequence were therefore sequence verified.

The following primers were used to confirm the yciA, ydiI and ybfF deletions:

| Primer Designation | Primer Sequence | SEQ ID NO |
|---|---|---|
| yciA F1 | AGCCAGGCAGTGGGATTGTG | 1 |
| yciA R1 | GGCAAACATCTACATCGCATTC | 2 |
| ydiI F1 | CGAATGAATGGCTGGCAAG | 3 |
| ydiI R1 | CCAGACGCCAGGCAAAGTAG | 4 |
| ybfF F1 | TAAACGATGCCCTGACTACGC | 5 |
| ybfF R1 | CGGATAGCGTCAAGCCTGG | 6 |

As a result, the following nucleotides were deleted: 1,309, 961-1,310,181 (yciA), 711,267-712,043 (ybfF) and 1,763, 374-1,763,651 (ydiI).

Strain 6286 has several genetic modifications which disrupt or alter the TCA cycle. Inactivation of arcA enables increased flux through the oxidative TCA cycle. Disrupting the ArcA regulator also increases the expression level of cytochrome oxidases (both cyo and cyd) relative to an ArcA-wild type strain. Disrupted sucCD (succinyl-CoA synthetase) reduces TCA cycle flux from succinyl-CoA to succinate. The TCA cycle was further disrupted by deletion of succinate dehydrogenase, which converts succinate to fumarate. Table 19 shows the BDO and byproduct production in 96-well plates from the strain 6286 with and without yciA. Endogenous succinyl-CoA to succinate activity results in the accumulation of succinate in this strain. Deletion of yciA in strain 6286 resulted in reduced production of succinate, indicating reduced succinyl-CoA to succinate activity. Additionally, higher BDO and 4HB were observed in cells with yciA deleted, supporting increased flux into the BDO pathway in this strain.

TABLE 19

BDO production in strain 6286 with and without deletion of yciA, ybfF, and ydiI. Four replicate cultures were shown. All the concentrations were in mM and were measured after 24 hours of culture time in 96-well plates.

| Strain | Modification | OD | BDO | 4HB | Succ | BDO/Succ |
|---|---|---|---|---|---|---|
| 6286 | | 3.58 | 71.0 | 8.9 | 19.0 | 3.7 |
| 6286 | | 3.57 | 74.6 | 9.7 | 18.8 | 4.0 |
| 6286 | | 3.6 | 77.4 | 8.9 | 18.7 | 4.1 |
| 6286 | | 3.42 | 70.8 | 9.9 | 19.0 | 3.7 |
| 6619 | YciA deletion | 3.59 | 86.4 | 15.1 | 6.4 | 13.4 |
| 6619 | YciA deletion | 3.43 | 82.0 | 14.2 | 6.5 | 12.5 |
| 6619 | YciA deletion | 3.66 | 90.1 | 14.9 | 6.9 | 13.0 |
| 6619 | YciA deletion | 3.77 | 88.9 | 15.4 | 6.7 | 13.2 |
| 6618 | YbfF deletion | 4.05 | 59.4 | 7.7 | 38.4 | 1.4 |
| 6618 | YbfF deletion | 3.89 | 64.4 | 8.9 | 34.4 | 1.9 |
| 6618 | YbfF deletion | 3.87 | 52.4 | 8.5 | 40.6 | 1.3 |
| 6618 | YbfF deletion | 3.72 | 58.3 | 7.9 | 39.0 | 1.5 |
| 6620 | YdiI deletion | 3.86 | 73.4 | 10.3 | 23.4 | 3.1 |
| 6620 | YdiI deletion | 3.52 | 89.2 | 10.6 | 24.1 | 3.7 |
| 6620 | YdiI deletion | 4.04 | 77.9 | 10.5 | 25.2 | 3.1 |
| 6620 | YdiI deletion | 3.49 | 81.7 | 9.2 | 24.9 | 3.3 |

Example II

Reduction of Excess COQ YciA Deletion

This example describes growth phase 13C flux analysis of strains with and without yciA, demonstrating that the deletion yciA in a strain with disrupted sucCD results in reduced succinyl-CoA to succinate flux and reduced excess $CO_2$. The example also shows that altering the energetic efficiency of the respiratory chain can improve the growth rate of YciA deleted strains.

Growth phase 13C flux analysis experimental and computational methods are known in the art and are described in Yang, T. H., 13C-*Based Metabolic Flux Analysis: Fundamentals and Practice*, in Systems Metabolic Engineering: Methods and Protocols 297-334 (Alper, H. S. ed., 2013). In summary, cultures were grown in shake-flasks in M9 minimal medium supplemented with uniformly labeled $^{13}$C-glucose. Cultures were sampled in mid-log phase exponential growth. Metabolic products (biomass constituents and secreted metabolic products) were isolated and quantified by mass spectrometry. From concentration measurements, cumulative yield coefficients were calculated for all the extracellular species produced and consumed by the cells, including biomass and $CO_2$. The 13C labeling patterns of the metabolic products were analyzed by gas chromatography-mass spectrometry (GCMS) as described previously (Fischer and Sauer, *Eur. J. Biochem.* 270:880-891 (2003)). Using a reaction network comprising central metabolic and BDO-producing reactions, a numerical optimization was performed to estimate in vivo fluxes from the experimentally obtained metabolite concentrations and 13C labeling patterns.

Growth phase 13C flux analysis was performed to evaluate the impact of yciA on central metabolic pathways. The strains used in this example are 6025 (yciA+), 6616 (6025 ΔyciA), and 6729 (6025+cyoABCD ΔyciA). The distribution of flux (per glucose) among central metabolic pathways for strains 6025, 6616, and 6729 is shown in Table 20.

TABLE 20

The distribution of flux (per glucose) among central metabolic pathways for strains 6025, 6616, and 6729.

| Strain | Glucose uptake | Pentose Phosphate Pathway (per Glc) | Glycolysis (per Glc) | Succinyl-CoA to Succinate (per Glc) | Excess $CO_2$ (per Glc) | Growth rate |
|---|---|---|---|---|---|---|
| 6025 | 1 | 0.26 | 0.73 | 0.32 | 2.35 | 0.25 |
| 6616 | 1 | 0.25 | 0.74 | 0.12 | 1.90 | 0.21 |
| 6729 | 1 | 0.26 | 0.73 | 0.15 | 1.89 | 0.24 |

The results show that compared to the 6025 control, flux from succinyl-CoA to succinate in strains 6616 and 6729 was decreased from 32% to 12% and 15%, respectively. Deletion of yciA did not significantly alter flux through the pentose phosphate pathway. Excess $CO_2$ per glucose in 6616 and 6729 was reduced from 2.35 to 1.89-1.90 due to decreased succinyl-CoA to succinate activity.

A comparison of the growth rates of 6025, 6616, and 6729 shows that disruption of yciA and cyo both have significant effect on the growth rate, in the 6025 strain background. The strain with yciA deleted and cyd as the only cytochrome oxidase (6616) grows at a significantly slower rate than the strain in which both cyd and cyo are present (6729). The re-introduction of the more energy-efficient cytochrome oxidase increased the ATP availability per glucose, and partially relieved the ATP shortage caused by the TCA cycle disruption.

Example III

Reduction of Specific Oxygen Uptake in YciA Deletion Strain

This example describes a reduction of specific uptake per cell in strains with and without YciA.

Strains with attenuated TCA cycles are expected to have reduced capacity to respire and utilize oxygen. To evaluate if YciA deletion has an effect on oxygen uptake capacity, a fed-batch aerobic fermentation was performed on strains with and without the YciA deletion. The strains evaluated were 6435 and 6729. Strain 6435 was derived from 6025 with wild-type cyoABCD restored. Strain 6729 was derived from 6435 with yciA deleted.

Fed-batch fermentations were performed with 1 L initial culture volume in 2 L Biostat B+ bioreactors (Sartorius; Cedex France) using M9 minimal medium supplemented with 20 g/L glucose. The temperature was controlled at 35° C., and the pH was controlled at 6.75 using 2 M $NH_4OH$ or $Na_2CO_3$. Cells were grown aerobically and no nutrient limitations were imposed. Oxygen was measured using a Presens Oxy4 dissolved oxygen probe.

Biomass, time, specific oxygen uptake rate (S-OUR) and instantaneous specific molar oxygen uptake rate (ISMOUR) are shown in Table 21. The biomass measurement was calculated from the culture OD, (1 OD equivalent=0.4 g dry cell weight per liter). The instantaneous specific molar oxygen uptake rate is the difference in oxygen uptake rate divided by the difference in biomass divided by the time interval of the measurements.

TABLE 21

Biomass, time, S-OUR and ISMOUR in strains 6729 and 6435.

| Time | BioMass (g) | | S-OUR (mmol/h/g) | | ISMOUR (mmol/h/g) | |
|---|---|---|---|---|---|---|
| | 6729 | 6435 | 6729 | 6435 | 6729 | 6435 |
| 0 | 0.0 | 0.0 | | | | |
| 7 | 2.2 | 2.8 | 3.6 | 4.5 | | |
| 10 | 4.6 | 7.0 | 4.2 | 6.7 | 3.8 | 5.4 |
| 13 | 8.2 | 14.7 | 4.5 | 6.4 | 4.3 | 6.4 |
| 19 | 18.5 | 42.3 | 4.4 | 5.2 | 4.4 | 5.9 |

At all times of the fermentation, strain 6729 demonstrated a reduced specific oxygen uptake rate compared to 6435. The biomass formation rate was also slower in 6729.

Example IV

YciA Deletion Combined with PntAB Overexpression Reduces Excess $CO_2$

This example describes growth phase 13C flux analysis of yciA deletion strains with and without plasmid-based overexpression of transhydrogenase (pntAB).

Development of Expression Vectors for pntAB.

Vector backbones were obtained from Dr. Rolf Lutz of Expressys (expressys.de). The vectors and strains are based on the pZ Expression System described previously (Lutz and Bujard, *Nucleic Acids Res.* 25:1203-1210 (1997)). Spefi- cially, pZS*13luc was obtained and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

lacZalpha-RI (SEQ ID NO: 7)
5'GACGAATTCGCTAGCAAGAGGAGAAGTCGACATGTCCAATTCACTGGC
CGTCGTTTTAC3' lacZalpha 3'BB (SEQ ID NO: 8)
5'-GACCCTAGGAAGCTTTCTAGAGTCGACCTATGCGGCATCAGAGCAG
A-3'.

This generated a fragment with a 5' end of EcoRI site, NheI site, a Ribosomal Binding Site, a SalI site and the start codon. The 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a site after ligation that is not digested by either enzyme), the genes cloned into the vectors could be "Biobricked" together (openwetware.org/wild/Synthetic_Biology:BioBricks). Briefly, this method allows joining an unlimited number of genes into the vector using the same 2 restriction sites, as long as the sites do not appear internal to the genes, because the sites between the genes are destroyed after each addition. Initially, expression was low from these vectors, and they were subsequently modified using the Phusion® Site-Directed Mutagenesis Kit (NEB, Ipswich, Mass.) to insert the spacer sequence AAT-TAA between the EcoRI and NheI sites. This eliminated a putative stem loop structure in the RNA that bound the RBS and start codon.

All vectors have the pZ designation followed by letters and numbers indicating the origin of replication, antibiotic resistance marker and promoter/regulatory unit. The origin of replication is the second letter and is denoted by E for ColE1, A for p15A and S for pSC101 (as well as a lower copy number version of pSC101 designated S*)-based origins. The first number represents the antibiotic resistance marker (1 for Ampicillin, 2 for Kanamycin, 3 for Chloramphenicol). The final number defines the promoter that regulated the gene of interest (1 for PLtetO-1, 2 for PLlacO-1 and 3 for PA1lacO-1) and each of these promoters became activated by its corresponding inducer molecule (pLtetO can be induced by tetracycline; pLlacO-1 and pA1lacO-1 can be induced by IPTG). One base vector, pZS*13S, was further designed.

In addition to the "inducible" promoters mentioned above, a set of "constitutive" promoters were sampled from the Registry (partsregistry.org). Each of these "constitutive" promoters was then introduced into the pZS*13S vector backbone to replace the pA1lacO-1 inducible promoter via Sequence and Ligation Independent Cloning (SLIC) method described previously (Li et al., *Nature Methods* 4:251-256 (2007)). Of these sampled "constitutive" promoters (p100, p104, p105, p107, p108, p111, p115 & p119), experiments were carried out to establish an order of promoter strength that was verified by protein expression levels. For these experiments, p115 was chosen for pntAB expression. To further dial-down protein expression levels of pntAB, the ribosomal binding site (RBS) in between promoter and gene coding sequence was modified accordingly using the RBS calculator (salis.psu.edu/software/).

The SLIC primers used for inserting pntAB into the pZS*13S vector backbone are listed below. The lower case marks the sequences annealing to a vector backbone while the upper case marks the sequences annealing to the coding region of a gene.

1. pntAB

Forward SLIC primer:

(SEQ ID NO: 9)
gaggagaagtcgacATGAACGAACAATATTCCGCATTGCG

Reverse SLIC primer:

(SEQ ID NO: 10)
ggaagctttctagaTTAGCCGGTATTACGCATACCTGCC.

Flux Analysis Results.

Growth phase 13C flux analysis was performed as described previously to evaluate the impact of pntAB overexpression on flux through the pentose phosphate pathway, the succinyl-CoA to succinate reaction and excess $CO_2$ formation. Overexpression of pntAB was expected to decrease flux through the pentose phosphate pathway by generating NADPH at the cost of NADH. The strain used in this example is 6729 (6025+cyoABCD ΔyciA) transformed with one of the following plasmids: (1) pZS*-p115-empty vector, (2) pZS*-p115-6K-RBS-pntAB, (3) pZS*-p115-13K-RBS-pntAB, (4) pZS*-p115-pntAB. Plasmids 2-4 express the membrane-bound transhydrogenase encoded by pntAB at increasing levels, with p115-pntAB being the strongest expression.

The distribution of flux (per glucose) among central metabolic pathways for each strain/plasmid combination is shown in Table 22.

TABLE 22

The distribution of flux (per glucose) among central
metabolic pathways for strain 6729 (6025 +
cyoABCD ΔyciA) transformed with one of the
following plasmids: (1) pZS*-p115-empty vector, (2) pZS*-p115-
6K-RBS-pntAB, (3) pZS*-p115-13K-RBS-pntAB, (4)
pZS*-p115-pntAB.

| Strain | Glucose uptake | Pentose Phosphate Pathway (per Glc) | Glycolysis (per Glc) | Succinyl-CoA to Succinate (per Glc) | Excess $CO_2$ (per Glc) |
|---|---|---|---|---|---|
| 1 | 1 | 0.26 | 0.73 | 0.12 | 1.96 |
| 2 | 1 | 0.19 | 0.80 | 0.11 | 1.84 |
| 3 | 1 | 0.18 | 0.81 | 0.09 | 1.77 |
| 4 | 1 | 0.12 | 0.88 | 0.08 | 1.78 |

Growth phase flux analysis confirmed that pntAB OE decreased excess $CO_2$ by reducing flux through the pentose phosphate pathway and the oxidative TCA cycle (controlled by the succinyl-CoA to succinate reaction).

Example V

Increasing Growth Yield with CydAB Deletion

This example demonstrates that an increased growth yield can be obtained by improving the energetic efficiency of the electron transport chain via cydAB deletion.

The cytochrome bo complex, encoded by the cyo operon, is rendered the predominant cytochrome oxidase complex by deletion of cydAB, which encode the cytochrome bd-I complex. The cytochrome bo complex actively pumps electrons over the membrane and results in an H+/2e− stoichiometry of 4. The cytochrome bd-I complex does not appear to actively pump protons. However, due to the oxidation of the quinol on the periplasmic side of the membrane and subsequent uptake of protons from the cytoplasmic side of the membrane which are used in the formation of water, the net electron transfer results in a H+/2e− stoichiometry of 2. Since cytochrome bo complex has a greater proton translocation stoichiometry than the cytochrome bd-I complex, the energetic efficiency of the electron transport chain can be improved by deletion of cydAB.

Host strain 7032 is similar to 6025 described above. It contains a restored wild-type cyo operon and is sucCD. Host strain 7143 is derived from 7032 but contains a deletion in cydAB. Deletions of cydA and cydB were achieved using a two-step double-crossover homologous recombination method as described in Yim et al. (Yim et al, *Nature Chem Biol* 7:445-52 (2011)) and US20140030779. Recombination was catalyzed via expression of the Lambda phage Red genes from pRED-Amp (Gene Bridges, Heidelberg, Germany). Genes encoding levansucrase (sacB) from *Bacillus subtilis* and kanamycin resistance were integrated into the chromosome. Kanamycin was used to select for successful integrants. In a second double-crossover homologous recombination step, the integrated sequence containing the levansucrase gene and kanamycin resistance gene was replaced with an appropriate DNA sequence (deletion or insertion or mutation) and sucrose resistant clones were selected for kanamycin sensitivity. DNA sequences used in the homologous recombination steps outlined above were constructed via standard molecular biological techniques. Upon recombination, the chromosomal region encompassing the modification was PCR amplified and sequenced in order to verify that the expected modification occurred as planned. Flanking regions (between 500-1000 nt) covering any regulatory sequence were therefore sequence verified.

The following primers were used to confirm the cydAB deletions:

| Primer Designation | Primer Sequence | SEQ ID NO |
|---|---|---|
| cydAB F1 | AGCCAGGCAGTGGGATTGTG | 11 |
| cydAB R1 | GGCAAACATCTACATCGCATTC | 12 |

As a result, the following nucleotides were deleted: 1,309,961-1,310,181 (cydAB).

Fed-batch fermentations were performed with 1 L initial culture volume in 2 L Biostat B+ bioreactors (Sartorius; Cedex France) using M9 minimal medium supplemented with 20 g/L glucose. The temperature was controlled at 35° C., and the pH was controlled at 6.75 using 2 M NH$_4$OH or Na$_2$CO$_3$. Cells were grown aerobically until a peak weight-based oxygen uptake rate (wOUR) of 45 mmol O$_2$/kg/hr was reached. At this point, total oxygen supply (mmol/hr) was held constant but due to the increasing liquid volume, the wOUR gradually decreases resulting in microaerobic conditions [dissolved oxygen (DO) concentration=0 (i.e., below limits of detection); oxygen uptake rate=oxygen transfer rate]. All cultures reached DO=0 at 9 hours. Total fermentation time was 24 hr. Thus much of the growth occurred under oxygen limited conditions. No other nutrient limitations were imposed. Oxygen was measured using a Presens Oxy4 dissolved oxygen probe.

Total biomass formed, oxygen consumed, and biomass formed per oxygen consumed are reported in Table 23. The biomass value was calculated from the culture OD (1 OD equivalent=0.4 g dry cell weight per liter) and liquid volume. Deletion of cydAB allowed a greater amount of biomass to be formed per oxygen molecule consumed. Since the biomass yield on oxygen is higher in cyd strains, lower peak wOUR's can be used to generate the same amount of cell mass as cyd+ strains. Thus respiratory yield losses to CO$_2$ are lower in cyd strains compared to cyd+ strains.

TABLE 23

Total biomass formation, oxygen consumed, and biomass generated per oxygen consumed are provided for strain 7032 and 7143 at 24 hours of fermentation.

| Strain | Plasmid | Key Metabolic Modifications | Biomass Formed (g) | O2 Consumed (mmol) | Biomass/O2 (g/mmol) |
|---|---|---|---|---|---|
| 7032 | none | sucCD | 20.5 | 898 | 0.023 |
| 7143 | none | sucCD, cydAB | 26.3 | 918 | 0.029 |

Example VI

Increasing Product Yield of SucCD CydAB Deletion Strains by Deletion of PykF and/or Overexpression of PntAB This example demonstrates that the production of BDO per biomass can be increased in sucCD cydAB deletion strains by pntAB overexpression and/or deletion of pykF.

pykF was deleted in strain 7143 described in Example V. Strain 7143 lacks both sucCD and cydAB. Deletion of pykF from strain 7143 resulted in strain 7342. Deletion of pykF was achieved using a two-step double-crossover homologous recombination method as described previously (Yim et al, *Nature Chem Biol* 7:445-52 (2011)) and US20140030779. The following primers were used to confirm the pykF deletion:

| Primer Designation | Primer Sequence | SEQ ID NO |
|---|---|---|
| pykF F1 | AGCCAGGCAGTGGGATTGTG | 13 |
| pykF R1 | GGCAAACATCTACATCGCATTC | 14 |

As a result, the following nucleotides were deleted: 1,309,961-1,310,181 (pykF).

The pntAB genes were overexpressed in strains 7143 and 7342 using the expression vectors described in Example IV. pZS*-p115-13K-RBS-pntAB results in lower pntAB expression than pZS*-p115-pntAB due to the reduced strength of the RBS. Strains were cultured in a 96-well plate as described in Example I. Table 24 shows that the amount of BDO synthesized per biomass generated is increased upon deletion of pykF. Table 24 also shows that this increase is magnified in both strain 7143 and strain 7342 upon overexpressing pntAB.

TABLE 24

BDO production per OD in strains 7143 and 7342 with and without increased expression of pntAB. The averages of four replicate cultures are shown after 24 hours of culture time in 96-well plates.

| Strain | Plasmid | Key Metabolic Modifications | BDO (mM)/OD |
|---|---|---|---|
| 7143 | none | ΔsucCD, ΔcydAB | 16.3 |
| 7143 | pZS*-p115-13k-RBS-pntAB | ΔsucCD, ΔcydAB, pntAB overexpressed | 24.2 |
| 7143 | pZS*-p115-pntAB | ΔsucCD, ΔcydAB, pntAB overexpressed | 23.1 |
| 7342 | none | ΔsucCD, ΔcydAB, ΔpykF | 17.8 |
| 7342 | pZS*-p115-13k-RBS-pntAB | ΔsucCD, ΔcydAB, ΔpykF, pntAB overexpressed | 18.8 |
| 7342 | pZS*-p115-pntAB | ΔsucCD, ΔcydAB, ΔpykF, pntAB overexpressed | 19.5 |

Example VII

Increasing Product Yield of SucCD CydAB YciA Deletion Strains Upon Deletion of PykF and/or Overexpression of PntAB This example demonstrates that the production of BDO per biomass can be increased in sucCD cydAB yciA deletion strains by pntAB overexpression and/or deletion of pykF.

yciA was deleted in strain 7143 described in Example V. Strain 7143 lacks both sucCD and cydAB. Deletion of yciA from strain 7143 resulted in strain 7170. Deletion of yciA was achieved using a two-step double-crossover homologous recombination method as described in Yim et al. (Yim et al, *Nature Chem Biol* 7:445-52 (2011)) and US20140030779. The following primers were used to confirm the yciA deletion:

| Primer Designation | Primer Sequence | SEQ ID NO |
|---|---|---|
| yciA F1 | AGCCAGGCAGTGGGATTGTG | 15 |
| yciA R1 | GGCAAACATCTACATCGCATTC | 16 |

As a result, the following nucleotides were deleted: 1,309,961-1,310,181 (yciA).

pykF was deleted in strain 7170. Strain 7170 lacks sucCD, yciA, and cydAB. Deletion of pykF from strain 7170 resulted in strain 7341. Deletion of pykF was achieved using a two-step double-crossover homologous recombination method as described in Yim et al. (Yim et al, *Nature Chem Biol* 7:445-52 (2011)) and US20140030779. The following primers were used to confirm the pykF deletion:

| Primer Designation | Primer Sequence | SEQ ID NO |
|---|---|---|
| pykF F1 | AGCCAGGCAGTGGGATTGTG | 17 |
| pykF R1 | GGCAAACATCTACATCGCATTC | 18 |

As a result, the following nucleotides were deleted: 1,309,961-1,310,181 (pykF).

The pntAB genes were overexpressed in strains 7170 and 7341 using the expression vectors described in Example IV. pZS*-p115-13K-RBS-pntAB results in lower pntAB expression than pZS*-p115-pntAB due to the reduced strength of the RBS. Strains were cultured in a 96-well plate as described in Example I. Table 25 shows that the amount of BDO synthesized per biomass generated is increased upon deletion of pykF. Table 25 also shows that this increase is magnified in both strain 7170 and strain 7341 upon increasing pntAB expression.

TABLE 25

BDO production per OD in strains 7170 and 7341 with and without increased expression of pntAB. The averages of four replicate cultures are shown after 24 hours of culture time in 96-well plates.

| Strain | Plasmid | Key Metabolic Modifications | BDO (mM)/OD |
|---|---|---|---|
| 7170 | none | ΔsucCD, ΔcydAB, ΔyciA | 17.5 |
| 7170 | pZS*-p115-13k-RBS-pntAB | ΔsucCD, ΔcydAB, ΔyciA, pntAB overexpressed | 21.9 |
| 7170 | pZS*-p115-pntAB | ΔsucCD, ΔcydAB, ΔyciA, pntAB overexpressed | 20.1 |
| 7341 | none | ΔsucCD, ΔcydAB, ΔyciA, ΔpykF | 18.9 |
| 7341 | pZS*-p115-pntAB | ΔsucCD, ΔcydAB, ΔyciA, ΔpykF, pntAB overexpressed | 25.0 |

Example VIII

Increasing BDO Production of SucCD PykF Deletion Strain by Overexpression of PntAB This example demonstrates that the production of BDO can be increased in a sucCD pykF strain by overexpressing pntAB.

Host strain 7032 is similar to strain 6025 described above. It contains a restored wild-type cyo operon and is sucCD. The pntAB genes were overexpressed in strain 7032 using the expression vectors described in Example IV. pZS*-p115-13K-RBS-pntAB results in lower pntAB expression than pZS*-p115-pntAB due to the reduced strength of the RBS. Strains were cultured in a 96-well plate as described in Example I. Table 26 shows that the amount of BDO synthesized is increased upon overexpressing pntAB.

TABLE 26

BDO production in strain 7023 with and without increased expression of pntAB. The averages of four replicate cultures are shown after 24 hours of culture time in 96-well plates.

| Strain | Plasmid | Key Metabolic Modifications | BDO (mM) |
|---|---|---|---|
| 7023 | none | ΔsucCD, ΔpykF | 50.0 |
| 7023 | pZS*-p115-13k-RBS-pntAB | ΔsucCD, ΔpykF, pntAB overexpressed | 62.3 |
| 7023 | pZS*-p115-pntAB | ΔsucCD, ΔpykF, pntAB overexpressed | 53.0 |

Example IX

Increasing BDO Production of SucCD YciA Deletion Strain by Deleting Cyd

This example demonstrates that the production of BDO can be increased in a sucCD yciA strain by deleting cydAB.

Host strain 7313 is similar to strain 7341 described above. Both strains contain a restored wild-type cyo operon and are pykF, yciA, and sucCD. Strain 7341 contains a deletion in the cydAB genes. Table 27 shows that the amount of BDO synthesized is increased is strain 7341 versus 7313.

TABLE 27

BDO production in strains 7313 and 7341. The averages of four replicate cultures are shown after 24 hours of culture time in 96-well plates.

| Strain | Plasmid | Key Metabolic Modifications | BDO (mM) |
|---|---|---|---|
| 7313 | none | ΔsucCD, ΔyciA, ΔpykF | 47 |
| 7341 | none | ΔsucCD, ΔyciA, ΔpykF, ΔcydAB | 57 |

Example X

Improved Growth Rate in ClpA Deletion

This example demonstrates improved growth rate in strains with inactivated ClpA protein or a clpA gene deletion.

ClpA is the ATP-dependent chaperone component of the ClpAP and ClpAXP protease complexes, members of a diverse group of energy-dependent chaperone/protease complexes (Reid et al., *Proc. Natl. Acad. Sci. USA* 98(7): 3768-3772 (2001); Kessel et al, *J. Mol. Biol.* 250(5):587-594 (1995)). The ClpAP protease functions in diverse cellular activities including degradation of aggregated and ssrA-tagged proteins, adaptation and viability in stationary phase and the regulation of proteins responsive to carbon starvation and environmental stress (Gottesman et al, *Genes Dev.* 12:1338-47 (1998)).

| Protein | GenBank ID | GI Number | Organism |
|---|---|---|---|
| clpA | NP_415403.1 | GI: 16128850 | *Escherichia coli* |
| clpP | NP_414971.1 | 16128422 | *Escherichia coli* |
| clpX | NP_414972.1 | 16128423 | *Escherichia coli* | clpA Restoration in 5723.

Experiments were designed to test if restoration of clpA to wild type has an effect on growth. A base pair deletion (at base pair 254) in the clpA gene was found in a strain. The functional effect of this deletion is premature truncation, and thereby inactivation, of the ClpA protein, and the ClpAP and ClpAPX protease complexes. The clpA gene was restored to wild type in 5723 and tested for the growth differences between wild type clpA and clpA with the mutation. A version of the strain with a SacBKan cassette inserted 500 base pairs into the clpA gene.

Strains were tested for growth in FM1 medium in the Bioscreen. Restoring the clpA gene to its wild type form slightly impairs growth in 5723. The version with the SacBkan cassette does not have the same impairment. These results indicate that deletion or attenuation of ClpA component of the protease improved growth rate.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism comprising
   (i) a genetic alteration that attenuates a cytochrome oxidase encoded by cydA or cydB, or an orthologous gene thereof, and a genetic alternation that increases expression of a NAD(P) transhydrogenase encoded by pntAB or an orthologous gene thereof; and
   (ii) a genetic alternation that attenuates a succinyl-CoA synthetase encoded by sucCD or an orthologous gene thereof, and a genetic alternation that attenuates a CoA hydrolase encoded by yciA or an orthologous gene thereof.

2. The non-naturally occurring microbial organism of claim 1, further comprising a metabolically engineered pathway for producing a bioderived compound from a TCA cycle intermediate or a TCA cycle substrate.

3. A non-naturally occurring microbial organism of claim 1, wherein said microbial organism is selected from the group consisting of bacteria, yeast, fungus or other microorganism applicable to a fermentation process.

4. The non-naturally occurring microbial organism of claim 2, wherein the yield of the bioderived compound is increased relative to the absence of said genetic alteration.

5. A method of producing a bioderived compound comprising culturing a non-naturally occurring microbial organism of claim 2 for a sufficient period of time under conditions sufficient to produce said bioderived compound.

6. The non-naturally occurring microbial organism of claim 2, wherein said bioderived compound is selected from the group consisting of 4-hydroxybutyrate (4HB), 1,4-butanediol (1,4-BDO), 1,3-butanediol (1,3-BDO), polyhydroxylbutanoate (PHB), butadiene, adipate, 6-aminocaproate, caprolactam, methacrylic acid, isopropanol, long chain alcohols, hexamethylenediamene, methyl methacrylate, butanol, 3-butene-1-ol, 3-butene-2-ol and crotyl-alcohol.

7. A non-naturally occurring microbial organism of claim 3, wherein said microbial organism is *Escherichia coli*.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agccaggcag tgggattgtg                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcaaacatc tacatcgcat tc                                           22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
cgaatgaatg gctggcaag                                          19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccagacgcca ggcaaagtag                                         20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taaacgatgc cctgactacg c                                       21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggatagcgt caagcctgg                                          19

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacgaattcg ctagcaagag gagaagtcga catgtccaat tcactggccg tcgttttac    59

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaccctagga agctttctag agtcgaccta tgcggcatca gagcaga             47

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaggagaagt cgacatgaac gaacaatatt ccgcattgcg          40

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggaagctttc tagattagcc ggtattacgc atacctgcc           39

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agccaggcag tgggattgtg                                20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcaaacatc tacatcgcat tc                             22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agccaggcag tgggattgtg                                20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcaaacatc tacatcgcat tc                             22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
agccaggcag tgggattgtg                                          20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcaaacatc tacatcgcat tc                                       22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agccaggcag tgggattgtg                                          20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcaaacatc tacatcgcat tc                                       22
```